US007148001B2

(12) United States Patent  
Castillo et al.

(10) Patent No.: US 7,148,001 B2  
(45) Date of Patent: Dec. 12, 2006

(54) *IN VITRO* FORMATION OF CONGOPHILIC MALTESE-CROSS AMYLOID PLAQUES TO IDENTIFY ANTI-PLAQUE THERAPEUTICS FOR THE TREATMENT OF ALZHEIMER'S AND PRION DISEASES

(75) Inventors: Gerardo Castillo, Seattle, WA (US); Alan D. Snow, Lynnwood, WA (US)

(73) Assignee: University of Washington, Seattle, WA (US)

( * ) Notice: Subject to any disclaimer, the term of this patent is extended or adjusted under 35 U.S.C. 154(b) by 461 days.

(21) Appl. No.: 10/007,779

(22) Filed: Nov. 30, 2001

(65) Prior Publication Data

US 2002/0168753 A1 Nov. 14, 2002

Related U.S. Application Data

(63) Continuation of application No. 09/267,795, filed on Mar. 12, 1999, now abandoned.

(60) Provisional application No. 60/077,924, filed on Mar. 13, 1998.

(51) Int. Cl.
*C12Q 1/00* (2006.01)
*A61K 49/00* (2006.01)

(52) U.S. Cl. .......................................... 435/4; 424/9.2

(58) Field of Classification Search .................. 435/4
See application file for complete search history.

(56) References Cited

OTHER PUBLICATIONS

Snow et al. "An Important Role of Heparan Sulfate Proteoglycan (Perlecan) in a Model System for the Deposition and Persistence of Fibrillar Aβ'-Amyloid in Rat Brain," Neuron, vol. 12, pp. 219-234, Jan. 1994.
Castillo et al. "Perlecan Binds to the β-Amyloid Proteins (Aβ) of Alzheimer's Disease, Acclerates AβFibril Formation, and Maintains AβFibril Stability," Journal of Neurochemistry, vol. 69, No. 6, pp. 2452-2464, 1997.
Desdouits et al. "Amyloid β Peptide Formation in Cell-free Preparations," Journal of Biological Chemistry, vol. 271, No. 40, pp. 24670-24674, Oct. 4, 1996.
Jensen et al. "Binding of Aβ to α- and β-Synucleins: Identification of Segments in α-Synuclein/NAC Precursor that Bind Aβand NAC," Biochem. J., vol. 323, pp. 539-546, 1997.
Bame et al. "Aβ(1-40) Prevents Heparanase-catalyzed Degradation of Heparan Sulfate Glycosaminoglycans and Proteoglycans *in Vitro*," Journal of Biological chemistry, vol. 272, No. 27, pp. 17005-17011, Jul. 4, 1997.
Castillo et al. "Novel Purification and Detailed Characterization of Perlecan Isolated from the Engelbreth-Holm-Swarm Tumor for Use in an Animal Model of Fibrillar AB Amyloid Persistence in Brain." J. Biochem, vol. 120, No. 2, pp. 433-444, 1996.
Verga et al. "Alzheimer Patients and Down Patients; Cerebral Preamyloid Deposits Differ Ultrastructurally and Histochemically from the Amyloid of Senile Plaques." Neuroscience Letters, vol. 105, pp. 294-298, 1989.
Barcikowsha et al. "About the Presence of Paired Helical Filaments in Dystrophic Neurites Participating in the Plaque Formation." Neuropathol, vol. 78, pp. 225-231, 1989.
Ikeda et al. "Morphology and Distribution of Plaque and Related Ddeposits in the Brains of Alzheimer's Disease and Control Cases." Laboratory Investigation, vol. 60, No. 1, p. 113-122, 1989.
Masliah et al. "Re-Evaluation of the Structural Organization of Neuritic Plaques in Alzheimer's Disease." Journal of Neuropathology and Experimental Neurology, vol. 52, No. 6, pp. 619-632, Nov., 1993.
Wisniewski et al. "Spectrum of Morphological Appearance of Amyloid Deposits in Alzheimer's Disease." Acta Neuropathol, vol. 78, pp. 337-347, 1989.
Schmidt et al. "Chemical and Immunological Heterogeneity of Fibrillar Amyloid in Plaques of Alzheimer's Disease and Down's Syndrome Brains Revealed by Confocal Microscopy." American Journal of Pathology, vol. 147, No. 2, pp. 503-515, Aug. 1995.
Dickson. "The Pathogenesis of Senile Plaques." Journal of Neuropathology and Experimental Neurology, vol. 56, No. 4, pp. 321-339, Apr. 1997.
Selkoe et al. "Isolation of Low-Molecular-Weight Proteins from Amyloid Plaque Fibers in Alzheimer's Disease." Journal of Neurochemistry, vol. 46, No. 6, pp. 1820-1834, 1986.
Snow et al. "The Presence of Heparin Sulfate Proteoglycans in the Neuritic Plaques and Congophilic Angiopathy in Alzheimer's Disease." American Journal of Pathology, vol. 133, No. 3, pp. 456-463, Dec. 1988.
Glenner et al. "Alzheimer's Disease: Initial Report of the Purification and Characterization of a Novel Cerebrovascular Amyloid Protein." Biochemical and Biophysical Research Communications, vol. 120, No. 3, pp. 885-890, May 16, 1984.

(Continued)

*Primary Examiner*—Janet L. Andres
*Assistant Examiner*—Kimberly A. Ballard
(74) *Attorney, Agent, or Firm*—Patrick M. Dwyer

(57) ABSTRACT

Co-incubation of an amyloid protein with sulfated macromolecules as a method for the formation of amyloid plaques. The amyloid protein may be the beta-amyloid protein or the prion protein or the like. Amyoid plaque formation in one embodiment proceeds in vitro and desirably produces amyloid plaques that stain with Congo red and demonstrate a maltese-cross pattern when viewed under polarized light. The method also produces amyloid plaques that demonstrate an "amyloid star" appearance when viewed by transmission electron microscopy. An in vivo assay is also presented for selecting a candidate therapeutic agent for inhibiting or disrupting amyloid plaque deposition or persistence.

10 Claims, 9 Drawing Sheets

OTHER PUBLICATIONS

Masters et al. "Amyloid Plaque Core Protein in Alzheimer Disease and Down Syndrome." Medical Sciences, vol. 82, pp. 4245-4249, Jun. 1983.
Who-Iuis Nomenclature Sub-Committee. "Nomenclature of Amyloid and Amyloidosis." Bulletin of the World Health Organization, vol. 71, No. 1, pp. 105-108, 1993.
Tanzi et al. "Protease Inhibitor Domain Encoded by an Amyloid Protein Precursor Mrna Associated with Alzheimer's Disease." Nature, vol. 331, pp. 528-532, Feb. 1988.
Kitaguchi et al. "Novel Precursor of Alzheimer's Disease Amyloid Protein Shows Protease Inhibitory Activity." Nature, vol. 331, pp. 530-532, Feb. 11, 1988.
Ponte et al. "A New A4 Amyloid mRNA Contains a Domain Homologous to Sering Proteinase Inhibitors." Nature, vol. 311, pp. 525-527, Feb. 11, 1988.
Grundke-Iqbal et al. "Abnormal Phosphorylation of the Microtubule-Associated Protein τ (tau) in Alzheimer Cytosheletal Pathology." Proc. Natl. Acad. Sci. USA, vol. 83, pp. 4913-4917, Jul. 1986.
Kosik et al. "Microtubule-Associated Protein Tau τ is a Major Antigenic Component of Paired Helical Filaments in Alzheimer Disease." Proc. Natl. Acad. Sci. USA, vol. 83, pp. 4044-4048, Jun. 1986.
Lee et al. "A68: A Major Subunit of Paired Helical Filaments and Derivatized Forms of Normal Tau." Science, vol. 25, pp. 675-678, Feb., 1991.
Mandybur. "Cerebral Amyloid Angiopathy: The Vascular Pathology and Complications." Journal of Neuropathology and Experimental Neurology, vol. 45, No. 1, pp. 79-90, Jan, 1986.
Pardridge et al. "Amyloid Angiopathy of Alzheimer's Disease: Amino Acid Composition and Partial Sequence of a 4,200-Dalton Peptide Isolated from Cortical Microvessels." Journal of Neurochemistry, vol. 49, No. 5, pp. 1394-1401, 1987.
Pike et al. "In Vitro Aging of β-Amyloid Protein Causes Peptide Aggregation and Neurotoxicity." Brain Research, vol. 563, pp. 311-314, 1991.
Pike et al. "Structure-Activity Analyses of β-Amyloid Peptides: Contributions of the β25-35 Region to Aggregation and Neurotoxicity." Journal of Neurochemistry, vol. 64, No. 1, pp. 253-265, 1995.
Harrigan et al. "Beta Amyloid is Neurotoxic in Hippocampal Slice Cultures." Neurobiology of Aging, vol. 16, No. 5, pp. 779-789, 1995.
Games et al. "Alzheimer-Type Neuropathology in Transgenic Mice Overexpressing V717F β-Amyloid Precursor Protein." Nature, vol. 373, pp. 523-527, Feb. 9, 1995.
Hsiao et al. "Age-Related CNS Disorder and Early Death in Transgenic FVB/N Mice Overexpressing Alzheimer Amyloid Precursor Proteins." Neuron, vol. 15, pp. 1203-1218, Nov. 1995.
Flood et al. "Amnestic Effects in Mice of Four Synthetic Peptide Homologous to Amyloid β Protein from Patients with Alzheimer Disease." Proc. Natl. Acad. Sci. USA, vol. 88, pp. 3363-3366, Apr. 1991.
Flood et al. "An Amyloid β-Protein Fragment, A β[12-28], Equipotently Impairs Post-Training Memory Processing When Injected into Different Limbic System Structures." Brain Research, vol. 663, pp. 271-276, 1994.
Van Broeckhoven et al. "Amyloid β Protein Precursor Gene and Hereditary Cerebral Hemorrhage with Amyloidosis (Dutch)." Science, vol. 248, pp. 1120-1124, Jun. 1990.
Van Broeckhoven. "Molecular Genetics of Alzheimer Disease: Identification of Genes and Gene Mutations." Eur Neurol, vol. 35, pp. 8-19, Oct. 1991.
Haass et al. "The Swedish Mutation Causes Early-Onset Alzheimer's Disease by β-Secretase Cleavage within the Secretory Pathway." Nature Medicine, vol. 1, No. 12, pp. 1291-1296, Dec. 1995.
Murrell et al. "A Mutation in the Amyloid Precursor Protein Associated with Hereditary Alzheimer's Disease." Science, vol. 254, pp. 97-99, Oct. 1991.
Hardy et al. "Framing β-Amyloid." Nature Genetics, vol. 1, pp. 233-234, Jul. 1992.

Amaguchi et al. "Variety of Cerebral Amyloid Deposits in the Brains of the Alzheimer-Type Dementia Demonstrated β Protein Immunostaining." Neuropathol, vol. 76, pp. 541-549, 1988.
Giaccone et al. "Down Patients: Extracellular Preamyloid Deposits Precede Neuritic Degeneration and Senile Plaques." Neuroscience Letters, vol. 97, pp. 232-240, 1989.
Allsop et al. "Early Senile Plaques in Down's Syndrome Brains Show a Close Relationship with Cell Bodies of Neurons." Neuropathology and Applied Neurobiology, vol. 15, pp. 531-542, 1989.
Ikeda et al. "Brief Communication, Evidence of Amyloid β-Protein Immunoreactive Early Plaque Lesions in Down's Syndrome Brains." Laboratory Investigation, vol. 61, No. 1, pp. 133-137, 1989.
Mann et al. "An Analysis of the Morphology of Senile Plaques in Down's Syndrome Patients of Different Ages Using Immunocyotochemical and Lectin Histochemical Techniques." Neuropathology and Applied Neurobiology, vol. 15, pp. 317-329, 1989.
Pappolla et al. "The Genesis of the Senile Plaque, Further Evidence in Support of its Neuronal Origin." American Journal of Pathology, vol. 141, No. 5, pp. 1151-1159, Nov. 1992.
Lemere et al. "Sequence of Deposition of Heterogeneous Amyloid β-Peptides and APO E in Down Syndrome: Implications for Initial Events in Amyloid Plaque Formation." Neurobiology of Disease; vol. 3, pp. 16-32, Article No. 0003, 1996.
Pappolla et al. "Image Analysis Microspectroscopy Shows that Neurons Participate in the Genesis of a Subset of Early Primitive (Diffuse) Senile Plaques." American Journal of Pathology, vol. 139, No. 3, pp. 599-607, Sep. 1991.
Brockman et al. "Creutzfeldt-Jakob Disease Prion Proteins in Human Brains." New England Journal of Medicine, vol. 312, No. 2, pp. 73-77, Jan. 10, 1985.
Kitamoto et al. "Amyloid Plaques in Creutzgeldt-Jakob Disease Stain with Prion Protein Antibodies." Annals of Neurology, vol. 20, No. 2, pp. 204-208, Aug. 1986.
Manuelidis. "Creutzfeldt-Jakob Disease." Journal of Neuropathology and Experimental Neurology, vol. 44, No. 1, pp. 1-17, Jan. 1985.
Brown et al. "Creutzfeldt-Jakob Disease: Clinical Analysis of a Consecutive Series of 230 Neuropathologically Verified Cases." Annals of Neurology, vol. 20, No. 5, pp. 597-602, Nov. 1986.
Tateishi et al "Gerstmann-Straussler-Scheinker Disease: Immunohistological and Experimental Studies." Annals of Neurology, vol. 24, No. 1, pp. 35-40, Jul. 1988.
Gajdusek. "Unconventional Viruses and the Origin and Disappearance of Kuru." Science, vol. 197, No. 4307, Sep. 2, 1977.
Hashimoto et al. "Immunohistockemical Study of Kuru Plaques Using Antibodies Against Synthetic Prion Protein Peptides." Acta Neuropathol, vol. 83, pp. 613-617, 1992.
Pearlman et al. "Clinical Significance of Types of Cerebellar Amyloid Plaques in Human Spongiform Encephalopathies," Neurology, vol. 38, pp. 1249-1254, Aug. 1988.
Coria et al. "Isolation and Characterization of Amyloid P Component from Alzheimer's Disease and Other Types of Cerebral Amyloidosis," Laboratory Investigation, vol. 58, No. 4 pp. 454-458. 1988.
Abraham et al. "Immunochemical Identifiction of the Serine Protease Inhibitor α1-Antichmotrypsin in the Brain Amyloid Deposits of Alzheimer's Disease," Cell, vol. 52. pp. 487-501. Feb. 1988.
Namba et al. "Apolipoprotein E Immunoreactivity in Cerebral Amyloid Deposits and Neurofibrillary tangles in Alzheimer's Disease and Kuru Plaque Amyloid in Cretzfeldt-Jacob Disease." Brain Research, vol. 541 pp. 163-166, 1991.
Strittmatter et al. "Isoform-Specific Interactions of Apolipoprotein E with Microtubule-Associated Protein Tau:Implications for Alzheimer Disease," Proc. National Academy of Science USA, vol. 91. pp. 11183-11186, Nov. 1994.
Strittmatter et al. "Apolipoprotein E and Alzheimer Disease." Proc. National Academy of Science USA, vol. 92, pp.4725-4747, May 1995.

Eikelenboom et al. "Complement Activation in amyloid Plaques in Alzheimer's Dementia," Virchows Archiv B Cell Pathol, vol. 56, pp. 259-262. 1989.

McGeer et al. "Immune System Response in Alzheimer's Disease," The Canadian Journal of Neurological Sciences, vol. 16. pp. 516-527. 1989.

Rogers "Inflammation 7and Alzheimer's Disease," CNS Drugs 1, vol. 4, pp. 241-244. 1994.

Snow et al. "Heparan Sulfate Proteoglycan in Diffuse Plaques of Hippocampus but Not of Cerebellum in Alzheimer's Disease Brain," American Journal of Pathology, vol. 144, No. 2, pp. 337-347. Feb. 1994.

Murtomaki et al. "Laminin and Its Neurite Outgrowth-Promoting Domain in the Brain in Alzheimer's Disease and Down's Syndrome Patients," Journal of Neuroscience Research, vol. 32. pp. 261-273. 1992.

Perlmutter et al. "Microangiopathy, the Vascular Basement Membrane and Alzheimer's Disease: A Review," Brain Research Bulletin, vol. 24. pp. 677-686. 1990.

Perlmutter et al. "Vascular Basement Membrane Components and the Lesions of Alzheimer's Disease: light and Electron Microscopic Analyses," Microscopy Research and Technique, vol. 28. pp. 204-215. 1994.

Kawai et al. "The Relationship of Amyloid Plaques to Cerbral Cappilaries in Alzheimer's Disease," American Journal of Pathology, vol. 137. No. 6. pp. 1435-1446. Dec. 1990.

Luthert et al. "A Quantitative Study of the coincidence of Blood Vessels and A4 Protein Deposits in Alzheimer's Disease," Neuroscience Letters, vol. 126. pp. 110-112. 1991.

Kawai et al. "Serial Reconstruction of β-protein Amyloid Plaques: Relationship to Microvessels and Size Distribution," Brain Research, vol. 592. pp. 278-282. 1992.

Brandan et al. "Extracellular Matrix Components and Amyloid in Neuritic Plaques of Alzheimer's Disease," General Pharmaceutical, vol. 24. No. 5. pp. 1063-1068. 1993.

Hassell et al. " Isolation of a Heparan Sulfate-Containing Proteoglycan from Basement Membrane," Proc. National Academy of Science USA. vol. 77. No. 8. pp. 4494-4498. Aug. 1980.

Noonan et al. "The Complete Sequence of Perlecan, A Basement Membrane Heparan Sulfate Proteoglycan, Reveals Extensive Similarity with Laminin A Chain, Low Density lipoprotein-Receptor, and the Neural Cell Adhesion Molecule," The Journal of Biological Chemistry. vol. 266. No. 34. pp. 22939-22947. Dec. 1991.

Murdoch et al. "Primary Structure of the Human Heparan Sulfate Proteoglycan from Basement Membrane (HSPG2/Perlecan)," The Journal of Biological Chemistry. vol. 267. No. 12. pp. 8544-8557. Apr. 1992.

Kallunki et al. "Human Basement Membrane Heparan Sulfate Proteoglycan Core Protein: A 467-kD Protein Containing Multiple Domains Resembling Elements of the Low Density Lipoprotein Receptor, Laminin, Neural Cell Adhesion Molecules, and Epidermal Growth Factor," The Journal of Cell Biology. vol. 116. No. 2 pp. 559-571. Jan. 1992.

Iwatsubo et al. "Visualization of Aβ42(43) and Aβ40 in Senile Plaques with End-Specific Aβ Monoclonals: Evidence That an Initially Deposited Species is Aβ42(43)," Neuron. vol. 13, pp. 45-53, Jul. 1994.

Suzuki et al. "High Tissue Content of Soluble β1-40 is linked to Cerebral Amyloid Angiopathy," American Journal of Pathology. vol. 145 No. 2, pp. 452-460, Aug. 1994.

Snow et al. "Peripheral Distribution of Dermatan Sulfate Proteoglycans (Decorin) in Amyloid-Containing Plaques and Their Presense in Neurofibrillary Tangles of Alzheimer's Disease," The Journal of Histochemistry and Cytochemistry. vol. 40. No. 2. pp. 105-113. 1992.

Snow et al. "Identification and Immunolocalization of a New Class of Proteoglycan (Keratan Sulfate) to the Neuritic Plaques of Alzheimer's Disease," Experimental Neurology. vol. 138. pp. 305-317. 1996.

DeWitt et al. "Chondroitin Sulfate Proteoglycans Are Associated with the Lesions of Alzheimer's Disease," Experimental Neurology. vol. 121. pp. 149-152. 1993.

Kisilevsky et al. "Arresting Amyloidosis In Vivo Using Small-Molecule Anionic Sulphonates or Sulphates: Implications for Alzheimer's Disease," Nature Medicine, vol. No. 2. pp. 143-148. Feb. 1995.

Bjornsson et al. "Simultaneous Preparation and Quantitation of Proteoglycans by Precipitation with Alcian Blue," Analytical Biochemistry. vol. 210. pp. 282-291. 1993.

DeWitt et al. "Astrocytes Regulate Microglial Phagocytosis of Senile Plaque Cores of Alzheimer's Disease," Experimental Neurology. vol. 149. pp. 329-340. 1998.

Puchtler et al. "On the Binding of Congo Red by Amyloid," pp. 355-364. Sep. 1961.

Reynolds et al. "The Use of Lead Citrate at High pH As an Electron-Opaque Stain in Electron Microscopy," Brief Notes. pp. 208-212. Nov. 1962

TAM "Acid Deprotection Reactions in Peptide Synthesis," Macromolecular Sequencing and Synthesis, vol. 13.pp. 153-184. 1998.

Hunter et al. "Preparation of Iodine-131 Labelled Human Growth Hormone of High Specific Activity," Nature, pp. 495-496. May. 1962.

Bolton et al. "The Labelling of Proteins to High Specific Radioactivities by Conjugation to a [125]I-Containing Acylating Agent," Biochemistry Journal. vol. 133, pp. 529-539. Feb. 1973.

Snow et al. "Heparin Modulates the Composition of the Extracellular Matrix Domain Surrounding Arterial Smooth Muscle Cells," American Journal of Pathology. vol. 137. No. 2. pp. 313-330. Aug. 1990.

Elghetany et al. "Methods for Staining Amyloid in Tissues: A Review," Stain Technology, vol. 65. No. 4. pp. 201-212. 1988.

Kitamoto et al. "Formic Acid Pretreatment Enhances Immunostaining of Cerebral and Systemic Amyloids," Laboratory Investigation vol. 57. No. 2. pp. 230-236. 1987.

SEQUENCE LISTING (1) GENERAL INFORMATION:

(iii) NUMBER OF SEQUENCES: 1

(2) INFORMATION FOR SEQ ID NO: 1:

```
    (i) SEQUENCE CHARACTERISTICS:
        (A) LENGTH: 40 AMINO ACIDS
        (B) TYPE: AMINO ACID
        (C) STRANDEDNESS: <Unknown>
        (D) TOPOLOGY: LINEAR (ii) MOLECULE TYPE: PROTEIN (xi) SEQUENCE DESCRIPTION: SEQ ID NO: 1:

Asp Ala Glu Phe Arg His Asp Ser Gly Tyr Glu Val His His Gln
 1               5                  10                  15

Lys Leu Val Phe Phe Ala Glu Asp Val Gly Ser Asn Lys Gly Ala
                20                  25                  30

Ile Ile Gly Leu Met Val Gly Gly Val Val
                35                  40
```

IN VITRO FORMATION OF CONGOPHILIC MALTESE-CROSS AMYLOID PLAQUES TO IDENTIFY ANTI-PLAQUE THERAPEUTICS FOR THE TREATMENT OF ALZHEIMER'S AND PRION DISEASES

This application is a continuation of 09/267,795 filed Mar. 12, 1999, now abandoned, which claims priority to provisional application Ser. No. 60/077,924 filed Mar. 13, 1998.

TECHNICAL FIELD

The invention relates to methods of formation of particular amyloid plaques and to diagnostic and therapeutic applications for such plaques in the treatment of Alzheimer's and Prion Diseases.

BACKGROUND OF THE INVENTION

Alzheimer's disease is characterized by the accumulation of a 39–43 amino acid peptide termed the beta-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. A variety of morphologically distinct types of Aβ-containing plaques have been described in the brains of Alzheimer's disease patients including diffuse plaques (which demonstrate Aβ immunoreactivity but do not stain for fibrillar amyloid using amyloid stains such as Congo red and Thioflavin S), neuritic plaques (which contain a central amyloid core which stains with Congo red and Thioflavin S, and which is surrounded by dystrophic neurites) and compact, burned-out or "amyloid star" plaques (which usually demonstrate a maltese-cross pattern when stained with Congo red and viewed under polarized light). Investigators have hypothesized that in Alzheimer's disease there is most likely a conversion from the diffuse plaque to the neuritic plaque to the compact, burned-out plaque. However, the mechanism of this conversion and the essential components involved have never been elucidated. In addition, the formation of compact plaques in vitro which demonstrate a maltese-cross pattern when stained with Congo red and viewed under polarized light has never been achieved.

DISCLOSURE OF THE INVENTION

The invention relates to the discovery of the mechanism and essential components required to form congophilic maltese-cross spherical amyloid plaques (i.e. "compact plaques" or "amyloid stars") in vitro that are virtually identical to congophilic maltese-cross compact plaques present in human Alzheimer's disease brain, and described methods to consistently form such Alzheimer's plaques for their utilization in a number of different assay techniques and animal models to identify anti-plaque therapeutics. Compact amyloid plaques formed following co-incubation of beta-amyloid protein (Aβ) (residues 1–40 but not residues 1–42) and perlecan, other highly sulfated glycosaminoglycans (GAGs) (i.e. heparan sulfate and heparin) or related sulfated macromolecules (i.e. dextran sulfate, pentosan polysulfate and polyvinyl sulphonate), when incubated at 37° C. for 3 to 5 days, and under appropriate molar/weight ratios of Aβ:sulfated proteoglycans/GAGs, as disclosed herein. Such compact congophilic maltese-cross amyloid plaques were not formed following a 1 week (at 37° C.) incubation of Aβ 1–40 or 1–42 only, or when Aβ 1–40 or 1–42 was co-incubated for 1 week under the same conditions with other known amyloid plaque components present in human Alzheimer's disease brain including P component, alpha$_1$-antichymotrypsin, Apo E, C1q, C3, laminin, fibronectin or type IV collagen. The 10–40 μm amyloid plaques (average diameter=25 μm) formed by co-incubation of Aβ 1–40 with perlecan, other highly sulfated GAGs or related sulfated macromolecules have all of the characteristics of compact amyloid plaques present in human Alzheimer's disease brain including: 1) amyloid plaques which demonstrate a maltese-cross pattern when stained with Congo red and viewed under polarized light, 2) a spherical "amyloid star" morphology with radiating bundles of amyloid fibrils (each with a fibril diameter of 7–10 nm) appearing to emanate from the center of the plaque when viewed by transmission electron microscopy, and 3) amyloid plaques similar in surface morphology and spherical shape to isolated amyloid cores derived from Alzheimer's disease brain when viewed by scanning electron microscopy. The invention further relates to the utility of such amyloid plaques formed in vitro as screening tools for the identification of Alzheimer's disease anti-plaque therapeutics.

SUMMARY OF THE INVENTION

The present invention has determined the mechanisms of congophilic, maltese-cross amyloid plaque (i.e. "compact plaques" or "amyloid star" plaques) formation in vitro and the essential components involved, and describes unique in vitro and animal model methodologies for the use of this technology to discover anti-plaque therapeutics for the treatment of Alzheimer's disease. Perlecan (a specific heparan sulfate proteoglycan implicated in Alzheimer's disease amyloidosis), highly sulfated glycosaminoglycans (GAGs)(ie. heparin and heparan sulfate), and related sulfated GAG macromolecules (ie. dextran sulfate, pentosan sulfate, polyvinyl sulphonate) were discovered to all induce beta-amyloid protein (Aβ)(residues 1–40) transformation into amyloid plaque deposits (at 37° C. within 3–5 days with the right mixture and concentration of components) in vitro that are virtually identical to congophilic maltese-cross compact amyloid plaques present in human Alzheimer's Disease brain. The molar and/or weight ratios of Aβ (1–40) to other essential components (described above) were critical for amyloid plaque formation. Various co-components known to be present in Alzheimer's Disease plaques or implicated in Alzheimer's disease amyloidosis were tested for their potential ability to induce compact amyloid plaque formation including P component, alpha$_1$-antichymotrypsin, ApoE, C1q, C3, laminin, type IV collagen, fibronectin and perlecan. Components were incubated at 37° C. with beta-amyloid protein (Aβ) 1–40 and 1–42 for prolonged periods (up to 1 week). Different conditions (i.e. concentrations, molar/weight ratios, incubation times) were tried in an effort to reduplicate the formation of the compact congophilic maltese-cross, "amyloid star" plaques observed in Alzheimer's Disease brain. Under the appropriate conditions as disclosed herein, perlecan (and not other plaque components as listed above) was able to induce Aβ 1–40 to form congophilic maltese-cross, spherical amyloid "star" plaques. Testing of different GAGs and related macromolecules including heparin, heparan sulfate, chondroitin-4-sulfate, chondroitin-6-sulfate and dermatan sulfate revealed that heparin/heparan sulfate GAGs were also effective amyloid plaque inducers (i.e. congophilic maltese-cross and compact amyloid plaques) under the appropriate conditions. Similar amyloid plaque induction was also achieved with other highly sulfated macromolecules including dextran sulfate, pentosan polysulfate and polyvinyl sulphonate, but only after the proper molar/weight ratios of Aβ: sulfated macromolecules were determined. Induction of compact amyloid plaque formation by perlecan, highly sulfated GAGs and related sulfated macromolecules with Aβ 1–40, did not occur when using Aβ 1–42 under the same conditions. This latter finding suggests that compact amyloid plaque formation does not likely occur in the human Alzheimer's disease brain until the two hydrophobic residues at the carboxyl-end of Aβ 1–42 are cleaved. Further studies revealed that the sulfate residues on GAGs or related sulfated macromolecules were critical for compact amyloid plaque induction as partial or complete removal of sulfate from heparin resulted in complete loss of compact amyloid plaque formation. Transmission and scanning electron microscopy indicated that the amyloid plaques formed by co-incubation of Aβ (1–40) plus perlecan, highly sulfated GAGs or highly sulfated GAG related macromolecules, had virtually identical characteristics and morphology to that of amyloid plaque cores isolated from human Alzheimer's disease brain. These discoveries indicate that the congophilic maltese-cross and compact amyloid plaques observed in Alzheimer's disease brain are likely formed over time by the co-deposition and co-accumulation of perlecan and/or highly sulfated PGs/GAGs with Aβ 1–40. Understanding the requirements to consistently produce amyloid plaque formation in vitro allows for new screening techniques to identify anti-amyloid plaque therapeutics for the treatment of Alzheimer's disease.

FEATURES OF THE INVENTION

A primary object of the present invention is to provide methods for the in vitro formation of compact amyloid plaques which have similar characteristics to compact amyloid plaques in human Alzheimer's disease brain. Such characteristics of these plaques include, but are not limited to a) spherical or compact shape, b) a maltese-cross pattern (i.e. red color of plaque 90 degrees to green color of plaque) of congophilia following staining with Congo red and when viewed under polarized light, c) positive staining with Thioflavin S when viewed by fluorescence microscopy, d) spherical and/or "amyloid star" appearance when viewed by transmission electron microscopy, and/or e) spherical or compact in shape (with plaques 10–40 μM in diameter) when viewed by scanning electron microscopy.

Another object of the present invention is to provide methods to form congophilic maltese-cross, compact amyloid plaques in vitro, using Aβ and sulfated proteoglycans (PGs) or portions thereof. Such sulfated PGs include, but are not limited to, PGs which contain glycosaminoglycans (GAGs) of the heparan sulfate, dermatan sulfate, chondroitin sulfate, or keratan sulfate class. These PGs include, but are not limited to, perlecan, ~220 kDa HSPG (as described herein), glypican, cerebroglycan, aggrecan, synaptoglycan (SV2PG), syndecan, N-syndecan (i.e. syndecan-3), syndecan-1, syndecan-4, neurocan, phosphacan, decorin, biglycan, versican, amphiglycan, lumican, PG-M, PG-M (3), agrin, betaglycan, claustrin, brevican, appican, epican, and neuroglycan-C, or fragments thereof.

In a preferred embodiment such compact amyloidplaque formation is achieved by the co-incubation of Aβ 1–40 with perlecan following incubation in distilled water or Tris-buffered saline (pH 7.4) at 37° C. for 1 week, and under the appropriate Aβ:perlecan weight and/or molar ratios as described herein. In a preferred embodiment, 1 mg of Aβ 1–40 is dissolved in 1 ml of double distilled water or Tris-buffered saline (pH 7.4) to produce a stock solution of 1 mg/ml. 25 μl of the Aβ 1–40 stock solution is then added to a microcentrifuge tube containing 20 μg of lyophilized perlecan (isolated from the Engelbreth-Holm-Swarm tumor as described in Castillo et al, *J. Biochem.* 120:433–444, 1996), and then made up to a final volume of 250 μl, and incubated for 1 week at 37° C. In this preferred embodiment, the Aβ:perlecan molar ratio is 250:1, and the Aβ:perlecan weight ratio is 1:0.8. In other preferred embodiments, 25 μM of Aβ 1–40 is incubated in distilled water or Tris-buffered saline (pH 7.4) with 125 nM of perlecan, or 125 μM of Aβ 1–40 is incubated in distilled water or Tris-buffered saline (pH 7.4) with 0.625 μM of perlecan. In these latter two preferred embodiments, the Aβ:perlecan molar ratio is 200:1 and the Aβ:perlecan weight ratio is 1:1.

In other preferred embodiments to produce compact amyloid plaque formation, Aβ 1–40 is incubated with perlecan (assuming a molecular weight for perlecan of 800,000) in distilled water or Tris-buffered saline at 37° C. for at least 3 to 5 days, but preferably 1 week, within a range of Aβ:perlecan molar ratios from 50:1 to 500:1, including Aβ:perlecan molar ratios of 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 155:1, 160:1, 165:1, 170:1, 175:1, 180:1, 185:1, 190:1, 195:1, 200:1, 205:1, 210:1, 215:1, 220:1, 225:1, 230:1, 235:1, 240:1, 245:1, 250:1, 255:1, 260:1, 265:1, 270:1, 275:1, 280:1, 285:1, 290:1, 295:1, 300:1, 305:1, 310:1, 315:1, 320:1, 325:1, 330:1, 335:1, 340:1, 345:1, 350:1, 355:1, 360:1, 365:1, 370:1, 375:1, 380:1, 385:1, 390:1, 395:1, 400:1, 405:1, 410:1, 415:1, 420:1, 425:1, 430:1, 435:1, 440:1, 445:1, 450:1, 455:1, 460:1, 465:1, 470:1, 475:1, 480:1, 485:1, 490:1, 495:1 and 500:1, but preferably 200:1 and 250:1.

In other preferred embodiments to produce compact amyloid plaque formation, Aβ 1–40 is incubated with perlecan in distilled water or Tris-buffered saline at 37° C. for at least 3 to 5 days, but preferably 1 week, within a range of Aβ:perlecan weight ratios from 1:0.4–1:100, including Aβ:perlecan weight ratios of 1:0.4, 1:0.5, 1:0.8, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1;98, 1:99, 1:100, but preferably 1:1 and 1:0.8.

Another object of the present invention is to provide methods to form congophilic maltese-cross compact amyloid plaques in vitro, using Aβ and GAGs or portions thereof. Such GAGs include but are not limited to heparan sulfate, heparin, dermatan sulfate, chondroitin-4-sulfate, chondroitin-6-sulfate, keratan sulfate, and/or hyaluronic acid. In a preferred embodiment such compact amyloid plaque formation is achieved by the co-incubation of Aβ 1–40 with heparin or Aβ 1–40 with heparan sulfate following incubation at 37° C. for 1 week, and under the appropriate Aβ:heparin/heparan sulfate weight and/or molar ratios as described herein.

In a preferred embodiment congophilic maltese-cross compact amyloid plaques are formed utilizing Aβ 1–40 with heparin. In this preferred embodiment Aβ 1–40 at 25 μM or 125 μM is incubated in distilled water or Tris-buffered saline (pH 7.4) with heparin at 37° C. for at least 3 to 5 days, but preferably 1 week, within a range of Aβ:heparin molar ratios from 1:0.5 to 1:100, including 1:0.5, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In another preferred embodiment congophilic maltese-cross compact amyloid plaques are formed utilizing Aβ 1–40 with non-anticoagulant heparins. In this preferred embodiment Aβ 1–40 at 25 μM or 125 μM is incubated in distilled water or Tris-buffered saline (pH 7.4) with non-anticoagulant heparin, a heparin-like molecule, or fragments thereof, at 37° C. for at least 3 to 5 days, but preferably 1 week, within a range of Aβ:non-anticoagulant heparin molar ratios from 1:0.5 to 1:100, including 1:0.5, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In a preferred embodiment congophilic maltese-cross compact amyloid plaques are formed utilizing Aβ 1–40 with heparan sulfate. In this preferred embodiment Aβ 1–40 is incubated in distilled water or Tris-buffered saline (pH 7.4) with heparan sulfate at 37° C. for at least 3 to 5 days, but preferably 1 week, within a range of Aβ:heparan sulfate weight ratios from 1:1 to 1:100, including 1: 1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:8 or 1:16.

Another object of the present invention is to provide methods to form congophilic maltese-cross compact amyloid plaques in vitro, using Aβ and sulfated macromolecules or portions thereof. Such sulfated macromolecules included any and all compounds which contain at least one, but preferably more than two sulfated moieties. Such compounds include, but are not limited to dextran sulfate, pentosan polysulfate, polyvinyl sulphonate, Congo red, poly(vinylsulfonic acid), poly(2-acylamido-2-methyl-1-propanesulfonic acid), poly(2-acrylamido-2-methyl-1-propanesulfonic acid-co-acrylonitrile), poly(2-acrylamido-2-methyl-1-propanesulfonic acid-co-sterene), poly(vinylsulfonic acid), poly(vinylsulfuric acid), poly(sodium 4styrenesulfonic acid), a sulfonic acid derivative of poly(acrylic acid), a sulfonic acid derivative of poly(methyl acrylate), a sulfonic acid derivative of poly(methyl methacrylate), a sulfonate derivative of poly(vinyl alcohol), sulfonated sucrose, sucrose octasulfonate, 5-deoxy-1,2-O-isopropylidene-alpha-D-xylofuranose-5-sulfonic acid, ethanesulfonic acid, sucrose octasulfate, ethyl sulfuric acid, 2-aminoethan-1-ol sulfuric acid, 1,2-ethenediol disulfuric acid, 1-propanesulfonic acid, 1,2-ethanedisulfonic acid, 1-propanol sulfuric acid, 1,2-ethanediol disulfuric acid, 1,3-propanediol disulfuric acid, 1,4-butanediol disulfuric acid, 1,5-pentanediol disulfuric acid, 1,4-butanediol monosulfuric acid, 1,3-propanedisulfonic acid, 1,4-butanediol disulfuric acid, 1,4-butanedisulfonic acid, 1,5-pentanedisulfonic acid, taurine, 3-(N-morpholino) propanesulfonic acid, 2-aminoethanesulfonic acid, tetrahydrothiophene-1,1-dioxide-3,4-disulfonic acid, 4-hydroxybutane-1-sulfonic acid, 1-butanesulfonic acid, 1-decanesulfonic acid, 2-propanesulfonic acid, 3-pentanesulfonic acid, 4-hepanesulfonic acid, 1-decanesulfonic acid, 3-amino-1-propanesulfonic acid, 3-hydroxypropanesulfonic acid sulfate, 1,7-dihydroxy-4-heptanesulfonic acid, 2-[(4-pyridinyl) amido]ethanesulfonic acid, 3-(N-morpholino)propanesulfonic acid, tetrahydrothiophene-1,1-dioxide-3,4-disulfonic acid, 1,3-benzenedisulfonic acid, 2,5-dimethoxy-1,4-benzenedisulfonic acid, 4-amino-3-hydroxy-1-naphthalenesulfonic acid, 3,4,diamino-1-naphthalenesulfonic acid, 1-7-dihydroxy-4-heptanesulfonic acid, 2-hydroxymethyl-1,3-propanediol disulfuric acid, 2-hydroxymethyl-2-methyl-1,3-propanediol disulfuric acid, 1,3-cyclohexanediol disulfuric acid, 2,3,4,3',4'-sucrose pentasulfuric acid, 2-hydroxyethylsulfamic acid sulfuric acid, 3-hydroxypropylsulfamic acid sulfuric acid, 1,3,5,7-heptane tetrasulfuric acid, 1,3,5,7,9-nonane pentasulfuric acid, 2-aminoethanesulfonic acid (taurine), cysteic acid (3-sulfoalanine or alpha-amino-β-sulfopropionic acid), methyl-alpha-D-glucopyranoside 2,3,-disulfate, 1,3-cyclohexanediol disulfate, 1,3,5-heptanetriol trisulfate, 2-hydroxymethyl-1,3-propanediol trisulfate, 2-hydroxymethyl-2-methyl-1,3-propanediol trisulfate, 1,3,5,7-heptanetetraol tetrasulfate, 1,3,5,7,9-nonane pentasulfate, 2-amino-2-hydroxymethyl-1,3-propanediol trisulfate, 2-benzyloxy-1, 3-propanediol disulfate, 3-hydroxypropylsulfamic acid sulfate, 2,2'-iminoethanol disulfate, N,N-bis(2-hydroxyethyl)sulfamic acid disulfate, 3-(n-morpholino)propanesulfuric acid, tetrahydrothiophene-1,1-dioxide-3,4-diol disulfuric acid, methyl 4,6-O-benzylidene-alpha-D-glucopyranoside 2,3-disulfate, 2,3,4,3'4'-sucrose pentasulfate, 1,3:4,6di-O-benzylidene-D-mannitol 2,5-disulfate, D-mannitol 2,5-disulfate, 2,5-di-O-benzyl-D-mannitol tetrasulfate, trehalose octasulfate, octasodium salt, sucrose octasulfate, octasodium slat, methyl alpha-D-glucopyranoside, tetrasodium salt, methyl β-D-lactoside heptasulfate, heptasodium salt, sodium ethanesulfonate, sodium 1-propanesulfonate, 1-pentanesulfonic acid, sodium salt, and pharmaceutically acceptable salts thereof.

In a preferred embodiment congophilic maltese-cross compact amyloid plaques are formed utilizing Aβ 1–40 with dextran sulfate. In this preferred embodiment Aβ 1–40 at 25 μM or 125 μM is incubated in distilled water or Tris-buffered saline (pH 7.4) with dextran sulfate at 37° C. for at least 3 to 5 days, but preferably 1 week, within a range of Aβ:dextran sulfate molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In another preferred embodiment congophilic maltese-cross compact amyloid plaques are formed utilizing Aβ 1–40 with pentosan polysulfate. In this preferred embodiment Aβ 1–40 at 25 μM or 125 μM is incubated in distilled water or Tris-buffered saline (pH 7.4) with pentosan polysulfate at 37° C. for at least 3 to 5 days, but preferably 1 week, within a range of Aβ:pentosan polysulfate molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In another preferred embodiment congophilic maltese-cross compact amyloid plaques are formed utilizing Aβ 1–40 with polyvinyl sulphonate. In this preferred embodiment Aβ 1–40 is incubated in distilled water or Tris-buffered saline (pH 7.4) with polyvinyl sulphonate at 37° C. for at least 3 to 5 days, but preferably 1 week, within a range of Aβ:polyvinyl sulphonate weight ratios from 1:3 to 1:100, including 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:20 and 1:40.

Another object of the present invention is to provide methods to form congophilic maltese-cross compact amyloid plaques in vitro, using Aβ 1–40 and anionic macromolecules or portions thereof. Such anionic macromolecules included any and all compounds which contain at least one, but preferably more than two anionic groups. Such anionic groups include, but are not limited to sulfate groups, sulfonate groups, sulfonate ester groups, cyclic sulfates groups, sultone groups, tetrazole groups [including, but not limited to, 3-(1H-tetrazol-5-yl)-9H-thioxanthen-9-one, 10,10-dioxide, 5,5-dithiobis(1-phenyltetrazole), 1H-tetrazole, 5-phenyl-1H-tetrazole, and 5-(2-aminoethanoic acid)-1H-tetrazole, and pharmacological acceptable salts thereof], sulfamates, phosphonates, phosphates, and carboxylates, or a combination thereof (i.e. combination of different anionic groups, e.g. sulfates and sulfonates).

Another object of the present invention is to provide methods to form congophilic maltese-cross compact amyloid plaques in vitro, using Aβ with a ~220 kDa heparan sulfate proteoglycan (HSPG), or portions thereof, isolated from the Engelbreth-Holm-Swarm (EHS) tumor and/or other tissues including, but not limited to, brain and kidney. In a preferred embodiment such compact amyloid plaque formation is achieved by the co-incubation of Aβ 1–40 with a ~220 kDa HSPG following incubation at 37° C. for 1 week, and under the appropriate Aβ:~220 kDa HSPG weight and/or molar ratios as described herein. In such a preferred embodiment Aβ 1–40 is incubated in distilled water or Tris-buffered saline (pH 7.4) with the ~220 kDa HSPG at 37° C. for at least 3 to 5 days, but preferably 1 week, within a range of Aβ:~220 kDa weight ratios from 50:1 to 1:100, including 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 5:1.

Yet another object of the present invention is to provide methods to form congophilic maltese-cross compact amyloid plaques in vitro, using Aβ with sulfated PGs and sulfated GAGs or sulfated macromolecules, or portions thereof. In a preferred embodiment Aβ 1–40 with perlecan (at the appropriate Aβ:perlecan molar and/or weight ratios as described herein) is incubated at 37° C. for 1 week in the presence of sulfated GAGs or sulfated macromolecules (at the appropriate Aβ:sulfated GAG or sulfated macromolecule ratios as described herein). Sulfated GAGs or sulfated macromolecules for such congophilic maltese-cross compact amyloid is described above. In a preferred embodiment Aβ 1–40 with perlecan and dextran sulfate is incubated at 37° C. for 1 week at the appropriate Aβ:perlecan:dextran sulfate weight and/or molar ratios as described herein. In such a preferred embodiment, 25 μM or 125 μM of Aβ 1–40 is incubated with perlecan (assuming a molecular weight for perlecan of 800,000) in distilled water or Tris-buffered saline at 37° C. for at least 3 to 5 days, but preferably 1 week, within a range of Aβ:perlecan molar ratios from 50:1 to 500:1, including Aβ:perlecan molar ratios of 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 155:1, 160:1, 165:1, 170:1, 175:1, 180:1, 185:1, 190:1, 195:1, 200:1, 205:1, 210:1, 215:1, 220:1, 225:1, 230:1, 235:1, 240:1, 245:1, 250:1, 255:1, 260:1, 265:1, 270:1, 275:1, 280:1, 285:1, 290:1, 295:1, 300:1, 305:1, 310:1, 315:1, 320:1, 325:1, 330:1, 335:1, 340:1, 345:1, 350:1, 355:1, 360:1, 365:1, 370:1, 375:1, 380:1, 385:1, 390:1, 395:1, 400:1, 405:1, 410:1, 415:1, 420:1, 425:1, 430:1, 435:1, 440:1, 445:1, 450:1, 455:1, 460:1, 465:1, 470:1, 475:1, 480:1, 485:1, 490:1, 495:1 and 500:1, but preferably 200:1 and 250:1, and within a range of Aβ:dextran sulfate molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In another preferred embodiment, Aβ 1–40 is incubated with perlecan in distilled water or Tris-buffered saline at 37° C. for at least 3 to 5 days, but preferably 1 week, within a range of Aβ:perlecan weight ratios from 1:0.4–1:100, including Aβ:perlecan weight ratios of 1:0.4, 1:0.5, 1:0.8, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:1 and 1:0.8., and within a range of Aβ:dextran sulfate molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In yet another preferred embodiment Aβ 1–40 with perlecan and pentosan polysulfate is incubated at 37° C. for 1 week at the appropriate Aβ:perlecan:pentosan polysulfate weight and/or molar ratios as described herein. In a preferred embodiment Aβ 1–40 with perlecan and pentosan polysulfate is incubated at 37° C. for 1 week at the appropriate Aβ:perlecan:pentosan polysulfate weight and/or molar ratios as described herein. In such a preferred embodiment, 25 μM or 125 μM of Aβ 1–40 is incubated with perlecan (assuming a molecular weight for perlecan of 800,000) in distilled water or Tris-buffered saline at 37° C. for at least 3 to 5 days, but preferably 1 week, within a range of Aβ:perlecan molar ratios from 50:1 to 500:1, including Aβ:perlecan molar ratios of 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 155:1, 160:1, 165:1, 170:1, 175:1, 180:1, 185:1, 190:1, 195:1, 200:1, 205:1, 210:1, 215:1, 220:1, 225:1, 230:1, 235:1, 240:1, 245:1, 250:1, 255:1, 260:1, 265:1, 270:1, 275:1, 280:1, 285:1, 290:1, 295:1, 300:1, 305:1, 310:1, 315:1, 320:1, 325:1, 330:1, 335:1, 340:1, 345:1, 350:1, 355:1, 360:1, 365:1, 370:1, 375:1, 380:1, 385:1, 390:1, 395:1, 400:1, 405:1, 410:1, 415:1, 420:1, 425:1, 430:1, 435:1, 440:1, 445:1, 450:1, 455:1, 460:1, 465:1, 470:1, 475:1, 480:1, 485:1, 490:1, 495:1 and 500:1, but preferably 200:1 and 250:1, and within a range of Aβ:pentosan polysulfate molar ratios from 1:3 to 1:100, including 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In another preferred embodiment, Aβ 1–40 is incubated with perlecan in distilled water or Tris-buffered saline at 37° C. for at least 3 to 5 days, but preferably 1 week, within a range of Aβ:perlecan weight ratios from 1:0.4–1:100, including Aβ:perlecan weight ratios of 1:0.4, 1:0.5, 1:0.8, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:1 and 1:0.8., and within a range of Aβ:pentosan polysulfate molar ratios from 1:3 to 1:100, including 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In yet another preferred embodiment, Aβ 1–40 with perlecan and chondroitin-4-sulfate is incubated at 37° C. for 1 week at the appropriate Aβ:perlecan:chondroitin-4-sulfate weight and/or molar ratios as described herein. In such a preferred embodiment, 25 μM or 125 μM of Aβ 1–40 is incubated with perlecan (assuming a molecular weight for perlecan of 800,000) in distilled water or Tris-buffered saline at 37° C. for at least 3 to 5 days, but preferably 1 week, within a range of Aβ:perlecan molar ratios from 50:1 to 500:1, including Aβ:perlecan molar ratios of 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 155:1, 160:1, 165:1, 170:1, 175:1, 180:1, 185:1, 190:1, 195:1, 200:1, 205:1, 210:1, 215:1, 220:1, 225:1, 230:1, 235:1, 240:1, 245:1, 250:1, 255:1, 260:1, 265:1, 270:1, 275:1, 280:1, 285:1, 290:1, 295:1, 300:1, 305:1, 310:1, 315:1, 320:1, 325:1, 330:1, 335:1, 340:1, 345:1, 350:1, 355:1, 360:1, 365:1, 370:1, 375:1, 380:1, 385:1, 390:1, 395:1, 400:1, 405:1, 410:1, 415:1, 420:1, 425:1, 430:1, 435:1, 440:1, 445:1, 450:1, 455:1, 460:1, 465:1, 470:1, 475:1, 480:1, 485:1, 490:1, 495:1 and 500:1, but preferably 200:1 and 250:1, and within a range of Aβ:chondroitin-4-sulfate molar ratios from 1:3 to 1:100, including 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

Another object of the present invention is to provide methods for the in vitro formation of compact amyloid plaques which have similar characteristics to compact amyloid plaques in human prion diseases including Creutzfeldt-Jakob disease, Gerstmann-Struassler syndrome and kuru. Such characteristics of these plaques include, but are not limited to a) a spherical or compact shape, b) a maltese-cross pattern of congophilia following staining with Congo red and viewed under polarized light, c) staining with Thioflavin S, d) a spherical and/or "amyloid star" appearance when viewed by electron microscopy, e) a spherical or compact in shape (with plaques 10–40 μM in diameter) when viewed by scanning electron microscopy.

Another object of the present invention is to provide methods to form congophilic maltese-cross, compact amyloid plaques in vitro, using prion protein (PrP) and sulfated proteoglycans (PGs), or portions thereof. Such sulfated PGs include, but are not limited to, PGs which contain glycosaminoglycans (GAGs) of the heparan sulfate, dermatan sulfate, chondroitin sulfate, or keratan sulfate class. These PGs include, but are not limited to, perlecan, ~220 kDa HSPG (as described herein), glypican, cerebroglycan, aggrecan, synaptoglycan (SV2PG), syndecan, N-syndecan (i.e. syndecan-3), syndecan-1, syndecan-4, neurocan, phosphacan, decorin, biglycan, versican, amphiglycan, lumican, PG-M, PG-M (3), agrin, betaglycan, claustrin, brevican, appican, epican, and neuroglycan-C, or fragments thereof.

In a preferred embodiment such compact amyloid plaque formation is achieved by the co-incubation of PrP ($M_r$=27,000) with perlecan following incubation in distilled water or Tris-buffered saline (pH 7.4) at 37° C. for 1 week, and under the appropriate PrP:perlecan weight and/or molar ratios as described herein. In a preferred embodiment, 1 mg of PrP is dissolved in 1 ml of double distilled water or Tris-buffered saline (pH 7.4) to produce a stock solution (37 µM) of 1 mg/ml. 25 µl of the PrP stock solution is then added to a microcentrifuge tube containing 20 µg of lyophilized perlecan (isolated from the Engelbreth-Holm-Swarm tumor as described in Castillo et al, *J. Biochem.* 120:433–444, 1996), and then made up to a final volume of 250 µl, and incubated for 1 week at 37° C. In this preferred embodiment, the PrP:perlecan molar ratio is 37:1, and the PrP:perlecan weight ratio is 1:0.8. In other preferred embodiments, 3.7 µM of PrP is incubated in distilled water or Tris-buffered saline (pH 7.4) with 125 nM of perlecan, or 18.5 µM of PrP is incubated in distilled water or Tris-buffered saline (pH 7.4) with 0.625 µM of perlecan. In these latter two preferred embodiments, the PrP:perlecan molar ratio is 30:1 and the PrP:perlecan weight ratio is 1:1.

In other preferred embodiments to produce compact amyloid plaque formation, PrP is incubated with perlecan (assuming a molecular weight for perlecan of 800,000) in distilled water or Tris-buffered saline at 37° C. for at least 3 to 5 days, but preferably 1 week, within a range of PrP:perlecan molar ratios from 10:1 to 500:1, including PrP:perlecan molar ratios of 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 155:1, 160:1, 165:1, 170:1, 175:1, 180:1, 185:1, 190:1, 195:1, 200:1, 205:1, 210:1, 215:1, 220:1, 225:1, 230:1, 235:1, 240:1, 245:1, 250:1, 255:1, 260:1, 265:1, 270:1, 275:1, 280:1, 285:1, 290:1, 295:1, 300:1, 305:1, 310:1, 315:1, 320:1, 325:1, 330:1, 335:1, 340:1, 345:1, 350:1, 355:1, 360:1, 365:1, 370:1, 375:1, 380:1, 385:1, 390:1, 395:1, 400:1, 405:1, 410:1, 415:1, 420:1, 425:1, 430:1, 435:1, 440:1, 445:1, 450:1, 455:1, 460:1, 465:1, 470:1, 475:1, 480:1, 485:1, 490:1, 495:1 and 500:1, but preferably 30:1 and 37:1.

In other preferred embodiments to produce compact amyloid plaque formation, PrP is incubated with perlecan in distilled water or Tris-buffered saline at 37° C. for at least 3 to 5 days, but preferably 1 week, within a range of PrP:perlecan weight ratios from 1:0.4–1:100, including PrP:perlecan weight ratios of 1:0.4, 1:0.5, 1:0.8, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:1 and 1:0.8.

Another object of the present invention is to provide methods to form congophilic maltese-cross compact amyloid plaques in vitro, using PrP and GAGs or portions thereof. Such GAGs include but are not limited to heparan sulfate, heparin, dermatan sulfate, chondroitin-4-sulfate, chondroitin-6-sulfate, keratan sulfate, and/or hyaluronic acid. In a preferred embodiment such compact amyloid plaque formation is achieved by the co-incubation of PrP with heparin or PrP with heparan sulfate following incubation at 37° C. for 1 week, and under the appropriate PrP:heparin/heparan sulfate weight and/or molar ratios as described herein.

In a preferred embodiment congophilic maltese-cross compact amyloid plaques are formed utilizing PrP with heparin. In this preferred embodiment PrP at 3.7 µM or 18.5 µM is incubated in distilled water or Tris-buffered saline (pH 7.4) with heparin at 37° C. for at least 3 to 5 days, but preferably 1 week, within a range of PrP:heparin molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In a preferred embodiment congophilic maltese-cross compact amyloid plaques are formed utilizing PrP with heparan sulfate. In this preferred embodiment PrP is incubated in distilled water or Tris-buffered saline (pH 7.4) with heparan sulfate at 37° C. for at least 3 to 5 days, but preferably 1 week, within a range of PrP:heparan sulfate weight ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:8 or 1:16.

Another object of the present invention is to provide methods to form congophilic maltese-cross compact amyloid plaques in vitro, using PrP and sulfated macromolecules or portions thereof. Such sulfated macromolecules included any and all compounds which contain at least one, but preferably more than two sulfated moieties. Such compounds include, but are not limited to dextran sulfate, pentosan polysulfate, polyvinyl sulphonate, Congo red, poly (vinylsulfonic acid), poly(2-acylamido-2-methyl-1-propanesulfonic acid), poly(2-acrylamido-2-methyl-1-propanesulfonic acid-co-acrylonitrile), poly(2-acrylamido-2-methyl-1-propanesulfonic acid-co-sterene), poly (vinylsulfonic acid), poly(vinylsulfuric acid), poly(sodium 4-styrenesulfonic acid), a sulfonic acid derivative of poly (acrylic acid), a sulfonic acid derivative of poly(methyl acrylate), a sulfonic acid derivative of poly(methyl methacrylate), a sulfonate derivative of poly(vinyl alcohol), sulfonated sucrose, sucrose octasulfonate, 5-doxy-1,2-O-isopropylidene-alpha-D-xylofuranose-5-sulfonic acid, ethanesulfonic acid, sucrose octasulfate, ethyl sulfuric acid, 2-aminoethan-1-ol sulfuric acid, 1,2-ethenediol disulfuric acid, 1-propanesulfonic acid, 1,2-ethanedisulfonic acid, 1-propanol sulfuric acid, 1,2-ethanediol disulfuric acid, 1,3-propanediol disulfuric acid, 1,4-butanediol disulfuric acid, 1,5-pentanediol disulfuric acid, 1,4-butanediol monosulfuric acid, 1,3-propanedisulfonic acid, 1,4-butanediol disulfuric acid, 1,4-butanedisulfonic acid, 1,5-pentanedisulfonic acid, taurine, 3-(N-morpholino) propanesulfonic acid, 2-aminoethanesulfonic acid, tetrahydrothiophene-1,1-dioxide-3,4-disulfonic acid, 4-hydroxybutane-1-sulfonic acid, 1-butanesulfonic acid, 1-decanesulfonic acid, 2-propanesulfonic acid, 3-pentanesulfonic acid, 4-hepanesulfonic acid, 1-decanesulfonic acid, 3-amino-1-propanesulfonic acid, 3-hydroxypropanesulfonic acid sulfate, 1,7-dihydroxy-4-heptanesulfonic acid, 2-[(4-pyridinyl) amido]ethanesulfonic acid, 3-(N-morpholino)propanesulfonic acid, tetrahydrothiophene-1,1-dioxide-3,4-disulfonic acid, 1,3-benzenedisulfonic acid, 2,5-dimethoxy-1,4-benzenedisulfonic acid, 4-amino-3-hydroxy-1-naphthalenesulfonic acid, 3,4,diamino-1-naphthalenesulfonic acid, 1-7-dihydroxy-4-heptanesulfonic acid, 2-hydroxymethyl-1,3-propanediol disulfuric acid, 2-hydroxymethyl-2-methyl-1,3-propanediol disulfuric acid, 1,3-cyclohexanediol disulfuric acid, 2,3,4,3',4'-sucrose pentasulfuric acid, 2-hydroxyethylsulfamic acid sulfuric acid, 3-hydroxypropylsulfamic acid sulfuric acid, 1,3,5,7-heptane tetrasulfuric acid, 1,3,5,7,9-nonane pentasulfuric acid, 2-aminoethanesulfonic acid (taurine), cysteic acid (3sulfoalanine or alpha-amino-B-sulfopropionic acid), methyl-alpha -D-glucopyranoside 2,3,-disulfate, 1,3-cyclohexanediol disulfate, 1,3,5-heptanetriol trisulfate, 2-hydroxymethyl-1,3-propanediol trisulfate, 2-hydroxymethyl -2-methyl-1,3-propanediol trisulfate, 1,3,5,7-heptanetetraol tetrasulfate, 1,3,5,7,9-nonane pentasulfate, 2-amino-2-hydroxymethyl-1,3-propanediol trisulfate, 2-benzyloxy-1,3-propanediol disulfate, 3-hydroxypropylsulfamic acid sulfate, 2,2'-iminoethanol disulfate, N,N-bis(2-hydroxyethyl)sulfamic acid disulfate, 3-(n-morpholino)propanesulfuric acid, tetrahydrothiophene-1,1-dioxide-3,4-diol disulfuric acid, methyl 4,6-O-benzylidene-alpha-D-glucopyranoside 2,3-disulfate, 2,3,4,3'4'-sucrose pentasulfate, 1,3:4,6-di-O-benzylidene-D-mannitol 2,5-disulfate, D-mannitol 2,5-disulfate, 2,5-di-O-benzyl-D-mannitol tetrasulfate, trehalose octasulfate, octasodium salt, sucrose octasulfate, octasodium slat, methyl alpha-D-glucopyranoside, tetrasodium salt, methyl β-D-lactoside heptasulfate, heptasodium salt, sodium ethanesulfonate, sodium 1-propanesulfonate, 1-pentanesulfonic acid, sodium salt, and pharmaceutically acceptable salts thereof.

In a preferred embodiment congophilic maltese-cross compact amyloid plaques are formed utilizing PrP with dextran sulfate. In this preferred embodiment PrP at 3.7 µM or 18.5 µM is incubated in distilled water or Tris-buffered saline (pH 7.4) with dextran sulfate at 37° C. for at least 3 to 5 days, but preferably 1 week, within a range of PrP:dextran sulfate molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In another preferred embodiment congophilic maltese-cross compact amyloid plaques are formed utilizing PrP with pentosan polysulfate. In this preferred embodiment PrP at 3.7 µM or 18.5 µM is incubated in distilled water or Tris-buffered saline (pH 7.4) with pentosan polysulfate at 37° C. for at least 3 to 5 days, but preferably 1 week, within a range of PrP:pentosan polysulfate molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In another preferred embodiment congophilic maltese-cross compact amyloid plaques are formed utilizing PrP with polyvinyl sulphonate. In this preferred embodiment PrP is incubated in distilled water or Tris-buffered saline (pH 7.4) with polyvinyl sulphonate at 37° C. for at least 3 to 5 days, but preferably 1 week, within a range of PrP:polyvinyl sulphonate weight ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:20 and 1:40.

Another object of the present invention is to provide methods to form congophilic maltese-cross compact amyloid plaques in vitro, using PrP and anionic macromolecules or portions thereof. Such anionic macromolecules included any and all compounds which contain at least one, but preferably more than two anionic groups. Such anionic groups include, but are not limited to sulfate groups, sulfonate groups, sulfonate ester groups, cyclic sulfates groups, sultone groups, tetrazole groups [including, but not limited to, 3-(1H-tetrazol-5-yl)-9H-thioxanthen-9-one, 10,10-dioxide, 5,5-dithiobis(1-phenyltetrazole), 1H-tetrazole, 5-phenyl-1H-tetrazole, and 5-(2-aminoethanoic acid)-1H-tetrazole, and pharmacological acceptable salts thereof], sulfamates, phosphonates, phosphates, and carboxylates, or a combination thereof (i.e. combination of different anionic groups, e.g. sulfates and sulfonates).

Another object of the present invention is to provide methods to form congophilic maltese-cross compact amyloid plaques in vitro, using PrP with a ~220 kDa heparan sulfate proteoglycan (HSPG) or portions thereof, isolated from the Engelbreth-Holm-Swarm (EHS) tumor, or other tissues, including but not limited to brain and kidney. In a preferred embodiment such compact amyloid plaque formation is achieved by the co-incubation of PrP with a ~220 kDa HSPG following incubation at 37° C. for 1 week, and under the appropriate PrP:~220 kDa HSPG weight and/or molar ratios as described herein. In such a preferred embodiment PrP is incubated in distilled water or Tris-buffered saline (pH 7.4) with ~220 kda at 37° C. for at least 3 to 5 days, but preferably 1 week, within a range of PrP:~220 kDa weight ratios from 50:1 to 1:100, including 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 5:1.

Yet another object of the present invention is to provide methods to form congophilic maltese-cross compact amyloid plaques in vitro, using PrP with sulfated PGs and sulfated GAGs or sulfated macromolecules. In a preferred embodiment PrP with perlecan (at the appropriate PrP:perlecan molar and/or weight ratios as described herein) is incubated at 37° C. for 1 week in the presence of sulfated GAGs or sulfated macromolecules (at the appropriate PrP:sulfated GAG or sulfated macromolecule ratios as described herein). Sulfated GAGs or sulfated macromolecules for such congophilic maltese-cross compact amyloid is described above. In such a preferred embodiment PrP with perlecan and dextran sulfate is incubated at 37° C. for 1 week at the appropriate PrP:perlecan:dextran sulfate weight and/or molar ratios as described herein. In such a preferred embodiment, 3.7 µM or 18.5 µM of PrP is incubated with perlecan (assuming a molecular weight for perlecan of 800,000) in distilled water or Tris-buffered saline at 37° C. for at least 3 to 5 days, but preferably 1 week, within a range of PrP:perlecan molar ratios from 10:1 to 500:1, including PrP:perlecan molar ratios of 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 155:1, 160:1, 165:1, 170:1, 175:1, 180:1, 185:1, 190:1, 195:1, 200:1, 205:1, 210:1, 215:1, 220:1, 225:1, 230:1, 235:1, 240:1, 245:1, 250:1, 255:1, 260:1, 265:1, 270:1, 275:1, 280:1, 285:1, 290:1, 295:1, 300:1, 305:1, 310:1, 315:1, 320:1, 325:1, 330:1, 335:1, 340:1, 345:1, 350:1, 355:1, 360:1, 365:1, 370:1, 375:1, 380:1, 385:1, 390:1, 395:1, 400:1, 405:1, 410:1, 415:1, 420:1, 425:1, 430:1, 435:1, 440:1, 445:1, 450:1, 455:1, 460:1, 465:1, 470:1, 475:1, 480:1, 485:1, 490:1, 495:1 and 500:1, but preferably 30:1 and 37:1, and within a range of PrP:dextran sulfate molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In another preferred embodiment, PrP is incubated with perlecan in distilled water or Tris-buffered saline at 37° C. for at least 3 to 5 days, but preferably 1 week, within a range of PrP:perlecan weight ratios from 1:0.4–1:100, including PrP:perlecan weight ratios of 1:0.4, 1:0.5, 1:0.8, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:1 and 1:0.8., and within a range of PrP:dextran sulfate molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In yet another preferred embodiment PrP with perlecan and pentosan polysulfate is incubated at 37° C. for 1 week at the appropriate PrP:perlecan:pentosan polysulfate weight and/or molar ratios as described herein. In a preferred embodiment PrP with perlecan and pentosan polysulfate is incubated at 37° C. for 1 week at the appropriate PrP:perlecan:pentosanpolysulfate weight and/or molar ratios as described herein. In such a preferred embodiment, 3.7 µM or 18.5 µM of PrP is incubated with perlecan (assuming a molecular weight for perlecan of 800,000) in distilled water or Tris-buffered saline at 37° C. for at least 3 to 5 days, but preferably 1 week, within a range of PrP:perlecan molar ratios from 10:1 to 500:1, including PrP:perlecan molar ratios of 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 155:1, 160:1, 165:1, 170:1, 175:1, 180:1, 185:1, 190:1, 195:1, 200:1, 205:1, 210:1, 215:1, 220:1, 225:1, 230:1, 235:1, 240:1, 245:1, 250:1, 255:1, 260:1, 265:1, 270:1, 275:1, 280:1, 285:1, 290:1, 295:1, 300:1, 305:1, 310:1, 315:1, 320:1, 325:1, 330:1, 335:1, 340:1, 345:1, 350:1, 355:1, 360:1, 365:1, 370:1, 375:1, 380:1, 385:1, 390:1, 395:1, 400:1, 405:1, 410:1, 415:1, 420:1, 425:1, 430:1, 435:1, 440:1, 445:1, 450:1, 455:1, 460:1, 465:1, 470:1, 475:1, 480:1, 485:1, 490:1, 495:1 and 500:1, but preferably 30:1 and 37:1, and within a range of PrP:pentosan polysulfate molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In another preferred embodiment, PrP is incubated with perlecan in distilled water or Tris-buffered saline at 37° C. for at least 3 to 5 days, but preferably 1 week, within a range of PrP:perlecan weight ratios from 1:0.4–1:100, including PrP:perlecan weight ratios of 1:0.4, 1:0.5, 1:0.8, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:1 and 1:0.8., and within a range of PrP:pentosan polysulfate molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In yet another preferred embodiment PrP with perlecan and chondroitin-4-sulfate is incubated at 37° C. for 1 week at the appropriate PrP:perlecan:chondroitin-4-sulfate weight and/or molar ratios as described herein. In such a preferred embodiment, 3.7 μM or 18.5 μM of PrP is incubated with perlecan (assuming a molecular weight for perlecan of 800,000) in distilled water or Tris-buffered saline at 37° C. for at least 3 to 5 days, but preferably 1 week, within a range of PrP:perlecan molar ratios from 10:1 to 500:1, including PrP:perlecan molar ratios of 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 155:1, 160:1, 165:1, 170:1, 175:1, 180:1, 185:1, 190:1, 195:1, 200:1, 205:1, 210:1, 215:1, 220:1, 225:1, 230:1, 235:1, 240:1, 245:1, 250:1, 255:1, 260:1, 265:1, 270:1, 275:1, 280:1, 285:1, 290:1, 295:1, 300:1, 305:1, 310:1, 315:1, 320:1, 325:1, 330:1, 335:1, 340:1, 345:1, 350:1, 355:1, 360:1, 365:1, 370:1, 375:1, 380:1, 385:1, 390:1, 395:1, 400:1, 405:1, 410:1, 415:1, 420:1, 425:1, 430:1, 435:1, 440:1, 445:1, 450:1, 455:1, 460:1, 465:1, 470:1, 475:1, 480:1, 485:1, 490:1, 495:1 and 500:1, but preferably 30:1 and 37:1, and within a range of PrP:chondroitin-4-sulfate molar ratios from 1:1 to 1:100, including 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

In another preferred embodiment, PrP is incubated with perlecan in distilled water or Tris-buffered saline at 37° C. for at least 3 to 5 days, but preferably 1 week, within a range of PrP:perlecan weight ratios from 1:0.4–1:100, including PrP:perlecan weight ratios of 1:0.4, 1:0.5, 1:0.8, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:1 and 1:0.8., and within a range of PrP:chondroitin-4-sulfate molar ratios from 1:3 to 1:100, including 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, but preferably 1:5.

Yet another object of the present invention is to utilize compact amyloid plaques produced as described herein for screening methods to identify anti-plaque therapeutic agents in vitro for the potential treatment of Alzheimer's disease or prion diseases. In a preferred embodiment such screening methods will utilize amyloid proteins (Aβ or PrP), PGs, sulfated GAGs and/or sulfated macromolecules that are radiolabelled. Appropriate labelling agents include, but are not limited to, a radiolabel, an enzyme label, a fluorescent label, a chemiluminescent label, or an antigen label. Such screening methods can be employed using liquid phase and/or solid phase assays as described herein and appropriate detection systems such as a scintillation counter, gamma counter, spectrophotometer, fluorometer or nephelometer.

In a preferred embodiment to utilize compact amyloid plaques produced herein for screening methods to identify anti-plaque therapeutic agents in vitro, agents which inhibit, disrupt or eliminate the congophilic maltese-cross spherical amyloid plaques can be identified utilizing polarization microscopy. In such preferred embodiments, amyloid plaque cores will first be formed in vitro which demonstrate a typical maltese-cross pattern following staining with Congo red and when viewed under polarized light. Following incubation with a test compound (at the appropriate dosage and incubation time to be determined empirically), amyloid plaque cores will be viewed under polarization microscopy to determine if a given compound or agent is capable of inhibition, disruption or elimination of the amyloid plaque structure such that there is a loss of congophilia and/or maltese-cross formation. Such compounds initially identified by such polarization microscopy techniques can be further analyzed in secondary or tertiary assays utilizing transmission and/or scanning electron microscopy methods to confirm plaque inhibition, disruption or elimination.

In yet another preferred embodiment to utilize compact amyloid plaques produced herein for screening methods to identify anti-plaque therapeutic agents in vitro, agents which inhibit, disrupt the structure (i.e. size and/or diameter) of the spherical amyloid plaques can be identified using methodologies involving a cell sorter. In such assays, compact spherical amyloid plaques formed in vitro can be placed through a cell sorter to determine the average diameter (and range of diameters) of such plaques. These plaques can then be incubated with a variety of compounds or agents (at a given dosage and incubation time to be determined empirically) and then be placed through the cell sorter again to determine if the given compound was effective in breaking apart to disrupting the size (and hence diameter) of such plaques.

Yet another object of the present invention is to provide new animal models which demonstrate congophilic maltese-cross compact amyloid plaques in vivo. Such methods will include, but are not limited to, the injection, infusion or placement by other means, of compact amyloid plaques formed in vitro, into brain or other tissues. Such animals will provide new means to study the effects of compact amyloid plaque deposition and persistence in vivo and will provide new means to test the effectiveness of anti-plaque therapeutics in animal models.

Yet another object of the present invention is to provide new animal models of Aβ-containing congophilic maltese-cross compact amyloid plaques in vivo. In a preferred embodiment, Aβ-containing compact amyloid plaques formed in vitro by the methods described herein will be injected, infused or placed by other means into the brains of animals. Such amyloid plaque models can be used to study the effects of amyloid plaque deposition and persistence in brain and will provide new methods to test the effectiveness of anti-plaque therapeutics in animal models. In addition, such models can be used to identify anti-plaque therapeutics for the treatment of Alzheimer's disease. Such amyloid plaque models can also be used to study the response of cells (i.e. their role in phagocytosis, degradation, metabolic changes) to the deposition and persistence of amyloid plaques in vivo.

Yet another object of the present invention is to provide new animal models of PrP-containing congophilic maltese-cross compact amyloid plaques in vivo. In a preferred embodiment, PrP-containing compact amyloid plaques formed in vitro by the methods described herein will be injected, infused or placed by other means into the brains of animals. Such amyloid plaque models can be used to study the effects of amyloid plaque deposition and persistence in brain and will provide new methods to test the effectiveness of anti-plaque therapeutics in animal models. In addition, such models can be used to identify anti-plaque therapeutics for the treatment of prion diseases, including Creutzfeldt-Jakob disease, Gerstmann-Straussler syndrome, kuru and animal scrapie.

DEFINITIONS

Figure 1A:
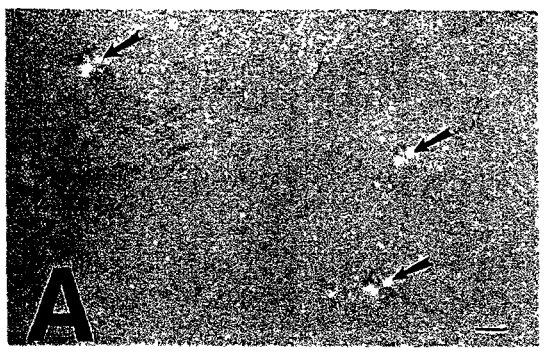
FIGS. 1A–1L are photomicrographs of the in vitro formation of congophilic maltese-cross spherical amyloid plaques by an embodiment of the inventive method.

The term "diffuse plaques" is used herein to refer to amyloid plaques in human Alzheimer's disease brain which are immunoreactive with a variety of different anti-Aβ antibodies but generally do not stain for fibrillar amyloid (i.e. Congo red, Thioflavin S) (Ikeda et al, *Lab. Invest.* 60:113–122, 1989; Verga et al, *Neurosc. Lett.* 105:294–299, 1989).

The term "neuritic plaques" is used herein to refer to plaques in human Alzheimer's disease brain which contain dystrophic neurites surrounding a spherical amyloid plaque core (Barcikowska et al, *Acta Neuronath.* 78:225–231, 1989; Ikeda et al, *Lab. Invest.* 60:113–122, 1989; Masliah et al, *J. Neuropath. Exp. Neurol.* 52:619–632, 1993). The amyloid cores within these plaques are Aβ immunopositive and stain with Congo red and Thioflavin S. In addition, the amyloid plaque cores within neuritic plaques are usually spherical and resemble a maltese-cross when stained with Congo red and viewed under polarized light (Ikeda et al, *Lab. Invest.* 60:113–122, 1989; Wisniewski et al, *Acta Neuropath.* 78:337–347, 1989; Schmidt et al, *Am. J. Path.* 147:503–515, 1995).

The term "compact" or "burned-out" plaques is used herein to refer to plaques in human Alzheimer's disease or prion disease brain that are generally believed to represent a more mature form of plaque formation (Wisniewski et al, *Acta Neuropath.* 78:337–347, 1989; Schmidt et al, *Am. J. Path.* 147:503–515, 1995; Dickson, *J. Neuropath. Exp. Neurol.* 56:321–339, 1997). These spherical plaques are Aβ or prion protein-immunopositive and stain with Congo red (also resembling a maltese-cross when viewed under polarized light) and Thioflavin S. "Compact" or "burned-out" plaques also demonstrate a maltese-cross pattern when stained with Congo red and viewed under polarized light.

The term "congophilia" is used herein to describe fibrillar amyloid deposits which demonstrate a red/apple-green birefringence when stained with Congo red and when viewed under polarized light. Congophilic deposits do not necessarily exhibit a maltese-cross pattern (see below for definition).

The term "maltese-cross" refers to spherical and compact amyloid plaques which when stained with Congo red and viewed under polarized light demonstrate a maltese-cross pattern (i.e. red color is 90 degrees to apple-green color). Upon rotation of the polarizer, a shift in colors of the plaque occurs such that the red color will change to apple-green, and the apple-green color will change to red (i.e. red/green birefringence"). The amyloid plaques formed in vitro as described in the present invention, the amyloid cores of neuritic plaques in human Alzheimer's disease brain, the "compact" or "burned-out" plaques in human Alzheimer's disease brain, and the amyloid plaques in cerebellum in human Creutzfeldt-Jakob disease, Gerstmann-Straussler syndrome and kuru all demonstrate a "maltese-cross" pattern, when stained with Congo red and viewed under polarized light.

The term "amyloid star" is used herein to refer to "compact" or "burned-out" amyloid plaques which resemble star-shaped deposits of amyloid when viewed by electron microscopy (Selkoe et al, *J. Neurochem.* 46:1820–1834, 1986; Snow et al, *Am. J. Path.* 133:456–463, 1988). The "amyloid star" appearance of the plaque is due to bundles of radiating amyloid fibrils appearing to emanate from the center of the plaque.

The term "induction" or "formation" is used herein to refer to compact amyloid plaques that are formed in vitro when incubated at 37° C. under the appropriate conditions. Gentle mixing of the incubation components is within the comtemplation of the invention as discussed in terms of induction or formation.

The term "anti-plaque therapeutics" is used herein to refer to compounds or drugs which are effective in a) directly dissolving, inhibiting or disrupting the architecture, staining characteristics or structure of the compact plaque, and/or b) inhibiting the detrimental effects (i.e. neurotoxicity) that the compact plaque may have on other cells (i.e. neurons), tissues or organs.

The term "beta-amyloid protein (Aβ 1–40)" refers to SEQ ID NO: 1, and may include all single or multiple amino acid substitutions that occur in human disease (such as Alzheimer's, where single amino acid substitutions in the Aβ 1–40 are known), or in species variation (such as rodent Aβ 1–40 which is known to have three amino acid differences in comparison to human Aβ 1–40).

BEST MODE OF CARRYING OUT THE INVENTION

The following examples, drawings and discussion are illustrative of embodiments of the invention and are not meant to limit the scope of the invention. The following sections are also provided by way of additional background to better appreciate the invention.

Alzheimer's Disease

Alzheimer's disease is the most common cause of dementia in middle and late life, and is manifested by progressive impairment of memory, language, visuospatial perceptions and behavior (*A Guide to the Understanding of Alzheimer's Disease and Related Disorders*, edited by Jorm, New York University Press, New York 1987). A diagnosis of probable Alzheimer's disease can be made on clinical criteria (usually by the exclusion of other diseases, memory tests etc), but a definite diagnosis requires the histological examination of specific abnormalities in the brain tissue usually obtained at autopsy.

In Alzheimer's disease, the parts of the brain essential for cognitive processes such as memory, attention, language, and reasoning degenerate, robbing victims of much that makes us human, including independence. In some inherited forms of Alzheimer's disease, on set is in middle age, but more commonly, symptoms appear from the mid-60's onward. Alzheimer's disease is characterized by the deposition and accumulation of a 39–43 amino acid peptide termed the beta-amyloid protein, Aβ or β/A4 (Glenner and Wong, *Biochem. Biophys. Res. Comm.* 120:885–890, 1984; Masters et al, *Proc. Natl. Acad. Sci. USA* 82:4245–4249, 1985; Husby et al, *Bull. WHO* 71:105–108, 1993). Aβ is derived from larger precursor proteins termed beta-amyloid precursor proteins (or βPPs) of which there are several alternatively spliced variants. The most abundant forms of the βPPs include proteins consisting of 695, 751 and 770 amino acids (Tanzi et al, *Nature* 331:528–530, 1988; Kitaguchi et al, *Nature* 331:530–532, 1988; Ponte, et al, *Nature* 331:525–528, 1988). The small Aβ peptide is a major component which makes up the amyloid deposits of neuritic "plaques" and in the walls of blood vessels known as cerebrovascular amyloid deposits) in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al, *Proc. Natl. Acad. Sci. USA* 83:4913–4917, 1986; Kosik et al, *Proc. Natl. Acad. Sci. USA* 83:4044–4048, 1986; Lee et al, *Science* 251:675–678, 1991). The pathological hallmarks of Alzheimer's disease is therefore the presence of "plaques" and "tangles", with amyloid being deposited in the central core of plaques and within the blood vessel walls. It is important to note that a so-called "normal aged brain" has some amyloid plaques and neurofibrillary tangles present. However, in comparison, an Alzheimer's disease brain shows an over abundance of plaques and tangles. Therefore, differentiation of an Alzheimer's disease brain from a normal brain from a diagnostic point of view is primarily based on quantitative assessment of "plaques" and "tangles".

In an Alzheimer's disease brain, there are usually thousands of neuritic plaques. The neuritic plaques are made up of extracellular deposits consisting of an amyloid core usually surrounded by enlarged axons and synaptic terminals, known as neurites, and abnormal dendritic processes, as well as variable numbers of infiltrating microglia and surrounding astrocytes. The neurofibrillary tangles present in the Alzheimer's disease brain mainly consist of tau protein, which is a microtubule-associated protein (Grundke-Iqbal et al, *Proc. Natl. Acad. Sci. USA* 83:4913–4917, 1986; Kosik et al, *Proc. Natl. Acad. Sci. USA* 83:4044–4048, 1986; Lee et al, *Science* 251:675–678, 1991). At the ultrastructural level, the tangle consists of paired helical filaments twisting like a ribbon, with a specific crossing over periodicity of 80 nanometers. In many instances within a neurofibrillary tangle, there are both paired helical filaments and straight filaments. In addition, the nerve cells will many times die, leaving the filaments behind. These tangles are known as "ghost tangles" since they are the filamentous remnants of the dead neuron.

The other major type of lesion found in the brain of an Alzheimer's disease patient is the accumulation of amyloid in the walls of blood vessels, both within the brain parenchyma and in the walls of the larger meningeal vessels which lie outside the brain. The amyloid deposits localized to the walls of blood vessels are referred to as cerebrovascular amyloid or congophilic angiopathy (Mandybur, *J. Neuropath. Exp. Neurol.* 45:79–90, 1986; Pardridge et al, *J. Neurochem.* 49:1394–1401, 1987).

In addition, Alzheimer's disease patients demonstrate neuronal loss and synaptic loss. Furthermore, these patients also exhibit loss of neurotransmitters such as acetylcholine. Tacrine, the first FDA approved drug for Alzheimer's disease is a cholinesterase inhibitor (Cutler and Sramek, *New Engl. J. Med.* 328:808–810, 1993). However, this drug has showed limited success, if any, in the cognitive improvement in Alzheimer's disease patients and initially had major side effects such as liver toxicity.

For many years there has been an ongoing scientific debate as to the importance of "amyloid" in Alzheimer's disease and whether the "plaques" and "tangles" characteristic of this disease, were a cause or merely the consequences of the disease. Recent studies during the last few years have now implicated that amyloid is indeed a causative factor for Alzheimer's disease and not merely an innocent bystander. The Alzheimer's disease Aβ protein in cell culture has been shown to cause degeneration of nerve cells within short periods of time (Pike et al, *Br. Res.* 563:311–314, 1991; *J. Neurochem.* 64:253–265, 1994). Studies suggest that it is the fibrillar structure, a characteristic of all amyloids, that is responsible for the neurotoxic effects. The Aβ has also been found to be neurotoxic in slice cultures of hippocampus (the major memory region affectedinAlzheimer's)(Harriganet al, *Neurobiol. Aging* 16:779–789, 1995) and induces nerve cell death in transgenic mice (Games et al, *Nature* 373:523–527, 1995; Hsiao et al, *Neuron* 15:1203–1218, 1995). In addition, injection of the Alzheimer's Aβ into rat brain causes memory impairment and neuronal dysfunction (Flood et al, *Proc. Natl. Acad. Sci. U.S.A.* 88:3363–3366, 1991; *Br. Res.*

663:271–276, 1994), two additional hallmarks of Alzheimer's disease. Probably, the most convincing evidence that amyloid (ie. beta-amyloid protein) is directly involved in the pathogenesis of Alzheimer's disease comes from genetic studies. It has been discovered that the production of Aβ can result from mutations in the gene encoding, its precursor, known as the beta-amyloid precursor protein (Van Broeckhoven et al, *Science* 248:1120–1122, 1990; *Europ. Neurol.* 35:8–19, 1995; Murrell et al, *Science* 254:97–99, 1991; Haass et al, *Nature Med.* 1:1291–1296, 1995). This precursor protein when normally processed usually only produces very little of the toxic Aβ. The identification of mutations in the amyloid precursor protein gene which causes familial, early onset Alzheimer's disease is the strongest argument that amyloid is central to the pathogenetic process underlying this disease. Four reported disease-causing mutations have now been discovered which demonstrate the importance of the beta-amyloid protein in causing familial Alzheimer's disease (reviewed in Hardy, *Nature Genet.* 1:233–234, 1992). All of these studies suggest that providing a drug to reduce, eliminate or prevent fibrillar Aβ formation, deposition, accumulation and/or persistence in the brains of human patients should be considered an effective therapeutic.

Diffuse Plaques, Neuritic Plaques and Compact ("Amyloid Star") Plaques

A variety of morphologically distinct types of Aβ-containing plaques have been described in the brains of Alzheimer's disease patients including diffuse plaques, neuritic plaques and compact ("amyloid star") plaques. Diffuse plaques have been considered early lesions because they are not associated with dystrophic neurites, are the predominant type of Aβ deposits in the non-demented elderly, and are the first lesions detected in young Down's syndrome brain (Yamaguchi et al, *Acta Neuropath.* 76:541–549, 1988; Allsop et al, *Neuropath. Appl. Neurobiol.* 15:531–542, 1989; Giaccone et al, *Neurosc. Lett.* 97:232–238, 1989; Ikeda et al, *Lab. Invest.* 61:133–137, 1989; Ikeda et al, *Lab. Invest.* 60:113–122, 1989; Mann et al, *Neuropath. Appl. Neurobiol.* 15:317–329, 1989; Wisniewski et al, *Acta Neuropath.* 78:337–347, 1989; Pappolla et al, *Am. J. Path.* 141:1151–1159, 1992; Lemere et al, *Neurobiol. Dis.* 3:16–32, 1996). Diffuse plaques are immunoreactive with a variety of different anti-Aβ antibodies but generally do not stain for fibrillar amyloid (i.e. red/green birefringence when stained with Congo red and viewed under polarized light, positive fluorescence with Thioflavin S)(Ikeda et al, *Lab. Invest.* 60:113–122, 1989; Verga et al, *Neurosc. Lett.* 105:294–299, 1989). In addition, diffuse plaques general do not contain dystrophic neurites or associated glia (Giaccone et al, *Neurosc. Lett.* 97:232–238, 1989; Wisniewski et al, *Acta Neuropath.* 78:337–347, 1989; Pappolla et al, *Am. J. Path.* 139:599–607, 1991). Neuritic plaques are considered more mature and contain dystrophic neurites surrounding a spherical amyloid plaque core (Barcikowska et al, *Acta Neuropath.* 78:225–231, 1989; Ikeda et al, *Lab Invest.* 60:113–122, 1989; Masliah et al, *J. Neuropath. Exp. Neurol.* 52:619–632, 1993). The amyloid cores within these plaques are Aβ immunopositive and stain with Congo red and Thioflavin S. In addition, the amyloid plaque cores within neuritic plaques are usually spherical and resemble a maltese-cross when stained with Congo red and viewed under polarized light (Ikeda et al, *Lab. Invest.* 60:113–122, 1989; Wisniewski et al, *Acta Neuropath.* 78:337–347, 1989; Schmidt et al, *Am. J. Path.* 147:503–515, 1995). The amyloid cores within neuritic plaques resemble "amyloid stars" when viewed by electron microscopy (Wisniewski et al, *Acta Neuropath.* 78:337–347, 1989). Compact amyloid cores (also referred to as "burnt-out" or "core" plaques) also resemble "amyloid stars" when viewed by electron microscopy (Selkoe et al, *J. Neurochem.* 46:1820–1834, 1986; Snow et al, *Am. J. Path.* 133:456–463, 1988), and are generally believed to represent a more mature form of plaque formation (Wisniewski et al, *Acta Neuropath.* 78:337–347, 1989; Schmidt et al, *Am. J. Path.* 147:503–515, 1995; Dickson, *J. Neuropath. Exp. Neurol.* 56:321–339, 1997). These spherical plaques are Aβ-immunopositive and stain with Congo red (also resembling a maltese-cross when viewed under polarized light) and Thioflavin S.

Compact "amyloid star" plaques are not only present in the brains of patients with Alzheimer's disease, but are also observed generally in the cerebellum of patients afflicted with so-called prion diseases, including Creutzfeldt-Jakob disease (Bockman et al, *N. Engl. J. Med.* 312:73–78, 1985; Kitamoto et al, *Ann. Neurol.* 20:204–208, 1986; Manuelidis, *J. Neuropath. Exp. Neuro.* 44:1–17, 1985; Brown et al, *Ann. Neurol.* 20:597–602, 1986), Gerstmann-Straussler syndrome (Tateishi et al, *Ann. Neurol.* 24:35–40, 1988; Hsiao et al, *Nature Gen.* 1:68–71, 1992) and kuru (Gajdusek, *Science* 197:943–960, 1977; Hashimoto et al, *Acta Neuropath.* 83:613–617, 1992). In these diseases, the amyloid protein is a 27–30 kDa protein referred to as the prion protein, PrP or PrP 27–30. These amyloid plaques also are spherical in shape, are immunopositive with anti-PrP antibodies, and stain with Congo red and Thioflavin S (indicative of fibrillar amyloid) (Perlman et al, *Neurology* 38:1249–1254, 1988). These compact plaques, as in human Alzheimer's disease, also demonstrate a maltese-cross pattern when stained with Congo red and viewed under polarized light.

Investigators have hypothesized that in Alzheimer's disease there is most likely a conversion from the diffuse plaque to the neuritic plaque to the compact plaque. However, the mechanism of this conversion and the essential components involved have never been discovered. In addition, since the genesis of neuritic plaque and compact plaque formation has not been well understood, no one has caused formation of such plaque deposits in vitro that are similar to those plaques found in the brains of patients with Alzheimer's disease and/or prion diseases. Such in vitro plaque formation may be used to evaluate and identify agents that may have unique anti-plaque therapeutic potential and may serve as new approaches for the treatment of Alzheimer's disease and/or prion diseases. In view of the present lack of knowledge about the development and progression of Alzheimer's disease and prion diseases, there is a need for compounds and assay techniques that can be employed to screen and identify potential agents that inhibit or disrupt the development of amyloid plaques. Such compounds and methods would be useful in assessing amyloid plaque formation associated with the onset and progression of Alzheimer's disease and prion diseases.

These and other objects are achieved by the present invention which has determined the mechanisms of compact congophilic maltese-cross amyloid plaque formation and the essential components required, and describes methods to consistently form such Alzheimer's plaques for their utilization in a number of different assay techniques to identify anti-plaque therapeutics. Perlecan (a specific heparan sulfate proteoglycan implicated in Alzheimer's disease and prion amyloidosis), a ~220 kDa HSPG, highly sulfated glycosaminoglycans (GAGs) (ie. heparin and heparan sulfate), and related sulfated GAG macromolecules (ie. dextran sulfate, pentosan sulfate, polyvinyl sulphonate) induced beta-amyloid protein (Aβ)(residues 1–40) to transform into amyloid plaque core deposits (at 37° C. within 3–5 days with the right mixture and concentration of components) in vitro that are virtually identical to compact amyloid plaques present in human Alzheimer's disease brain. The molar and weight ratios of Aβ (1–40) to other essential components (described above) were found to be critical for amyloid plaque core formation. The invention further relates to the use of in vitro artificial amyloid plaque cores as screening tools for the in vitro identification of Alzheimer's disease anti-plaque therapeutics.

FIG. 1 demonstrates the in vitro formation of congophilic maltese-cross spherical amyloid plaques by perlecan but not other amyloid plaque associated macromolecules known to be present in human Alzheimer's disease brain. In these studies, 25 μM of Aβ (1–40) was incubated in double distilled water or Tris-buffered saline for 1 week at 37° C. either alone (FIG. 1C), or in the presence of 100 nM of P component (FIG. 1D), alpha$_1$-antichymotrypsin (FIG. 1E), apoE (FIG. 1F), C1q (FIG. 1G), laminin (FIG. 1H), fibronectin (FIG. 1I), type IV collagen (FIG. 1J) or perlecan (FIGS. 1K and 1L). 5 μl aliquots of the incubation mixtures were air-dried on gelatin-coated slides, stained with Congo red and viewed under polarized light. Preincubation of perlecan with Aβ 1–40 for 1 week at 37° C. at a preferred Aβ:perlecan molar ratio of 250:1 (i.e. weight ratio of 1:0.8) induced the formation of congophilic maltese-cross spherical amyloid plaque-like deposits (FIGS. 1K and 1L). Similar amyloid plaque formation was observed using 125 μM Aβ (1–40) with 0.625 μM perlecan (i.e. Aβ:perlecan molar ratio of 200:1; Aβ:perlecan weight ratio of 1:1), but not with 125 μM Aβ (1–40) with 0.625 μM of other amyloid plaque co-components as listed above (not shown). The amyloid plaques induced by perlecan were virtually identical in morphology and staining characteristics (i.e. maltese-cross following staining with Congo red) to compact amyloid plaques in human Alzheimer's disease brain (Compare FIGS. 1K and 1L to FIG. 1A). Bar in FIGS. A, B and K=25 μm. FIGS. A, C and H are taken at the same magnification, as are FIGS. B, D–G and I–J.

FIG. 2 demonstrates the in vitro formation of congophilic and maltese-cross spherical amyloid plaques by highly sulfated glycosaminoglycans (i.e heparin and heparan sulfate) and related sulfated macromolecules (ie. dextran sulfate, pentosan polysulfate). In these studies, 25 μM of Aβ 1–40 was incubated in double distilled water or Tris-buffered saline (pH 7.4) for 1 week at 37° C. either alone (FIG. 2B), or in the presence of various amounts of heparin (FIG. 2C), heparan sulfate (FIG. 2D), dermatan sulfate (FIG. 2E), Congo red (FIG. 2F), pentosan polysulfate (FIG. 2G), or dextran sulfate (FIG. 2I). 5 μl aliquots of the incubation mixtures were air-dried on gelatin-coated slides, stained with Congo red and viewed under polarized light. Preliminary experiments determined an optimum Aβ:GAG/sulfated macromolecule ratio for compact amyloid plaque formation to be a 1:5 molar ratio for heparin, dextran sulfate and pentosan polysulfate and a 1:8 weight ratio for heparan sulfate, while maintaining Aβ 1–40 at 25 μM. Similar results as described above were obtained using 125 μM Aβ 1–40 in double distilled water. Preincubation of heparin, heparan sulfate, pentosan sulfate or dextran sulfate with Aβ 1–40 for 1 week at 37° C. at these same molar/weight ratios induced the formation of congophilic maltese-cross spherical amyloidplaque-like deposits (FIGS. 2C, 2D, 2G–2I). The amyloid plaques induced by these highly sulfated GAGs and related sulfated macromolecules were virtually identical to compact amyloid plaques in human Alzheimer's disease brain (Compare to FIG. 2A). Bar in FIGS. A, B and I=25 μm. FIGS. A, C, D and H are taken at the same magnification, as are FIGS. B and E.

FIG. 3 demonstrates the in vitro formation of congophilic and maltese-cross spherical amyloid plaques by polyvinyl sulphonate (PVS), and demonstrates how changes in the weight ratio of Aβ:PVS influences the potential for compact amyloid plaque formation. In these studies, 50 μg of Aβ 1–40 in double distilled water was incubated for 1 week at 37° C. in the presence of increasing amounts of PVS including 25 μg PVS (Aβ:PVS weight ratio of 2:1)(FIG. 3A), 50 μg PVS (Aβ:PVS weight ratio of 1:1) (FIG. 3B), 200 μg PVS (Aβ:PVS weight ratio of 1:4)(FIG. 3C), 250 μg PVS (Aβ:PVS weight ratio of 1:5)(FIG. 3D), 400 μg PVS (Aβ:PVS weight ratio of 1:8)(FIG. 3E), 500 μg PVS (Aβ:PVS weight ratio of 1:10)(FIG. 3F), 800 μg PVS (Aβ:PVS weight ratio of 1:16)(FIG. 3G), 2000 μg PVS (Aβ:PVS weight ratio of 1:40)(FIG. 3H), and 4000 μg PVS (Aβ:PVS weight ratio of 1:80)(FIG. 3I), in a total volume of 100 μl or 5 μl or 10 μl aliquots of the incubation mixtures were air-dried on gelatin-coated slides, stained with Congo red and viewed under polarized light. Congophilic maltese-cross spherical amyloid plaque formation was induced by PVS, but only when the Aβ:PVS weight ratio was 1:5 or greater. Optimum amyloid plaque core formation was observed with an Aβ:PVS weight ratio of 1:40 (FIG. 3H). Bars in FIGS. A and C=25 μm. FIGS. A, B, H and I are taken at the same magnification as are FIGS. C–G.

Figure 4A:
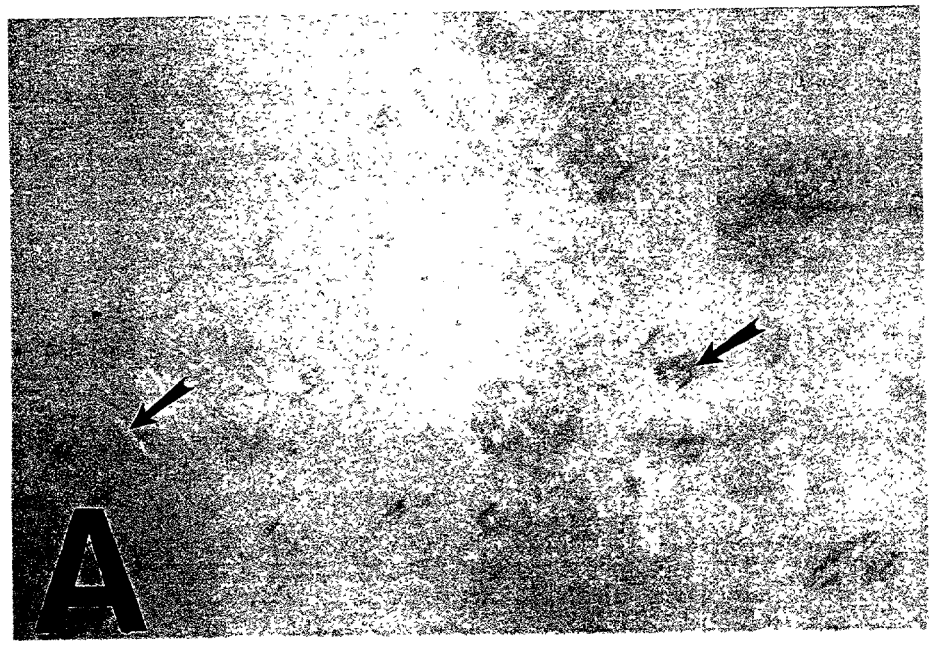
FIGS. 4A–4B are photomicrographs of the in vitro formation of congophilic maltese-cross compact amyloid plaque formation by another embodiment of the inventive method.
Figure 4B:
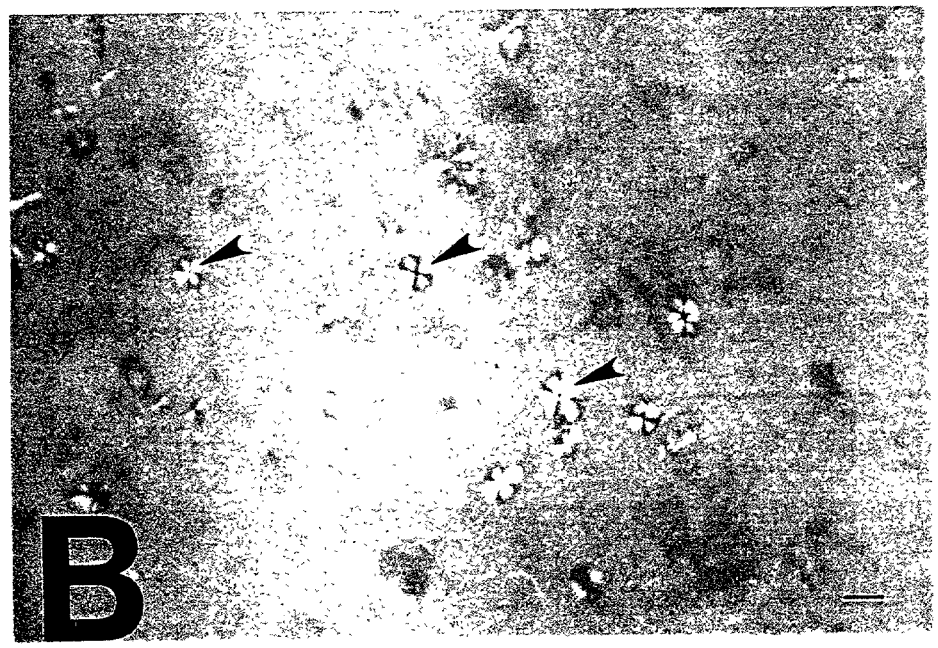

FIG. 4 demonstrates congophilic maltese-cross compact amyloid plaque formation induced by a ~220 kDa heparan sulfate proteoglycan (HSPG) isolated from Engelbreth-Holm-Swarm tumor. 50 μg of Aβ (1–40) in 100 μl Tris-buffered saline (pH 7.4) was incubated for 1 week at 37° C. either alone or in the presence of 10 μg of the ~220 kDa HSPG (Aβ:HSPG weight ratio of 5:1). FIG. 4A demonstrates irregular congophilic amyloid deposits (arrows) formed following a 1 week incubation of Aβ alone, with no apparent congophilic maltese-cross amyloid plaques formed. FIG. 4B demonstrates congophilic maltese-cross amyloid plaques (arrowheads) formed following a 1 week incubation of Aβ 1–40 plus 220 kDa HSPG. The amyloid plaques formed were identical to those compact plaques present in human Alzheimer's disease brain (see FIGS. 1A and 2A). FIGS. A and B are taken at same magnification, bar=25 μm.

Figure 5A:
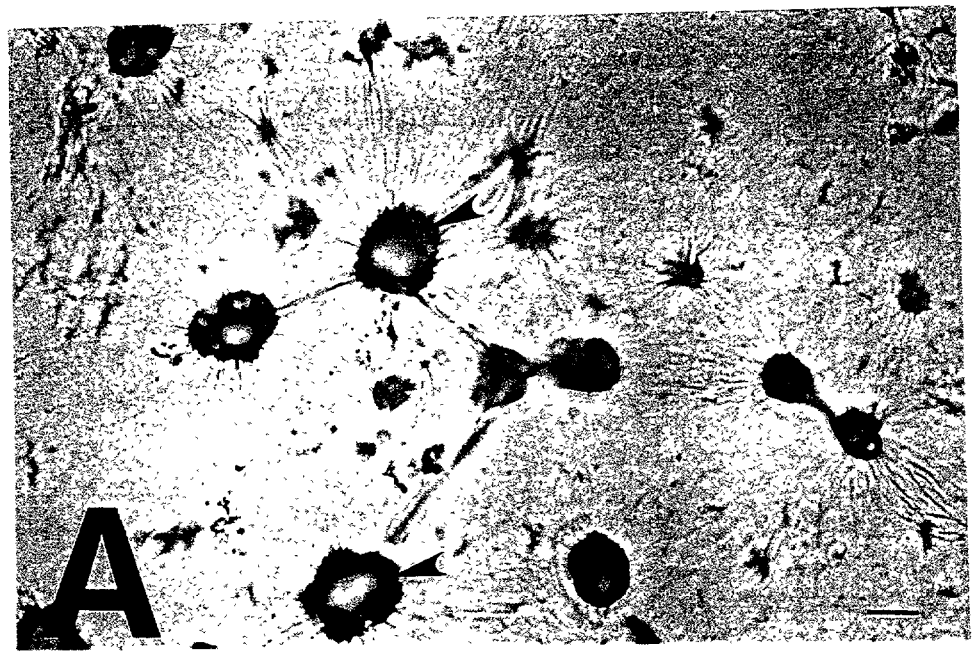
FIGS. 5A–5B are photomicrographs of in vitro formation of spherical amyloid plaques in alternate embodiment of the inventive method.
Figure 5B:
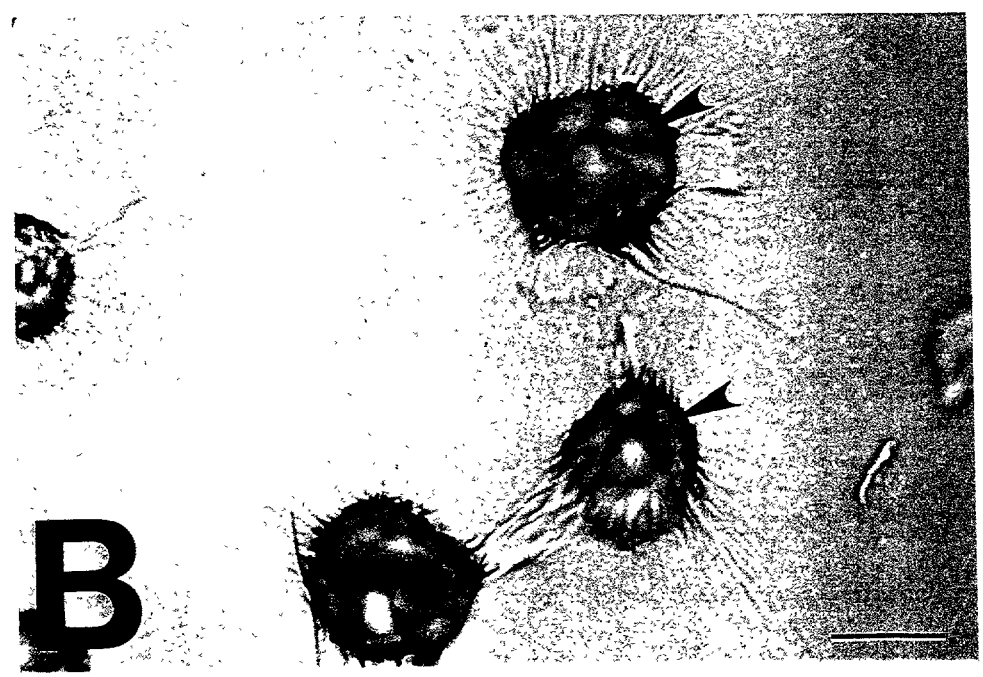
Figure 6A:
FIGS. 6A–6D are photomicrographs of spherical "amyloid star" formation induced by perlecan which is virtually identical to isolated amyloid plaque cores derived from human Alzheimer's disease brain as viewed by transmission electron microscopy.
Figure 6B:
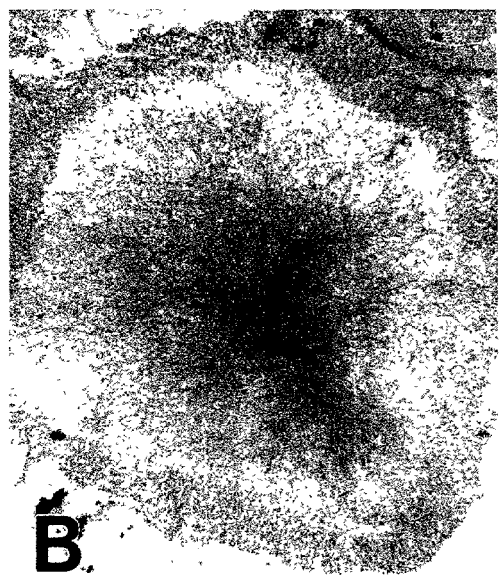
Figure 6C:
Figure 6D:
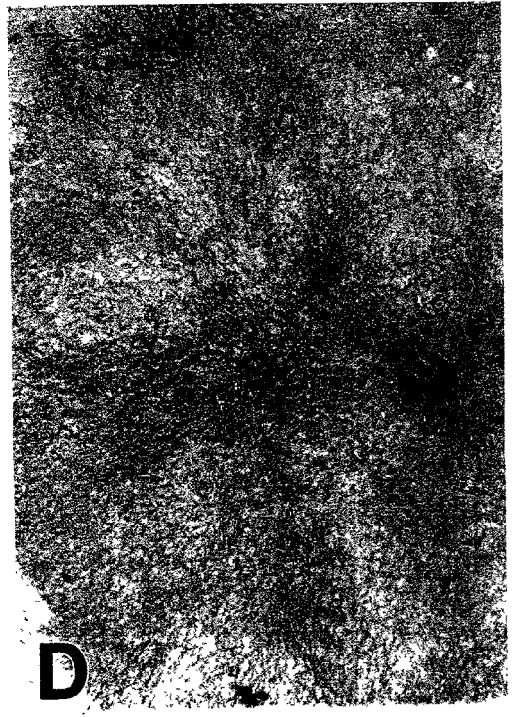

FIG. 5 demonstrates in vitro formation of spherical amyloid plaques induced by perlecan, as it appears in fixed in plastic. In this study, 125 μM of Aβ 1–40 was incubated in double distilled water for 1 week at 37° C. in the presence of 0.625 μM of perlecan (Aβ:perlecan molar ratio of 200:1; Aβ:perlecan weight ratio of 1:1). A 10 μl aliquot of the incubation mixture was then air-dried for one hour on plastic petri dishes, and then fixed in situ with 3% glutaraldehyde in 0.1M NaPO$_4$ buffer (pH 7.3) for 10 minutes. After rinsing three times with filtered distilled water, they were post-fixed for 10 minutes with 1% osmium tetroxide in distilled water for 10 minutes, rinsed as before and air-dried overnight. This figure demonstrates the amyloid plaque-like deposits induced by perlecan as it appears in plastic, and viewed with a phase-contrast light microscope. Perlecan induced Aβ to form spherical amyloid plaque deposits (FIGS. 5A and 5B, arrowheads) which represented amyloid plaque "stars" with radiating bundles of amyloid fibrils appearing to emanate from a central source. These plaques formed resemble amyloid plaque cores isolated from human Alzheimer's disease brain. Bar=25 μm.

FIG. 6 demonstrates spherical "amyloid star" formation induced by perlecan which is virtually identical to isolated amyloid plaque cores derived from human Alzheimer's disease brain as viewed by transmission electron microscopy. In this study, 125 µM of Aβ 1–40 was incubated in double distilled water for 1 week at 37° C. in the presence of 0.625 µM of perlecan (Aβ:perlecan molar ratio of 200:1; Aβ:perlecan weight ratio of 1:1). Amyloid plaque cores induced by perlecan (FIGS. 6C and 6D) formed "amyloid stars" with radiating bundles of amyloid fibrils appearing to emanate from a central source. Individual amyloid fibril diameters were determined to be 7–10 nm. These in vitro produced amyloid plaques were virtually identical to amyloid plaque cores isolated from human Alzheimer's disease brain (FIGS. 6A and 6C). Bar=2 µm. FIGS. A and B are of the same magnification as are FIGS. C and D.

FIG. 7 demonstrates amyloid plaque core formation induced by perlecan or dextran sulfate and viewed by scanning electron microscopy. In this study, 125 µM of Aβ 1–40 was incubated in double distilled water for 1 week at 37° C. either alone (FIG. 7B), or in the presence of 0.625 µM of perlecan (Aβ:perlecan molar ratio of 200:1)(FIGS. 7D and 7E) or dextran sulfate (Aβ:dextran sulfate molar ratio of 1:5). In addition, 0.625 µM of perlecan alone was incubated for 1 week at 37° C. (FIG. 7C). Amyloid plaque core formation was not observed following a 1 week incubation of Aβ (FIG. 7B) or perlecan (FIG. 7C) alone. However, compact amyloid plaque formation was induced by Aβ in the presence of perlecan (FIGS. 7D and 7E) or dextran sulfate (FIG. 7F). The shape and general morphology of the amyloid plaques induced by perlecan or dextran sulfate were similar to the shape and general morphology to isolated amyloid plaque cores derived from human Alzheimer's disease brain, as viewed by scanning electron microscopy. Magnifications are given at the bottom of each figure.

EXAMPLES

The following examples are provided to disclose in detail preferred embodiments of the in vitro formation of amyloid plaque cores induced by perlecan, highly sulfated GAGs and related sulfated macromolecules. However, it should not be construed that the invention is limited to these specific examples.

Example 1

Induction of Amyloid Plaque Core Formation by Perlecan but Not Other Amyloid Plaque Co-Components Various co-components known to be present in amyloid plaques in human Alzheimer's disease brain were tested for their potential ability to induce congophilic maltese-cross, compact amyloid plaque formation including P component (Coria et al, *Lab. Invest.* 58:454–458, 1988), alpha$_1$-antichymotrypsin (Abraham et al, *Cell* 52:487–501, 1988), ApoE (Nambaet al, *Brain Res.* 541:163–166, 1991; Strittmatteret al, *Proc. Natl. Acad. Sci. USA* 91:11183–11186, 1994; Strittmatter and Roses, *Proc. Natl. Acad. Sci. USA* 92:4725–4727, 1995), C1q (Eikelenboom et al, *Virchows Arch. B Cell Pathol.* 56:259–262, 1989; McGeer et al, *Can. J. Neurol. Sc.* 16:516–527, 1989; Rogers, *CNS drugs* 4:241–244, 1994), C3 (Eikelenboom et al, *Virchows Arch. B Cell Pathol.* 56:259–262, 1989; McGeer et al, *Can. J. Neurol. Sc.* 16:516–527, 1989; Rogers, *CNS drugs* 4:241–244, 1994), and perlecan (Snow et al, *Am. J. Path.* 133:456–463, 1988; Snow et al, *Am. J. Path.* 144:337–347, 1994). In addition, other basement membrane components (i.e. besides perlecan) including laminin (Murtomaki et al, *J. Neurosc. Res.* 32:261–273, 1992; Perlmutter and Chui, *Brain Res. Bull.* 24:677–686, 1990; Perlmutter et al, *Micro. Res. Tech.* 28:204–215, 1994), fibronectin and type IV collagen (Kawai et al, *Am. J. Path.* 137:1435–1446, 1990; Luthert and Williams, *Neurosc. Lett.* 126:110–112, 1991; Kawai et al, *Brain Res.* 592:278–282, 1992; Brandan and Inestrosa, *Gen. Pharm.* 24:1063–1068, 1993) were also tested. Initially different conditions (i.e. concentrations, molar/weight ratios of Aβ:plaque co-component and incubation times) were tested in an effort to synthesize the formation of the spherical congophilic maltese-cross, "amyloid star" plaques observed in human Alzheimer's disease brain.

Figure 1B:
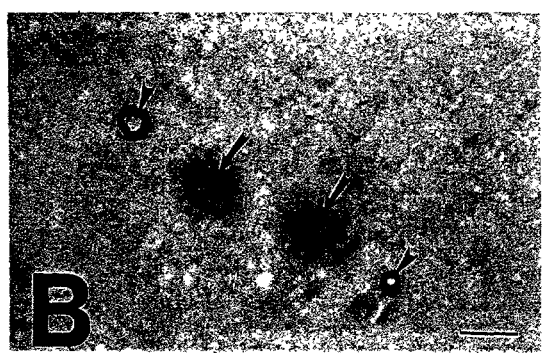
Figure 1C:
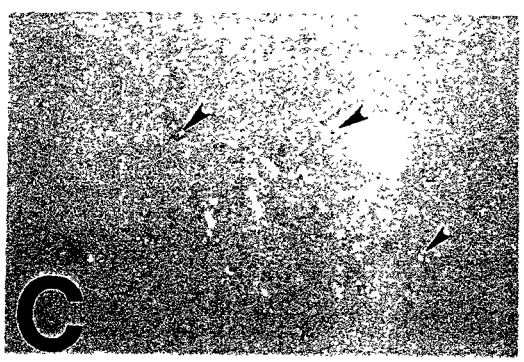
Figure 1D:
Figure 1E:
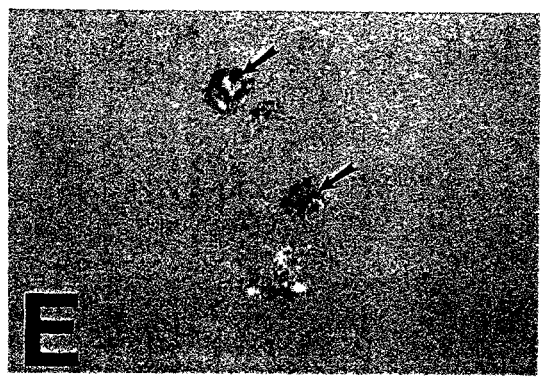
Figure 1F:
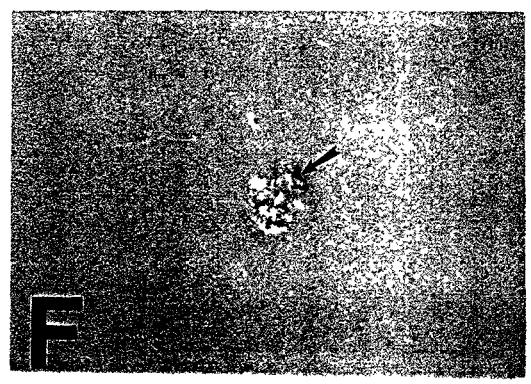
Figure 1G:
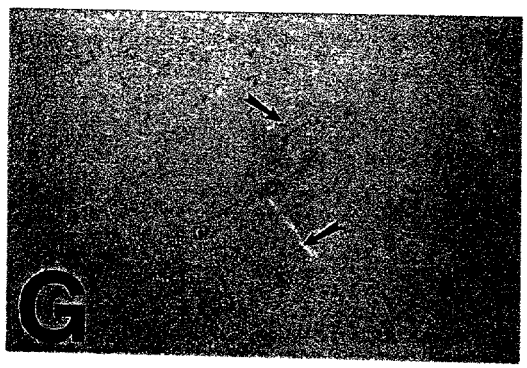
Figure 1H:
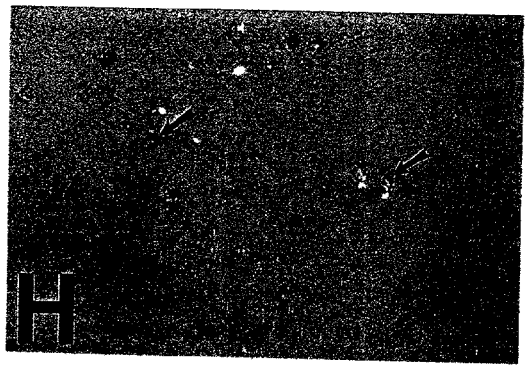
Figure 1I:
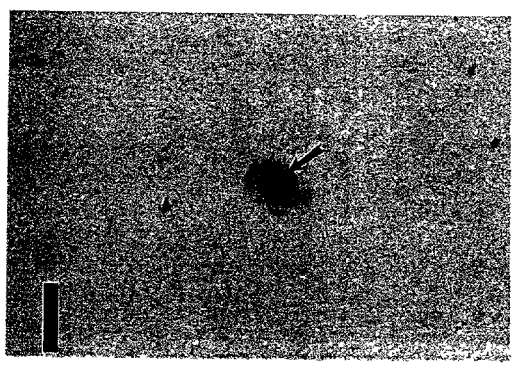
Figure 1J:
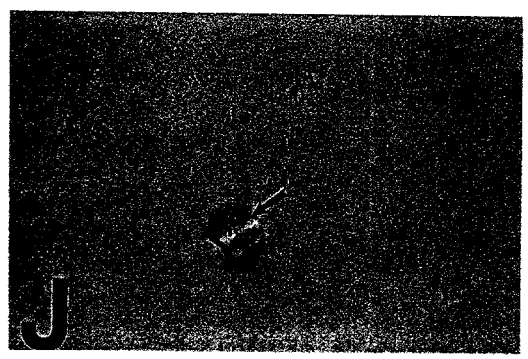

FIG. 1A (arrows) demonstrates the presence of 3 maltese-cross amyloid plaques (approximately 15–30 µM in diameter) in the hippocampus of a 86 year old male with Alzheimer's disease as viewed under polarized light, following staining with Congo red (Puchtler et al, *J. Histochem. Cytochem.* 10:355–364, 1962). Note the spherical shape of the compact amyloid plaques and their classical red/apple-green birefringence in a maltese-cross pattern (i.e. red color is 90 degrees to apple-green color). Upon rotation of the polarizer, a shift in colors of the plaque occurs such that the red color will change to apple-green, and the apple-green color will change to red (hence the term "red/apple-green birefringence"). FIG. 1B demonstrates perlecan immunolocalization (using apolyclonal antibody which recognizes perlecan core protein)(Hassell et al, *Proc. Natl. Acad. Sci. USA* 77:4494–4498, 1980) to the amyloid cores of two neuritic plaques (FIG. 1B, arrows) and small capillaries (FIG. 1B, arrowheads) in human Alzheimer's disease brain, as had been previously described (Snow et al, *Am. J. Path.* 133:456–463, 1988; Snow et al, *Am. J. Path.* 144:337–347, 1994).

In order to try to synthesize the formation of spherical congophilic maltese-cross amyloid plaques in a test tube a variety of techniques were tried. Preliminary studies indicated that compact amyloid plaque formation could occur only with perlecan (and not other amyloid plaque co-components or other basement membrane components), using the following methodology. 1 mg of Aβ 1–40 (Bachem Inc., Torrance CA) was dissolved in 1 ml of double distilled water or Tris-buffered saline (pH 7.4) to produce a stock solution at 1 mg/ml. 25 µl of the Aβ 1–40 stock solution was then added to a microcentrifuge tube containing 20 µg of lyophilized perlecan (isolated from the Engelbreth-Holm-Swarm tumor as described in Castillo et al, *J. Biochem.* 120:433–444, 1996), and then made up to a total final volume of 250 µl. The Aβ:perlecan molar ratio was 250:1 and the Aβ:perlecan weight ratio was 1:0.8. Similar results were observed using 25 µM of Aβ 1–40 with 125 nm of perlecan (i.e. Aβ:perlecan molar ratio of 200:1; Aβ:perlecan weight ratio of 1:1), or 125 µM Aβ 1–40 with 0.625 µM perlecan (i.e. Aβ:perlecan molar ratio 200:1). The incubation mixtures described above were then incubated at 37° C. Initial preliminary studies indicated that similar congophilic maltese-cross amyloid plaque formation occurred irrespective if the Aβ+/−perlecan was incubated in double distilled de-ionized water or Tris-buffered saline (pH 7.0). A glass pipette with a rubber attachment was initially used to mix Aβ+/−perlecan by gently pipetting the incubation mixture up and down for 30 seconds prior to incubation at 37° C. Following different incubation times including 1 day, 3 days, 5 days, and 1 week, 5 µl or 10 µl aliquots (four aliquots were taken per slide) of the incubation mixtures were taken and placed on gelatin-coated slides (preliminary studies indicated gelatin-coated or lysine-coated slides were best to use to retain the air-dried aliquots following staining procedures). The backsides of the glass-slides were first etched with four small circles using an etching pen prior to placement of the four aliquots on each slide for air-drying. Following each of the incubation times (described above) and prior to the placement of the aliquots on glass slides, the incubation mixtures were again gently pipetted up and down for 15 seconds, to ensure even displacement of materials. The aliquots placed on the gelatin-coated slides were then allowed to air-dry overnight at room temperature. The next day, the slides were stained with Congo red (Puchtler et al, *J. Histochem. Cytochem.* 10:355–364, 1962) and cover slipped. Any amyloid plaque cores that were formed were quantitated blindly by counting the number of plaque cores within each of four 5 µl aliquots.

Figure 1K:
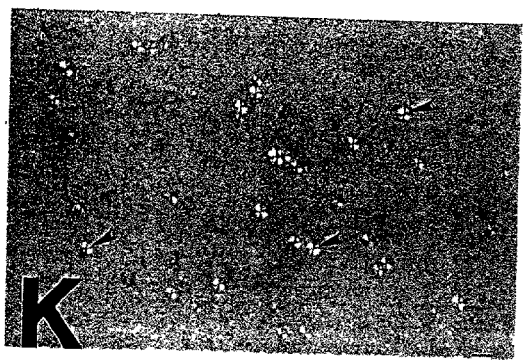
Figure 1L:
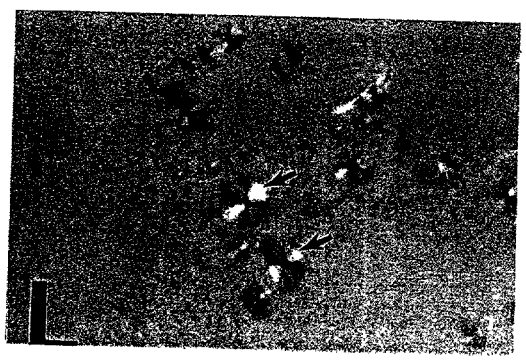

Initial studies using perlecan and Aβ at various Aβ:perlecan molar and/or weight ratios indicated that congophilic maltese-cross amyloid plaque formation would primarily occur within a preferred range of the two components (see FIGS. 1K and 1L). This preferred mixture was determined to be either 25 µM Aβ 1–40 with 100 nM of perlecan in double distilled water (i.e. Aβ:perlecan molar ratio=250:1; Aβ:perlecan weight ratio=1:0.8) (FIG. 1), or 125 µM Aβ 1–40 and 0.625 µM perlecan in double distilled water (i.e. Aβ:perlecan molar ratio of 200:1; Aβ:perlecan weight ratio=1:1) for visualization of congophilic maltese-cross amyloid plaques observed under polarized light (FIGS. 1K and 1L). An average of 30–40 congophilic maltese-cross amyloid plaques were observed per 5 µl aliquot (Table 1). The perlecan utilized for these studies was mouse perlecan ($M_r$=~800 kDa) isolated from the Engelbreth-Holm-Swarm (EHS) tumor, as previously described in an article by the inventors (Castillo et al, *J. Biochem.* 120:433–444, 1996), the text of which is hereby incorporated by reference. Mouse perlecan is known to have ~85–90% homology to human perlecan (Noonan et al, *J. Biol. Chem.* 266:22939–22947; 1991 Murdoch et al, *J. Biol. Chem.* 267:8544–8557, 1992; Kallunki and Tryggvason, *J. Cell Biol.* 116:559–571, 1992). The final purity and quality of the perlecan preparations were assessed by Alcian blue staining, Coomassie Blue staining, silver staining, and a series of Western blots employing antibodies against perlecan, laminin, type IV collagen and fibronectin, as previously described (Castillo et al, *J. Biochem.* 120:433–444, 1996). The perlecan utilized in the present studies was found to contain no other contamination by other basement membrane components or other proteins/PGs produced by the EHS tumor (Castillo et al, *J. Biochem.* 120:433–444, 1996). This was important since contaminating laminin in perlecan preparations derived from the EHS tumor usually contains Aβ fibril formation inhibitory activity (Castillo et al, *J. Biochem.* 120:433–444, 1996).

Time course studies (with analysis at 1 hour, 1 day, 3 days and 7 days) utilizing Aβ and perlecan mixtures as described above, revealed that congophilic maltese-cross amyloid plaque cores did not form instantaneously, but rather preferably required more than one day, or 3 to 5 days of incubation at 37° C. to induce formation. Lesser but probably acceptable results are still believed possible in the 1–10 day range, but in these disclosed methods, 7 days is a preferred incubation period. In addition, although amyloid plaque core formation was evident using Aβ 1–40, surprisingly no amyloid plaque core formation was observed using Aβ 1–42 (Bachem Inc, Torrance, Calif.) under the same conditions as described above, or by testing different conditions (including various concentrations, Aβ 1–42:perlecan molar/weight ratios, and incubation times up to 1 month).

A variety of different amyloid plaque co-components were then compared to perlecan for their possible ability to also form similar congophilic maltese-cross spherical amyloid plaques (Table 1, FIG. 1). In these studies, 25 µM of Aβ 1–40 or 1–42 (Bachem Inc., Torrance, Calif.) was incubated in double distilled water or Tris-buffered saline (pH 7.4) for 1 week at 37° C. either alone or in the presence of 100 nM of components including P component (Calbiochem; $M_r$=25 kDa), alpha$_1$-antichymotrypsin (Calbiochem; $M_r$=65 kDa), ApoE (Calbiochem; derived from human plasma; $M_r$=34 kDa), C1q (Chemicon; multimeric form $M_r$=460 kDa), C3 (Chemicon; dimeric form $M_r$=195 kDa), laminin (Sigma; derived from EHS tumor, $M_r$=~800 kDa), fibronectin (Sigma; derived from bovine plasma, $M_r$=450 kDa), type IV collagen (Sigma; derived from EHS tumor, $M_r$=~540 kDa), and perlecan (derived from EHS tumor) (Castillo et al, *J. Biochem.* 120:433–444, 1996). The Aβ:plaque co-component molar ratios were 250:1.

FIG. 1 is a montage of representative photomicrographs from different incubation mixtures (using 25 µM of Aβ 1–40 with 100 nM of different plaque co-components; Aβ:plaque co-component ratio of 250:1) as viewed on gelatin-coated slides under polarized light following a 1 week incubation at 37° C. Aβ 1–40 alone consistently demonstrated small and irregular Congo red positive deposits (FIG. 1C, arrowheads) with no apparent formation of congophilic maltese-cross amyloid plaque-like deposits. Over 20 different experiments utilizing Aβ 1–40 from different lots and sources demonstrated similar irregular Congo red deposits with no apparent maltese-cross formation. Aβ 1–40 with P component (FIG. 1D, arrow), Aβ 1–40 with alpha$_1$-antichymotrypsin (FIG. 1E, arrows) or Aβ 1–40 with ApoE (FIG. 1F, arrow) all produced aggregated "clumps" of Congo red positive deposits that were irregular in shape and with no apparent maltese-cross formation evident. Aβ 1–40 with C1q (FIG. 1G, arrows), Aβ 1–40 with C3 (not shown) or Aβ 1–40 with laminin (FIG. 1H, arrows) only demonstrated thin strands or small irregular Congo red positive deposits, whereas Aβ 1–40 with fibronectin (FIG. 1I, arrow) and Aβ 1–40 with type IV collagen (FIG. 1J) similarly produced aggregated "clumps" of Congo red deposits that were irregular in shape and contained no maltese-cross amyloid plaque formation present. On the other hand, Aβ 1–40 with perlecan produced multiple (>30 cores per 5 µl aliquot) spherical amyloid plaque core-like deposits (FIG. 1K, arrowheads) that were Congo red positive and demonstrated the classic maltese-cross pattern (FIG. 1L, arrows). These plaques ranged in diameter from 10 µm–50 µm, with an average diameter of 25 µm, and were virtually identical to the compact amyloid plaques observed in human Alzheimer's disease brain (compare FIGS. 1K or 1L to FIG. 1A). Induction by perlecan (or other highly sulfated GAGs and highly sulfated macromolecules, as described below) to form congophilic maltese-cross amyloid plaque deposits was apparently not an artifact of the procedure used (i.e. air-drying on glass slides prior to Congo red staining), since virtually identical maltese-cross amyloid plaque deposits were also observed when the incubation mixtures were stained with Congo red in solution (i.e. skipping the air-drying step), and viewed in solution under polarized light (not shown).

Similar congophilic maltese-cross amyloid plaques were observed using 125 µM Aβ 1–40 with 0.625 µM perlecan in al, Neuron 13:45–53, 1994; Suzuki et al, *Am. J. Path.* 145:452–460, 1994).

TABLE 1

TESTING OF VARIOUS PLAQUE CO-COMPONENTS FOR INDUCTION OF
CONGOPHILIC AND SPHERICAL MALTESE-CROSS
AMYLOID CORE DEPOSITS
(25 µM Aβ with 100 nM of plaque co-components in distilled water*;
1 week incubation at 37° C.)

| Plaque Component | Molar Ratio Aβ:Plaque Co-component | Amyloid Core Formation |
|---|---|---|
| Aβ 1-40 only | n/a | No |
| Aβ 1-42 only | n/a | No |
| Aβ 1-40 + P Component | 250:1 M ratio | No |
| Aβ 1-42 + P Component | 250:1 M ratio | No |
| Aβ 1-40 + alpha$_1$-antichymotrypsin | 250:1 M ratio | No |
| Aβ 1-42 + alpha$_1$-antichymotrypsin | 250:1 M ratio | No |
| Aβ 1-40 + ApoE | 250:1 M ratio | No |
| Aβ 1-42 + ApoE | 250:1 M ratio | No |
| Aβ 1-40 + C1q | 250:1 M ratio | No |
| Aβ 1-42 + C1q | 250:1 M ratio | No |
| Aβ 1-40 + C3 | 250:1 M ratio | No |
| Aβ 1-42 + C3 | 250:1 M ratio | No |
| Aβ 1-40 + perlecan | 250:1 M ratio | Yes**** |
| Aβ 1-42 + perlecan | 250:1 M ratio | No |
| Aβ 1-40 + laminin | 250:1 M ratio | No |
| Aβ 1-42 + laminin | 250:1 M ratio | No |
| Aβ 1-40 + fibronectin | 250:1 M ratio | No |
| Aβ 1-42 + fibronectin | 250:1 M ratio | No |
| Aβ 1-40 + type IV collagen | 250:1 M ratio | No |
| Aβ 1-42 + type IV collagen | 250:1 M ratio | No |

*Similar results were obtained with 125 µM Aβ with 0.625 µM of plaque co-components in distilled water; Aβ:plaque component molar ratio of 200:1.
***amyloid plaque core formation was scored blindly according to the number of plaque cores observed in a 5 µl aliquot (*1–5 cores; 5–10 cores; *10–30 cores; **30–50 cores; ***>50 cores)

double distilled water or Tris-buffered saline (pH 7.4) (i.e. Aβ:perlecan molar ratio of 200:1; Aβ:perlecan weight ratio of 1:1), but with more amyloid plaque cores present on the slide (due to a higher amounts of Aβ and perlecan) (not shown). In addition, a similar lack of congophilic maltese-cross amyloid plaque formation was observed using 125 µM Aβ 1–40 plus 0.626 µM of other plaque co-components (as listed above) in double distilled water or Tris-buffered saline (pH 7.4)(not shown).

Table 1 summarizes initial studies testing various plaque co-components for induction of congophilic and spherical maltese-cross amyloid core deposits. Note that perlecan in the presence of Aβ 1–40 was able to induce formation of such deposits as described above. Surprisingly, under the same conditions, Aβ 1–42 was ineffective in the production of congophilic and spherical maltese-cross amyloid core deposits indicating that the two hydrophobic residues of Aβ 1–42 may hinder amyloid core formation in vitro. This latter finding suggests that compact amyloid plaque formation likely does not occur in vivo until the two hydrophobic residues at the carboxyl-end of 1–42 are cleaved. The idea that compact amyloid plaque formation is most likely a later event in plaque development correlates quite well with the discovery that Aβ 1–40, but not 1–42, appears critical for the formation of compact amyloid plaques which demonstrate a maltese-cross when stained with Congo red and viewed under polarized light. Previous studies conducted with monoclonal antibodies specific to the 1–40 and the 1–42(43) amino acid forms of Aβ have demonstrated that Aβ 1–42 (43), rather Aβ 1–40, is predominantly abundant in diffuse plaques and neuritic plaques, whereas Aβ 1–40 (rather Aβ 1–42/1–43) is predominant in "core plaques" (Iwatsubo et al, Neuron 13:45–53, 1994; Suzuki et al, *Am. J. Path.* 145:452–460, 1994).

Example 2

Induction of Amyloid Plaque Core Formation by Highly Sulfated Glycosaminoglycans (i.e. Heparan Sulfate and Heparin)

Since perlecan is a known to contain glycosaminoglycans (GAGs) of the heparan sulfate class, the next study was implemented to determine whether heparan sulfate and/or other sulfated GAGs were also capable of inducing congophilic maltese-cross amyloid plaque formation. Previous studies have demonstrated that besides heparan sulfate GAGs, a number of other classes of GAGs are found in association with amyloid plaques in human Alzheimer's disease brain, including dermatan sulfate containing PGs (specifically decorin)(Snow et al, *J. Histochem. Cytochem.*, 40:105–113, 1992), keratan sulfate PGs (specifically synaptoglycan)(Snow et al, *Exp. Neurol.* 138:305–317, 1996) and chondroitin sulfate GAGs (DeWitt et al, *Exp. Neurol.* 121: 149–152, 1993). Therefore, sulfated GAGs including heparin, heparan sulfate, chondroitin-4-sulfate, chondroitin-6-sulfate and dermatan sulfate were also tested for their potential ability to induce congophilic maltese-cross amyloid plaque formation. Initially different conditions (i.e. concentrations, molar/weight ratios of Aβ:sulfated GAG/sulfated macromolecule, incubation times) were tested in an effort to reduplicate the formation of spherical congophilic maltese-cross amyloid plaques observed in human Alzheimer's disease brain.

25 μM of Aβ 1–40 or Aβ 1–42 (Bachem Inc., Torrance, Calif.) was incubated in double distilled water or Tris-buffered saline for 1 week at 37° C. either alone, or in the presence of various amounts of heparin (Sigma; from intestinal mucosa; $M_r$=5 kDa), heparan sulfate (Sigma; from bovine kidney; $M_r$=25 kDa), chondroitin-4-sulfate (Sigma; from trachea; $M_r$=31 kDa), chondroitin-6-sulfate (Sigma; from trachea; $M_r$=54 kDa) and dermatan sulfate (Sigma; from mucosa; $M_r$=16 kDa) (Table 2). At 1 week, 5 μl aliquots of the incubation mixtures were air-dried on gelatin-coated slides, stained with Congo red and viewed under polarized light as described in Example 1. Congophilic maltese-cross amyloid plaques formed were quantitated by counting the number of plaques within each of four 5 μl aliquots. A variety of different weight and/or molar ratios were first tested in preliminary studies (see Table 3 for heparan sulfate weight ratio studies) to determine whether 1) other sulfated GAGs were also capable of inducing congophilic maltese-cross amyloid plaque core formation, and 2) what the optimum Aβ:sulfated GAG molar/weight ratios were for such induction.

Figure 2A:
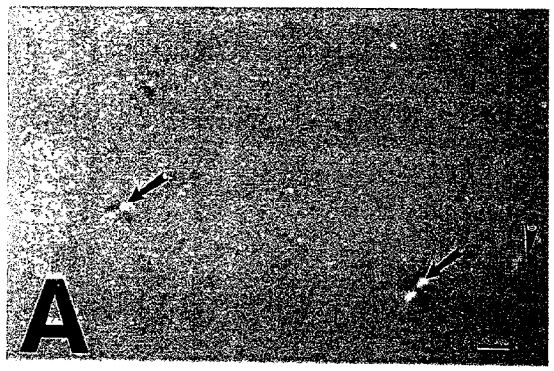
FIGS. 2A–2I are photomicrographs of the in vitro formation of congophilic and maltese-cross spherical amyloid plaques by another embodiment of the inventive method.
Figure 2B:
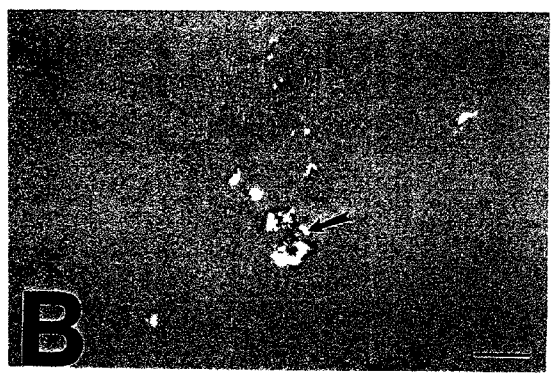

FIG. 2A (arrows) demonstrates the presence of 2 congophilic maltese-cross amyloid plaques in the calcarine cortex of a 46 year old male with familial Alzheimer's disease, following staining with Congo red (with no counter stain) and as viewed under polarized light. A nearby blood vessel demonstrating amyloid angiopathy (FIG. 2A, arrowhead) is also shown. As demonstrated in FIG. 2B (arrow), following a 1 week incubation at 37° C., Aβ 1–40 alone consistently demonstrated small and irregular compact Congo red positive deposits with no apparent formation of a maltese-cross. On the other hand, congophilic maltese-cross amyloid plaque formation was induced by both heparin (FIG. 2C, arrows) and heparan sulfate GAGs (FIG. 2D, arrows) under the appropriate conditions. The preferred molar ratio of Aβ:heparin for congophilic maltese-cross amyloid plaque formation was found to be about 1:5 (with Aβ 1–40 at 25 μM). On the other hand, the preferred weight ratio of Aβ:heparan sulfate for maltese-cross amyloid plaque formation was found to be 1:8 (i.e. 50 μg Aβ 1–40 in 100 μl of double distilled water with 400 μg of heparan sulfate)(Tables 2 and 3). Similar congophilic maltese-cross amyloid plaque formation was observed with Aβ 1–40 at 125 μM (in double distilled water or TBS) for heparin and heparan sulfate at the same molar or weight ratios as described above (not shown). Using the same molar and/or weight ratios as described above, congophilic maltese-cross amyloid plaque formation was not observed with chondroitin-4-sulfate (not shown), chondroitin-6-sulfate (not shown) or dermatan sulfate (FIG. 2E, arrow) indicating that highly sulfated GAGs were primarily effective for induction of amyloid plaque core formation. As observed with perlecan, even though heparin and heparan sulfate GAGs were effective as inducers of congophilic maltese-cross amyloid plaque core formation when incubated with Aβ 1–40, no congophilic maltese-cross amyloid plaques were observed under the same conditions when using Aβ 1–42 (Table 2).

TABLE 2

TESTING OF SULFATED GLYCOSAMINOGLYCANS AND RELATED SULFATED MACROMOLECULES FOR INDUCTION OF CONGOPHILIC AND SPHERICAL MALTESE-CROSS AMYLOID CORE DEPOSITS (25 μM Aβ in distilled water*; 1 week incubation at 37° C.)

| Plaque Component | Weight/Molar Ratio Aβ:Plaque Co-component | Amyloid Core Formation |
| --- | --- | --- |
| Aβ 1-40 only | n/a | No |
| Aβ 1-42 only | n/a | No |
| Aβ 1-40 + Heparin | 1:5 M ratio | Yes*** |
| Aβ 1-42 + Heparin | 1:5 M ratio | No |
| Aβ 1-40 + heparan sulfate | 1:8 wt ratio | Yes** |
| Aβ 1-42 + heparan sulfate | 1:8 wt ratio | No |
| Aβ 1-40 + 220 kDa EHS HSPG | 5:1 wt ratio | Yes***** |
| Aβ 1-42 + 220 kDa EHS HSPG | 5:1 wt ratio | No |
| Aβ 1-40 + chondroitin-4-sulfate | 1:5 M ratio | No |
| Aβ 1-42 + chondroitin-4-sulfate | 1:5 M ratio | No |
| Aβ 1-40 + chondroitin-6-sulfate | 1:5 M ratio | No |
| Aβ 1-42 + chondroitin-6-sulfate | 1:5 M ratio | No |
| Aβ 1-40 + dermatan sulfate | 1:5 M ratio | No |
| Aβ 1-42 + dermatan sulfate | 1:5 M ratio | No |
| Aβ 1-40 + inorganic sulfate | 1:5 M ratio | No |
| Aβ 1-42 + inorganic sulfate | 1:5 M ratio | No |
| Aβ 1-40 + N-acetylated; completely desulfated heparin | 1:5 M ratio | No |
| Aβ 1-40 + N-desulfated; N-acetylated heparin | 1:5 M ratio | Yes* |
| Aβ 1-40 + completely desulfated N-sulfated heparin | 1:5 M ratio | No |
| Aβ 1-40 + dextran sulfate | 1:5 M ratio | Yes***** |
| Aβ 1-42 + dextran sulfate | 1:5 M ratio | No |
| Aβ 1-40 + dextran (unsulfated) | 1:5 M ratio | No |
| Aβ 1-42 + dextran (unsulfated) | 1:5 M ratio | No |
| Aβ 1-40 + pentosan polysulfate | 1:5 M ratio | Yes**** |
| Aβ 1-42 + pentosan polysulfate | 1:5 M ratio | No |
| Aβ 1-40 + Congo red | 1:5 M ratio | No |
| Aβ 1-42 + Congo red | 1:5 M ratio | No |

TABLE 2-continued

TESTING OF SULFATED GLYCOSAMINOGLYCANS AND RELATED SULFATED
MACROMOLECULES FOR INDUCTION OF CONGOPHILIC AND SPHERICAL
MALTESE-CROSS AMYLOID CORE DEPOSITS (25 μM Aβ in distilled water*;
1 week incubation at 37° C.)

| Plaque Component | Weight/Molar Ratio Aβ:Plaque Co-component | Amyloid Core Formation |
| --- | --- | --- |
| Aβ 1-40 + polyvinyl sulphonate | 1:40 wt ratio | Yes**** |
| Aβ 1-42 + polyvinyl sulphonate | 1:8 wt ratio | No |

*Similar results were obtained with 125 μM Aβ in distilled water; n/a = not applicable
***amyloid plaque core formation was scored blindly according to the number of plaque cores observed in a 5 μl aliquot (*1–5 cores; 5–10 cores; *10–30 cores; **30–50 cores; ***>50 cores)

Example 3

Induction of Compact Amyloid Plaque Formation by Other Sulfated Macromolecules (i.e. Dextran Sulfate, Pentosan Polysulfate and Polyvinyl Sulphonate)

The induction of compact amyloid plaque formation by highly sulfated GAGs such as heparin and heparan sulfate GAGs, suggested that the sulfate content of GAGs maybe critical for the formation of congophilic maltese-cross amyloid plaques. The next study therefore tested the hypothesis that similar amyloid plaque induction could also be induced by other highly sulfated macromolecules. Therefore, other highly sulfated macromolecules including dextran sulfate (with unsulfated dextran for comparison), pentosan polysulfate, Congo red and polyvinyl sulphonate were tested for their potential ability to also induce congophilic maltese-cross amyloid plaque formation. For these studies, 25 μM of Aβ 1–40 or Aβ 1–42 (Bachem Inc., Torrance, Calif.) was incubated in double distilled water or Tris-buffered saline (pH 7.4) for 1 week at 37° C. either alone, or in the presence of various amounts of dextran sulfate (Sigma; $M_r$=8 kDa), unsulfated dextran (Sigma; $M_r$=11.3 kDa), pentosan polysulfate (Sigma; $M_r$=3 kDa), Congo red (Sigma; $M_r$=0.7 kDa), polyvinyl sulphonate (Aldrich; 25% weight in water) and inorganic sodium sulfate (Sigma; $M_r$=0.142 kDa). At 1 week, 5 μl aliquots of the incubation mixtures were air-dried on gelatin-coated slides, stained with Congo red and viewed under polarized light as described in Example 1. A variety of different weight and/or molar ratios were initially tested in preliminary studies (see Table 3 for polyvinyl sulphonate studies) to determine whether 1) other sulfated macromolecules were also capable of inducing congophilic maltese-cross amyloid plaque formation, and 2) what the optimum Aβ:sulfated macromolecules molar/weight ratios were needed for such induction.

Congophilic maltese-cross amyloid plaque formation was not observed with Congo red (FIG. 2F, arrows, Aβ:Congo red molar ratio of 1:5) or inorganic sulfate (not shown) at any concentration tested. However, dextran sulfate, pentosan polysulfate and polyvinyl sulphonate were all effective inducers of congophilic maltese-cross amyloid plaque formation under the appropriate conditions (Table 2; Table 3). As shown in FIG. 2G (arrows), pentosan polysulfate, at a preferred Aβ:pentosan polysulfate molar ratio of 1:5 (maintaining Aβ at 25 μM or 125 μM), induced congophilic maltese-cross amyloid plaque formation (average of 30–50 cores per 5 μl aliquot following a 1 week incubation at 37° C. Dextran sulfate was also very effective at inducing compact amyloid plaque formation (average of >50 cores per 5 μl aliquot) when used at a preferred Aβ:dextran sulfate molar ratio of 1:5. As shown in FIGS. 2H (arrowheads) and 2I, dextran sulfate induced congophilic amyloid plaque formation with maltese-crosses that was virtually identical to Congo red positive compact amyloid plaques in human Alzheimer's disease brain (compare FIGS. 2H to 2A). On the other hand, unsulfated dextran did not induce amyloid plaque formation again implicating the importance of the sulfate moieties (not shown).

Polyvinyl sulphonate (PVS), an agent previously claimed to be a possible therapeutic for inhibition of amyloid deposition/formation (Kisilevsky et al, *Nature Med.* 2:143–148, 1995), was also tested for its potential ability to form congophilic maltese-cross amyloid deposits, since PVS is also a highly sulfated compound. For these studies increasing amounts of PVS (Aldrich, 25% solution w/v) were used to determine the optimum Aβ:PVS weight ratio for potential compact amyloid plaque formation (Table 3). More specifically, 50 μg of Aβ 1–40 (Bachem Inc., Torrance, Calif.) was is incubated in 100 μl double distilled water or Tris-buffered saline (pH 7.4) for 1 week at 37° C. either alone, or in the presence of increasing amounts of PVS (including 25 μg, 50 g, 100 μg, 200 μg, 250 μg, 400 μg, 800 μg, 1 mg, 2 mg and 4 mg) (FIG. 3; Table 3). The weight ratios of Aβ:PVS for these studies therefore ranged from 2:1 through 1:80. At 1 week, 5 μl aliquots of the incubation mixtures were air-dried on gelatin-coated slides, stained with Congo red and viewed under polarized light as described in Example 1.

As shown in FIG. 3, an Aβ:PVS weight ratio of 2:1 (FIG. 3A, arrowheads) or 1:1 demonstrated congophilic deposits of amyloid primarily at the periphery of the 5 μl aliquot. Only faint birefringence was observed in the center of each 5 μl aliquot (FIGS. 3A and 3B) suggesting minimal amyloid formation, and no compaction of the amyloid was apparent. An increase in the compaction of the congophilic amyloid deposits was observed with increasing amounts of PVS, specifically Aβ:PVS weight ratios of 1:2 (not shown) and 1:4 (FIG. 3C). Once an Aβ:PVS weight ratio of 1:5 was reached (i.e. 50 μg Aβ+250 μg PVS in 100 μl total volume), congophilic maltese-cross amyloid plaque formation was observed (FIG. 3D). Increasing amounts of PVS appeared to lead to general morphological changes in the compaction and appearance of the Aβ amyloid deposits, such that a large number of congophilic maltese-cross amyloid plaques were eventually formed (Table 3; FIGS. 3E–H). Aβ:PVS weight ratios of 1:8, 1:10 and 1:16 are demonstrated in FIGS. 3E, 3F and 3G, respectively. An optimum number (>50 cores per 5 μl aliquot) of congophilic maltese-cross amyloid plaques were observed at an Aβ:PVS weight ratio of 1:40 (FIG. 3H, arrowheads). A decrease in the number of amyloid plaque cores induced by PVS was observed with even greater amounts of PVS (i.e. Aβ:PVS weight ratio of 1:80)(FIG. 3I) demonstrating that there is an optimum ratio for mixing various components to observe optimal amyloid plaque core formation. These studies again demonstrated that the weight/molar ratio of Aβ:sulfated macromolecule was critical for the induction of congophilic maltese-cross amyloid plaque formation.

maltese-cross amyloid plaque formation (producing >50 amyloid plaque cores per 5 µl aliquot). Increasing concentrations (i.e. 50 µg or 100 µg in a final volume of 100 µl) of the EHS ~220 kDa HSPG appeared to produce an even greater number of congophilic maltese-cross amyloid plaques (not shown). This study demonstrated the use of another HSPG for the induction of congophilic maltese-cross amyloid plaque formation.

TABLE 3

TESTING OF DIFFERENT WEIGHT RATIOS FOR INDUCTION OF CONGOPHILIC AND SPHERICAL MALTESE-CROSS AMYLOID CORE DEPOSITS
(in 100 µl distilled water; 1 week incubation at 37° C.)

| Plaque Component | Weight/Molar Ratio Aβ:Component | Amyloid Core Formation |
|---|---|---|
| 50 µg Aβ 1-40 + 25 µg heparansulfate | 2:1 wt ratio | No |
| 50 µg Aβ 1-40 + 50 µg heparansulfate | 1:1 wt ratio | No |
| 50 µg Aβ 1-40 + 100 µg heparansulfate | 1:2 wt ratio | No |
| 50 µg Aβ 1-40 + 200 µg heparansulfate | 1:4 wt ratio | No |
| 50 µg Aβ 1-40 + 400 µg heparansulfate | 1:8 wt ratio | Yes** |
| 50 µg Aβ 1-40 + 800 µg heparansulfate | 1:16 wt ratio | Yes** |
| 50 µg Aβ 1-40 + 25 µg PVS | 2:1 wt ratio | No |
| 50 µg Aβ 1-40 + 50 µg PVS | 1:1 wt ratio | No |
| 50 µg Aβ 1-40 + 100 µg PVS | 1:2 wt ratio | No |
| 50 µg Aβ 1-40 + 200 µg PVS | 1:4 wt ratio | Yes* |
| 50 µg Aβ 1-40 + 250 µg PVS | 1:5 wt ratio | Yes* |
| 50 µg Aβ 1-40 + 400 µg PVS | 1:8 wt ratio | Yes** |
| 50 µg Aβ 1-40 + 800 µg PVS | 1:16 wt ratio | Yes*** |
| 50 µg Aβ 1-40 + 1 mg PVS | 1:20 wt ratio | Yes**** |
| 50 µg Aβ 1-40 + 2 mg PVS | 1:40 wt ratio | Yes***** |
| 50 µg Aβ 1-40 + 4 mg PVS | 1:80 wt ratio | Yes*** |

***amyloid plaque core formation was scored blindly according to the number of plaque cores observed in a 5 µl aliquot (*1–5 cores; 5–10 cores; *10–30 cores; **30–50 cores; ***>50 cores)

Example 4

Induction of Amyloid Plaque Formation by a ~220 kDa Heparan Sulfate Proteoglycan Obtained During the Isolation of Perlecan from the Engelbreth-Holm-Swarm Tumor Our previous studies have demonstrated that perlecan can be effectively isolated from the Engelbreth-Holm-Swarm (EHS) tumor (Castillo et al, *J. Biochem.* 120:433–444, 1996). During the course of these studies, we identified a ~220 kDa aggregating PG which could be separated from perlecan by gel filtration chromatography. This particular PG was found to contain heparan sulfate GAGs chains as demonstrated by heparitinase/heparinase digestion studies (Castillo et al, *J. Biochem.* 120:433–444, 1996). Since this particular PG was also found to be rich in heparan sulfate GAGs, as determined using an Alcian Blue assay (Björnson, *Anal. Biochem.* 210:282–291, 1993), we tested it also for the possible induction of congophilic maltese-cross amyloid plaque formation. For this study, 50 µg of Aβ 1–40 (Bachem Inc., Torrance, Calif.) was incubated in 100 Tris-buffered saline (pH 7.4) for 1 week at 37° C. either alone, or in the presence of 10 µg (determined using an Alcian blue assay) (Björnson, *Anal. Biochem.* 210:282–291, 1993) of the 220 kDa HSPG (Aβ:HSPG weight ratio of 5:1). At 1 week, 5 µl aliquots of the incubation mixtures were air-dried on gelatin-coated slides, stained with Congo red and viewed under polarized light as described in Example 1.

As shown in FIG. 4B (arrowheads), the ~220 kDa HSPG was also extremely effective as an inducer of congophilic Example 5

The Importance of the Sulfate Moieties for Induction of Congophilic Maltese-Cross Amyloid Plaque Formation The studies thus far described suggest that the sulfate moieties of GAGs or other macromolecules are critical for the induction of congophilic maltese-cross amyloid plaque formation. In order to further test this hypothesis, the next study analyzed modified heparins for their ability to also induce amyloid plaque formation. 25 µM of Aβ 1–40 (Bachem Inc., Torrance, Calif.) was incubated in double distilled water or Tris-buffered saline for 1 week at 37° C. either alone, or in the presence of heparin (Sigma; from intestinal mucosa; $M_r$=5 kDa), completely desulfated, N-sulfated heparin (Seikagaku America; $M_r$=5 kDa), N-desulfated, N-acetylated heparin (Seikagaku America; $M_r$=5 kDa), and completely de-sulfated, N-acetylated heparin (Seikagaku America; $M_r$=5 kDa). An Aβ:heparin/modified heparin molar ratio of 1:5 was used as previously described. At 1 week, 5 µl aliquots of the incubation mixtures were air-dried on gelatin-coated slides, stained with Congo red and viewed under polarized light as described in Example 1.

Figure 2C:
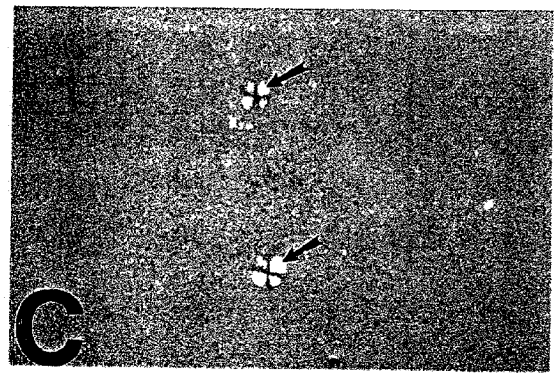
Figure 2D:
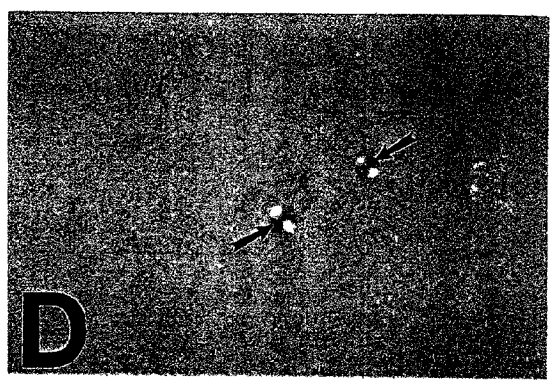
Figure 2E:
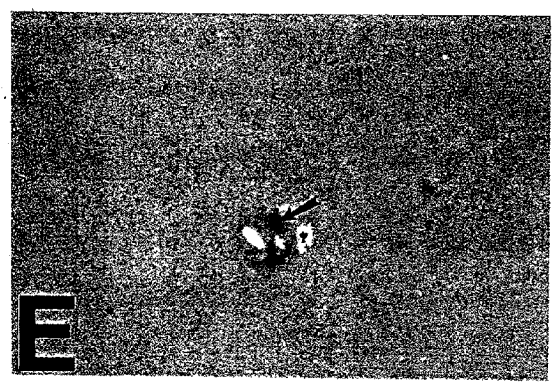
Figure 2F:
Figure 2G:
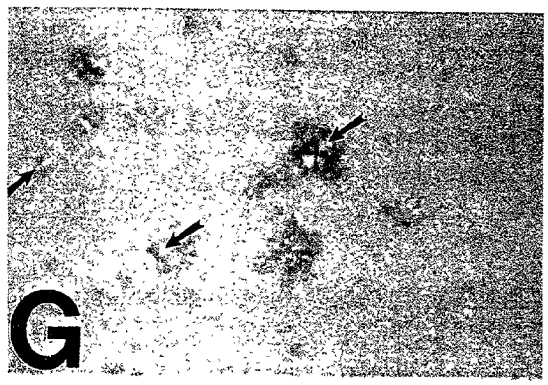
Figure 2H:
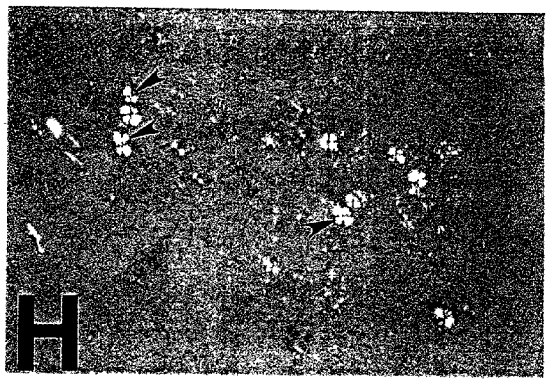
Figure 2I:
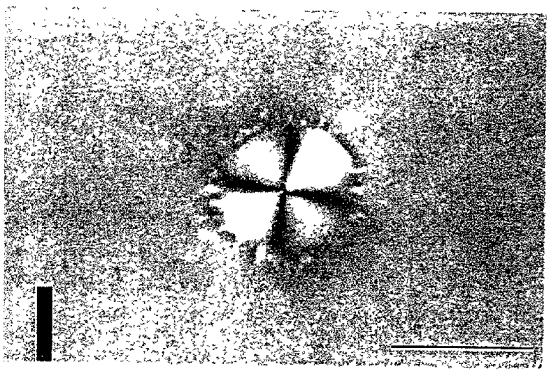
Figure 3A:
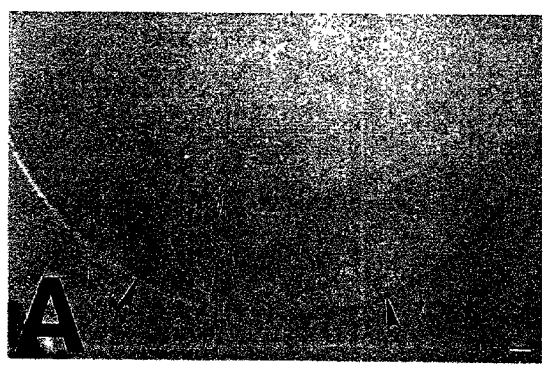
FIGS. 3A–3I are photomicrographs of the in vitro formation of congophilic and maltese-cross spherical amyloid plaques by another embodiment of the inventive method.
Figure 3B:
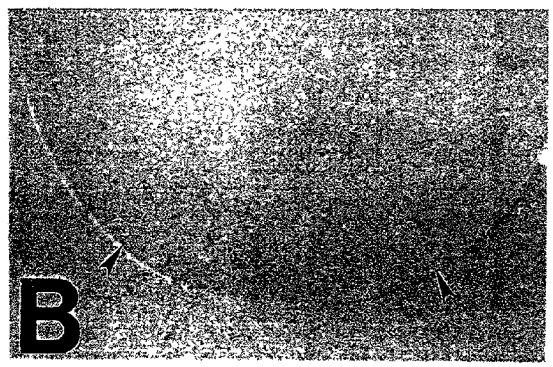
Figure 3C:
Figure 3D:
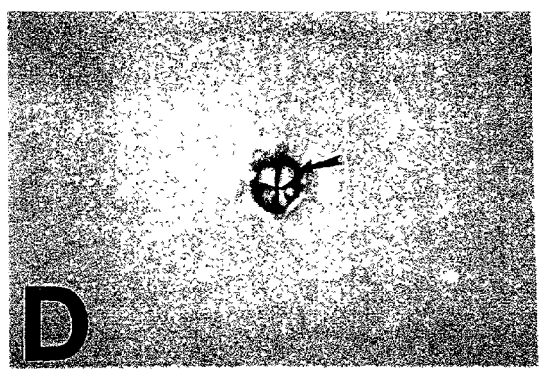
Figure 3E:
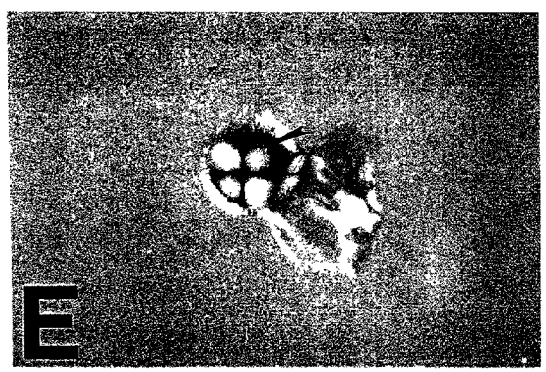
Figure 3F:
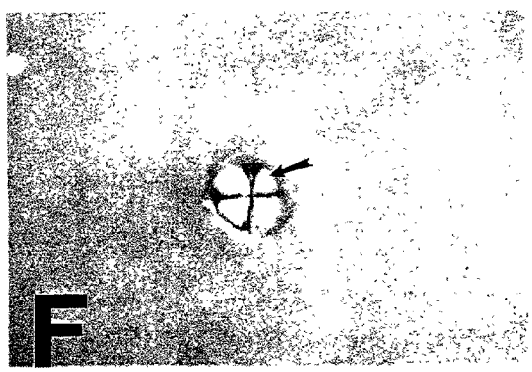
Figure 3G:
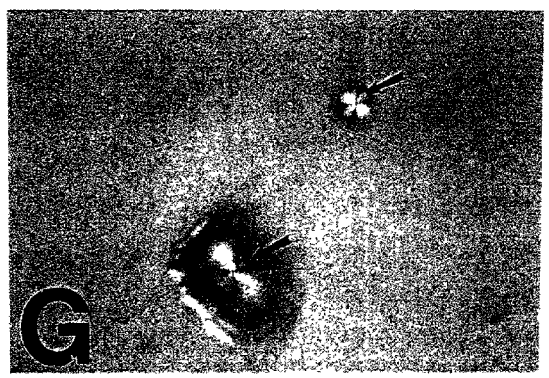
Figure 3H:
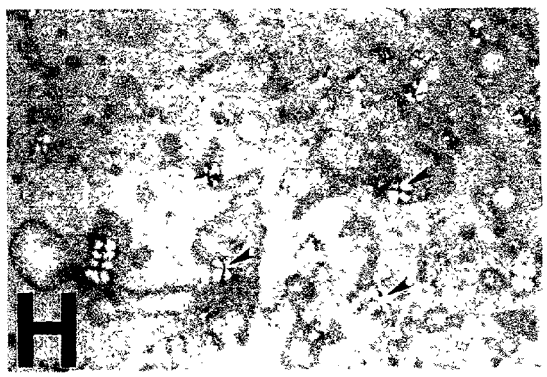
Figure 3I:
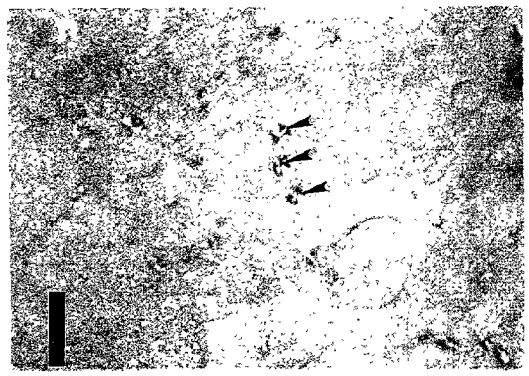

As shown in Table 2 (FIG. 2C), heparin induced congophilic maltese-cross amyloid plaque formation (see FIG. 2C). However, removal of sulfates from heparin (i.e. completely desulfated, N-acetylated heparin) resulted in complete loss of congophilic maltese-cross plaque formation. A similar loss of heparin's ability to induce compact amyloid plaque formation was also observed when the O-sulfate groups were removed from heparin (i.e. completely desulfated N-sulfated heparin). Amyloid plaque formation was still observed, however, using N-desulfated, N-acetylated heparin (i.e removal of N-sulfates), suggesting the importance of the O-sulfate groups for amyloid plaque induction. This study confirmed that the sulfate moieties on GAGs are critical for the formation of congophilic maltese-cross amyloid plaques.

Example 6

Comparison of Compact Amyloid Plaques Formed in vitro to Isolated Human Alzheimer's Disease Amyloid Plaque Cores: Transmission Electron Microscopy Studies Amyloid plaques formed following the co-incubation of Aβ 1–40 with perlecan, highly sulfated GAGs or related sulfated macromolecules at the light microscopic level appear very similar to the congophilic amyloid plaques present in human Alzheimer's disease brain. When stained with Congo red and viewed under polarized light, both types of plaques (i.e. those formed in vitro and those present in Alzheimer's brain) were spherical in shape, and demonstrated a classic maltese-cross (with the red and apple-green colors of the plaque aligned 90° to each other). In the next study, transmission electron microscopy was utilized to compare the ultrastructural morphology of amyloid plaque cores isolated from human Alzheimer's disease brain to amyloid plaques that were formed in vitro. It was important to determine whether 1) the amyloid plaques produced artificially in vitro had a similar "amyloid star" ultrastructural morphology to those isolated from human Alzheimer's disease brain, and whether 2) the diameter of the individual amyloid fibrils within the amyloid plaques produced artificially in vitro were similar to amyloid fibrils present in human Alzheimer's disease plaques.

For these studies, cores of neuritic plaques were isolated from human Alzheimer's disease brain by using a modification (DeWitt et al, *Exp. Neurol.* In Press, 1998) of an established method (Selkoe et al, *J. Neurochem.* 46:1820–1834, 1986). Cortex from the frontal and temporal lobes (100–150 g) of a case of Alzheimer's disease, verified by histology to contain many amyloid plaques, was used. Blood vessels, meninges and white matter was carefully removed after which the tissue was well minced and incubated for 2 hours at room temperature in 5 volumes of 2% SDS in Tris-HCl (pH 7.6), followed by homogenization by 20 strokes in a Dounce homogenizer (pestle A)(Kontes Glass Company, Vineland, N.J.). The homogenate was then heated to 100° C. for 10 minutes and sieved through a 100 μM nylon mesh. The pellet resulting from centrifugation at 300× g for 30 minutes was washed in 0.1% SDS, 50 mM Tris, 150 mM NaCl, 0.02% NaN$_3$, and centrifuged again at 300× g for 10 minutes. Using a Dounce homogenizer (pestle A), the resulting pellet was again homogenized in 5 ml of 0.1% SDS buffer (approximately 5 m/s) and sieved through a 35 μM nylon mesh. Subsequently, the material was loaded onto a discontinuous gradients of layers consisting of 1.2M, 1.4M, 1.6M and 1.8M sucrose dissolved in 1%SDS, 50 mM Tris(pH 7.6). Following centrifugation at 72,000×g for 60 minutes, the material at all interfaces were collected and diluted with 5 volumes with 0.1% SDS in 50 mM Tris-HCl (pH 7.6) and centrifuged at 300×g for 30 minutes. Each pellet was assayed for cores of senile plaques by Congo red staining (Puchtler et al, *J. Histochem. Cytochem.* 10:355–364, 1962). Most amyloid core plaques were found in the 1.4/1.6 interface, as described previously (Selkoe et al, *J. Neurochem.* 46:1820–1834, 1986). The sample from the 1.4/1.6 interface was then loaded on a Coulter EPICS Elite ESP cell sorter (Coulter Corporation, Hialeah, Fla.). The cores were run through at a flow rate of 1428 particles/sec through a 100 μM 3× tip. An argon laser with an excitation maximum at 488 nm was used for sorting based on side scatter. Plaque cores were selected based on size (12–50 μM). Amyloid plaque cores obtained by the above described method were a generous gift form Dr. George Perry, Case Western Reserve University, Cleveland, Ohio USA.

125 μM of Aβ 1–40 was incubated in double distilled water for 1 week at 37° C., either alone, or in the presence of 0.625 μM of perlecan (Aβ:perlecan molar ratio of 200:1; Aβ:perlecan weight ratio of 1:1). A 10 μl aliquot of each sample (including a sample of human Alzheimer's disease amyloid plaque cores isolated as described above) was air-dried for 1 hour on plastic petri dishes. After circling each dried spot on the reverse side with an etching pen, the samples were fixed in situ with 3% glutaraldehyde in 0.1M NaPO$_4$ buffer (pH 7.3) for 10 minutes. After rinsing 3 times with filtered water, the samples were then post-fixed for 10 minutes with 1% osmium tetroxide in distilled water for 10 minutes, rinsed as before and air-dried overnight. After examining and photographing the sample on the petri dish at the light microscopic level (FIG. 4), the samples were rinsed three times with absolute ethanol, infiltrated with epoxy resin (Medcast, Ted Pella, Redding, Calif.) and polymerized for 48 hours at 65° C. After cooling and transferring the locating circle to the polymerized plastic surface, the plastic dish was separated from the embedded sample. En face 80–100 nm sections were taken from the sample areas and mounted on formvar coated 100 mesh copper grids or naked 200 mesh grids. The sections were stained with 7% aqueous uranyl acetate followed by lead citrate (Reynolds, *J. Cell Biol.* 17:208–212, 1963) and examined, and photographed with a JEM 1200 EX II (JEOL Ltd, Tokyo, Japan), using 80 kV accelerating voltage.

As shown in FIG. 5, a 1 week co-incubation of Aβ 1–40 with perlecan produced spherical amyloid plaque-like deposits. Numerous amyloid plaque-like deposits were present in the embedded plastic when viewed using a Olympus light microscope (FIGS. 5A and 5B, arrowheads). The amyloid plaque-like deposits induced by perlecan were spherical in shape (FIGS. 5A and 5B, arrowheads) and even with a light microscope appeared to consist of radiating bundles of fibrils emanating from a central source. Amyloid plaque cores isolated from human Alzheimer's disease brain and embedded in plastic as described above were very similar in appearance to those induced by perlecan (not shown). Samples of Aβ 1–40 alone did not demonstrate any such spherical plaque-like appearance (not shown).

Transmission electron microscopy demonstrated the ultrastructural similarity of amyloid plaque-like deposits induced by perlecan to those isolated from human Alzheimer's disease brain (FIG. 6). The ultrastructural morphology of the amyloid plaque deposit formed following a 1 week incubation of Aβ 1–40 with perlecan was virtually identical to those isolated from human Alzheimer's disease brain microscopy. FIGS. 6A and 6C demonstrate the ultrastructural appearance of a single amyloid plaque core derived from the cortex of a human patient with Alzheimer's disease. Note the "amyloid star" appearance of the human plaque, with bundles of radiating amyloid fibrils appearing to emanate from the center of the plaque (FIG. 6A). A similar "amyloid star" ultrastructural morphology was also observed following a 1 week incubation of Aβ 1–40 with perlecan (FIG. 6B). These deposits were also compact, spherical in shape, and consisted of amyloid fibrils appearing to emanate from the center of the plaque (thus the "star"

shape appearance). The only real difference in the artificially produced amyloid plaque was that it sometimes contained a corona, around the periphery of the core (see FIG. 6B). The diameter of individual amyloid fibrils within the human Alzheimer's disease plaque and the Aβ with perlecan produced plaque, were determined to be both 7–10 nm (by measuring fibrils when viewed at a magnification of 100,000×). A similar "amyloid star" ultrastructural morphology was also observed following a 1 week co-incubation of Aβ 1–40 with dextran sulfate (at an Aβ:dextran sulfate molar ratio of 1:5), and Aβ 1–40 with perlecan and dextran sulfate (see Example 9 for details of combination co-incubations). These ultrastructural studies demonstrated that the amyloid plaques induced by perlecan and/or highly sulfated macromolecules were virtually identical to the "amyloid star" plaques present in human Alzheimer's disease brain. In addition, "amyloid star" ultrastructural appearance of plaques formed following incubation of Aβ 1–40 with perlecan, sulfated GAGs or related sulfated macromolecules correlates well with the observations made at the light microscopic level (i.e. maltese-cross after staining with Congo red and viewing under polarized light).

Example 8

Comparison of Artificial Amyloid Plaque Core Formation to Isolated Human Alzheimer's Disease Amyloid Plaque Cores: Scanning Electron Microscopy Studies In the next study, scanning electron microscopy was utilized to determine whether there were similarities in surface topography between amyloid plaque cores isolated from human Alzheimer's disease brain, and those induced in vitro by perlecan or other highly sulfated macromolecules. In this study, 125 μM of Aβ 1–40 (Bachem Inc) was incubated in double distilled water for 1 week at 37° C. either alone, or in the presence of 0.625 μM of perlecan (Aβ:perlecan molar ratio of 200:1; Aβ:perlecan weight ratio of 1:1) or dextran sulfate (Aβ:dextran sulfate molar ratio of 1:5). In addition, 0.625 μM of perlecan alone was incubated for 1 week at 37° C. Comparisons were made to isolated amyloid plaque cores derived from Alzheimer's disease brain (see example 7 for isolation procedure). A 10 μl aliquot of each sample in double distilled de-ionized water was air-dried for one hour on a freshly cleaved mica square. The dried sample was then fixed in situ with 3% glutaraldehyde in 0.1 M NaPO$_4$ buffer (pH 7.3) for 10 minutes. After rinsing 3 times with filtered distilled water, the samples were post-fixed for 10 minutes with 1% osmium tetroxide in distilled water, rinsed as before and air-dried again. The squares were then mounted on aluminum SEM stubs with silver paste and sputter coated with 10–20 nm Au/Pd. Samples were then examined and photographed with a JSM 6300F (JOEL Ltd., Tokyo, Japan) scanning electron microscope, using 15 kv accelerating voltage, and 30° tilt.

Figure 7A:
FIGS. 7A–7F are photomicrographs of amyloid plaque core formation induced by perlecan or dextran sulfate and viewed by scanning electron microscopy.
Figure 7B:
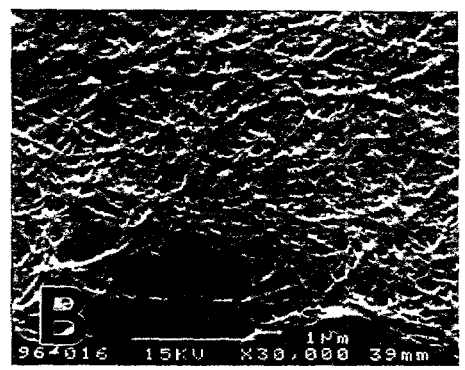
Figure 7C:
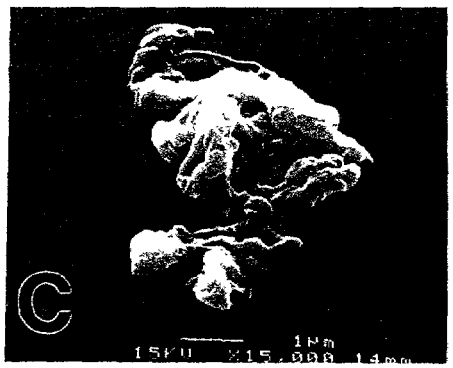
Figure 7D:
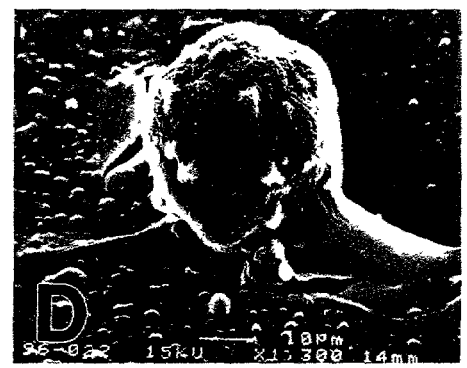
Figure 7E:
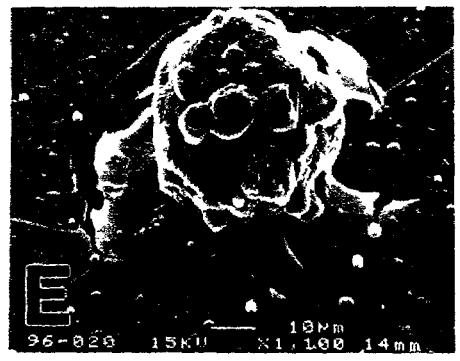
Figure 7F:

As shown in FIG. 7A, amyloid plaque cores derived from human Alzheimer's disease brain were spherical in shape and contained a somewhat ruffled surface morphology. Human amyloidplaque cores were usually from 15–30 μM in diameter. Aβ 1–40 alone following a 1 week incubation at 37° C. demonstrated bundles of fibrils in alternating patterns (FIG. 7B), with no spherical amyloid plaque core-like structure apparent. Perlecan alone demonstrated small globular structures that were irregular in shape (FIG. 7C) and also demonstrated lack of apparent formation of amyloid plaque-like deposits. However, following a 1 week co-incubation of Aβ 1–40 with perlecan, spherical amyloid plaque like structures were observed (FIGS. 7D and 7E). In comparison to amyloid plaque cores derived from human Alzheimer's disease brain, Aβ 1–40 with perlecan plaques were similarly rounded (usually from 20–40 μM in diameter), but contained a somewhat smooth surface topography than the ruffled surface of human amyloid plaque cores. In addition, in many instances, artificially induced amyloid plaque cores by perlecan had prominent globular structures protruding from the surface (FIGS. 7D and 7E). Aβ 1–40 with dextran sulfate (FIG. 6F) following a 1 week incubation at 37° C. showed a very similar surface morphology to human amyloid plaque cores, in that both contained a very ruffled surface topography. Since dextran sulfate is known to be a highly sulfated macromolecule, the ruffled morphology of human amyloid plaque cores similar to those induced by dextran sulfate suggests that sulfates may be important for the observation of the ruffled surface. Nonetheless, these studies demonstrated that spherical amyloid plaque core-like deposits are induced by perlecan or highly sulfated macromolecules such as dextran sulfate, and correlates well with observations made at the light microscopic level and by transmission electron microscopy.

Example 9

Compact Amyloid Plaque Formation by Incubation of Aβ+Perlecan+Sulfated Macromolecules Besides the formation of congophilic maltese-cross amyloid plaques by the 1 week co-incubation of Aβ 1–40 with perlecan, further studies indicated that stable compact plaque deposits could also be obtained by combination incubations. For example, Aβ 1–40 with perlecan and sulfated macromolecules appeared to also produce similar compact plaque deposits as described herein. In such a study, 125 μM of Aβ 1–40 (Bachem Inc., Torrance, Calif.) was incubated in double distilled water for 1 week at 37° C. in the presence of 0.625 μM of perlecan (i.e. Aβ:perlecan molar ratio=200:1; Aβ:perlecan weight ratio=1:1) and dextran sulfate (Sigma; M$_r$=8 kDa) or pentosan polysulfate (Sigma; M$_r$=3 kDa)(at an Aβ:dextran sulfate or Aβ:pentosan polysulfate molar ratio of 1:5). At 1 week, 5 μl aliquots of the incubation mixtures were air-dried on gelatin-coated slides, stained with Congo red and viewed under polarized light as described in Example 1. Congophilic maltese-cross amyloid plaque formation was observed in all samples of Aβ 1–40 with perlecan and dextran sulfate or Aβ 1–40 with perlecan and pentosan polysulfate. A similar congophilic maltese-cross amyloid plaque formation was even observed following a 1 week incubation at 37° C. of Aβ 1–40 with perlecan and chondroitin-4-sulfate (Aβ:C-4-S molar ration of 1:5). These studies demonstrated that addition of sulfated GAGs or sulfated macromolecules (i.e. dextran sulfate or pentosan polysulfate) to Aβ 1–40 with perlecan still resulted in compact plaque formation in vitro demonstrating 1) the stability of the amyloid plaques formed, and 2) that sulfated molecules do not appear to hinder the formation of such congophilic maltese-cross compact amyloid plaques.

Example 10

Characteristics of Congophilic Maltese-Cross Amyloid Plaques Formed in vitro

The congophilic maltese-cross amyloid plaques formed by a 1 week incubation of Aβ 1–40 with perlecan or sulfated GAGs (i.e. heparin and heparan sulfate) or sulfated macromolecules (i.e dextran sulfate, pentosan polysulfate, and polyvinyl sulphonate) were found to be very stable in solution (water or Tris-buffered saline) and were found not to be altered even after 8 weeks in solution. In addition, preliminary studies using pre-formed compact amyloid plaques demonstrated that these plaques can be successfully infused into rodent brain following a 1 or 2-week infusion using techniques as previously described (Snow et al, *Neuron* 12:219–234, 1994). These latter investigations not only demonstrated the stability of the compact amyloid plaques produced by the methodologies described herein, but also suggest the use of these amyloid plaques for development of new animal models to screen and identify anti-plaque therapeutics in vivo.

Further Aspects and Utilizations of the Invention

Applications to Identify Anti-Plaque Therapeutics

Congophilic maltese-cross compact amyloid plaques formed in vitro as described herein can be utilized for screening methods to identify anti-plaque therapeutics as lead compounds for the treatment of Alzheimer's disease or the prion diseases. In a preferred embodiment such screening methods will utilize amyloid proteins (Aβ or PrP), PGs, sulfated GAGs, sulfated or anionic macromolecules or fragments thereof, that are radiolabelled. In a preferred embodiment the Aβ 1–40 or PrP is bound to a radioactive label such as radioactive iodine (i.e. $^{125}$I). However, other appropriate labelling agents and techniques can be used and include, but are not limited to, an enzyme label, a fluorescent label, a chemiluminescent label, or an antigen label. Among isotopes, any radioactive sub stance that may be incorporated into the Aβ or PrP protein or fragments thereof may be used. Preferred isotopes include, but are not limited to $^{125}$I, $^{123}$I, and $^{131}$I. $^{131}$I has a shorter half-life and higher energy level. Iodine radioisotopes may be incorporated into the protein or protein fragments by oxidative iodination. Also, radioactive iodine may be incorporated by use of Bolton-Hunter reagent to add a 3-iodo-4-hydroxyphenylproprionyl or 3,5-diiodo-4-hydroxyproprionyl group to a nucleophile in the peptide.

Other isotopes may also be incorporated by reaction with nucleophile groups or peptides. For example, tritium ($^{3}$H) can be incorporated by reaction with propionyl-N-hydroxysuccinimide, or radioactive sulfur ($^{35}$S) can be incorporated by similar reagents. The labelling of GAGs or sulfated macromolecules using $^{35}$S by methods known to those in the art, would also allow the amyloid plaque cores formed in vitro to be labelled and monitored as described below. Radioactive phosphorous ($^{32}$P) may be incorporated by enzymatic methods. Additionally, various radioactive metal ions, such as $^{99}$m technetium, maybe incorporated into Aβ or PrP or fragments thereof, if an appropriate chelating group is added first.

For detection using in vitro assays according to the present invention, enzyme labelling is also useful. Among the preferred enzyme labels are peroxidases such as horseradish peroxidase (HRP), or phosphatases such as alkaline phosphatase.

Modifying the peptide or peptide fragment by adding an antigenic group that will bind with an antibody allows direct detection of the peptide or peptide fragment itself. For example, the antigen digoxigenin can be linked to a peptide, and then visualized with a labelled digoxigenin-specific antibody, or labelled anti-antibody.

Although less sensitive than radioisotopes, fluorophores may also be incorporated into the Aβ or PrP peptide and detected according to known fluorescent detection techniques. Examples of suitable fluorophores include fluorescein, Texas red, and the like.

Direct or indirect chemiluminescent labels may also be used according to the invention such as dioxetanes, For example, the Aβ or PrP peptide would be modified with a group that is capable of emitting light as it decomposes.

In addition, an avidin-biotin system maybe used to detect the Aβ or PrP peptide or peptide fragment in an in vitro assay. For example, the peptide or fragment may be functionalized with biotin, and avidin or streptavidin added to detect the protein or fragment.

Once the Aβ or PrP is appropriately labelled as described above, it is combined with specific PGs, GAGs, sulfated or anionic macromolecules as described herein and incubated for 1 week at 37° C. to form congophilic maltese-cross compact amyloid plaques. The labelled plaques will first be tested to ensure that the staining and structural features of the amyloid plaques formed as the same as those formed in the absence of label. The parameters to ensure plaque stability following an appropriate labelling technique include:

a) a spherical or compact shape of the plaque formed, b) a maltese-cross pattern (i.e. red color of plaque 90 degrees to green color of plaque) of congophilia following staining with Congo red, and when viewed under polarized light, c) positive staining with Thioflavin S, d) a spherical and/or "amyloid star" appearance when viewed by electron microscopy, and e) a spherical or compact shape (with plaques 10–40 μM in diameter) when viewed by scanning electron microscopy. If the labelled amyloid plaques demonstrate one or more of the staining and structural features as described above they can be utilized for a variety of in vitro methods to identify anti-plaque therapeutics.

In one such preferred method, labelled plaque cores are seeded onto 96-well plates, and allowed to bind overnight. Different methods, known to those in the art, will be utilized to determine the optimum for such labelled plaque binding to wells. Once such binding is achieved, a number of compounds or agents in various solutions/buffers (to be determined empirically) will be added to wells containing labelled plaques for various times of incubation (to be determined empirically). Agents or compounds able to break apart, disrupt or eliminate the staining characteristics or structure of the compact amyloid plaques (as described below) are identified by comparing staining and structural characteristics to those wells that do not contain compound or agents, or those that contain compounds or agents thought not to be an effective in altering plaque architecture. Agents or compounds that are able to break apart, disrupt or eliminate the staining or structural composition of the compact amyloid plaques can be identified by a variety of means including:

1) an increase in radiolabel in the supernatant (i.e. liquid phase) in wells of plaques treated with compound or agent in comparison to those wells of plaques not treated with compound or agent. The method of detecting the label such as radioactive isotopes will vary according to the isotope and its corresponding energy level. For example, a gamma counter is capable of detecting $^{125}$I, but not $^{3}$H (tritium) or $^{35}$S-sulfate, where a scintillation counter will be required. The increase in label in the supernatant are those plaques that have been disrupted or broken apart, demonstrating that the given compound or agent was effective in breaking apart or disrupted the plaque architecture and is therefore identified as a potential anti-plaque therapeutic. Such identified agents or compounds can be further identified by secondary or tertiary screens including, but not limited to: 1) a decrease or elimination of the maltese-cross pattern of congophilia following staining with Congo red, and when viewed under polarized light indicating that the given compound or agent was effective in decreasing or altering the amyloid fibril structure, and is therefore identified as a potential anti-plaque therapeutic, 2) a decrease or elimination of positive staining with Thioflavin S indicating that the given compound or agent was effective in decreasing or altering the amyloid fibril structure, and is therefore identified as a potential anti-plaque therapeutic 3) a decrease, alteration or elimination of the spherical and/or "amyloid star" appearance when viewed by electron microscopy indicating that the given compound or agent was effective in altering the architecture of the amyloid plaque, and is therefore identified as a potential anti-plaque therapeutic, and/or 4) a decrease, alteration or elimination of the spherical or compact shape (with plaques 10–40 µM in diameter) of the amyloid plaque when viewed by scanning electron microscopy indicating that the given compound or agent was effective in altering the architecture of the amyloid plaque, and is therefore identified as a potential anti-plaque therapeutic.

Unlabelled peptides of Aβ 1–40 can be purchased from a variety of commercial sources such as Bachem Inc (Torrance, Calif., USA). Alternatively the peptide can be synthesized by solid-phase fluorenylmethoxycarbonyl ("Fm° C. infinity) chemistry using techniques described (Stewart and Young, *Solid Phase Peptide Synthesis* (2nd edition), Pierce Chemical Company, Rockford, Ill, pp. 74–103 and 147–168, 1984; DH Schlesinger, *Macromolecular Sequencing and Synthesis, Selected Methods and Applications*, pp. 153–220, Alan R. Liss Inc., New York, 1988; G R Marshall, *Peptides, Chemistry and Biology*, pages 198–201, ESCOM Science Publishers, Netherlands (1988), the disclosures of which are incorporated by reference herein.

Peptides containing aromatic amino acids can be radiolabelled by oxidative radioiodination using Na $^{125}$I and chloramine-T and separated from free iodine by reverse-phase absorption using the methods of W M Hunter and F C Greenwood, *Nature* 194:495, 1962; A E Bolton and W M Hunter, *Biochem. J.* 133:529, 1973; and H P Too and J E Maggio, *Meth. Neurosc.* 6;232, 1991, the disclosures of which are incorporated by reference therein.

Another method of in vitro screening to identify anti-plaque therapeutics will utilize unlabelled compact amyloid plaques formed in vitro as described herein, that demonstrate the maltese-cross pattern when stained with Congo red and viewed under polarized light. Compounds or agents, following incubation with the compact amyloid plaque for an appropriate time (to be determined empirically) that are able to inhibit, decrease or eliminate the congophilic maltese-cross pattern of the plaque are identified utilizing polarization microscopy as potential anti-plaque therapeutics. In such a method, compact amyloid plaques will first be formed in vitro which demonstrate a typical maltese-cross pattern following staining with Congo red and when viewed under polarized light (as described herein). Following incubation with a test compound (at the appropriate dosage and incubation time to be determined empirically), compact amyloid plaques will be air-dried on gelatin-coated slides (as described herein), stained with Congo red, and viewed under polarization microscopy to determine if a given compound or agent is capable of inhibition, disruption or elimination of the amyloid plaque structure such that there is a loss of congophilia and/or maltese-cross formation. Secondary and tertiary screens will include analysis of such plaques following incubation of the given agent or compound by transmission and scanning electron microscopy.

Another method of in vitro screening to identify anti-plaque therapeutics will utilize compact amyloid plaques formed in vitro as described herein, that demonstrate positive staining when stained with Thioflavin S and when viewed by fluorescent microscopy. Compounds or agents, following incubation with the compact amyloid plaques for an appropriate time (to be determined empirically) that are able to decrease or eliminate the positive Thioflavin S fluorescence of the plaque are identified as potential anti-plaque therapeutics. Secondary and tertiary screens will include analysis of such plaques following incubation of the given agent or compound by transmission and scanning electron microscopy.

Yet another method of in vitro screening to identify anti-plaque therapeutics will utilize compact amyloid plaques formed in vitro as described herein, that demonstrate a spherical or "amyloid star" appearance when viewed by transmission electron microscopy. Compounds or agents, following incubation with the compact amyloid plaques for an appropriate time (to be determined empirically) that are able to disrupt or alter the spherical plaque shape or "amyloid star" appearance are identified as potential anti-plaque therapeutics.

Yet another method of in vitro screening to identify anti-plaque therapeutics will utilize compact amyloid plaques formed in vitro as described herein, that demonstrate a spherical shape with amyloid plaque diameters of 10–40 µm (average plaque diameter of 25 µm) when viewed by scanning electron microscopy. Compounds or agents, following incubation with the compact amyloid plaques for an appropriate time (to be determined empirically) that are able to disrupt or alter the spherical plaque shape or substantially decrease the diameter of the amyloid plaque are identified as potential anti-plaque therapeutics.

Yet another method of in vitro screening to identify anti-plaque therapeutics will utilize the size and shape of the compact amyloid plaques formed as described herein. Agents or compounds which inhibit, disrupt or eliminate the structure (i.e. size and/or diameter) of the spherical amyloid plaques can be identified using methodologies involving a cell sorter. In such assays, compact spherical amyloid plaques formed in vitro can be placed through a cell sorter to determine the average diameter (and range of diameters) of such plaques. In one preferred embodiment, amyloid plaque cores formed are loaded on a Coulter EPICS Elite ESP cell sorter (Coulter Corporation, Hialeah, Florida) and run through at a flow rate of 1428 particles/sec through a 100 µM 3× tip. An argon laser with an excitation maximum at 488 nm is used for sorting based on side scatter. Plaque cores selected will be based on size (10–50µM). Based on our observations by electron microscopy, the amyloid plaques formed in vitro by methods described herein usually have a range of diameters from 10–40 µm, with an average diameter of 25 µm. Following incubation with a given compound or agent under the appropriate conditions and incubation times (to be determined empirically), plaques formed in the absence of agent or compounds are compared to plaques formed that have been incubated with agents or compounds, by assessment using a cell sorter to determine the average plaque diameter (i.e. size). In another method, plaques formed in vitro using procedures as described herein, are treated with a compound or agent for a specific time (to be determined empirically), and then the average diameter of such treated plaques are determined using a cell sorter and compared to the average diameter of untreated plaques. If a given compound or agent is effective in breaking apart or disrupting the size (and hence diameter) of compact plaques then an increase in the proportion of smaller diameters (i.e. smaller plaques or its broken apart constituents) will be observed. Compounds or agents, following incubation with the compact amyloid plaques for an appropriate time (to be determined empirically) that are able to disrupt or substantially decrease the diameter of amyloid plaques are identified as potential anti-plaque therapeutics.

Another potential utility of the amyloid plaques formed in vitro as described herein is to identify agents or compounds that are effective in reducing or eliminating the neurotoxic effects of Aβ or PrP. In a first set of experiments, it will be important to determine if the compact amyloid plaques formed in vitro as described herein caused toxicity to neurons in culture and/or in animal models (described below). For such cell culture experiments, compact amyloid plaques will first be formed in vitro as described herein, and will be placed in petri dishes containing primary neurons (isolated using standard techniques and known to those in the art), or neuronal cell lines. Following prolonged incubation (i.e. 48 or 72 hours) of amyloid plaques with neuronal cultures, levels of neurotoxicity (using standard assays known to those in the art) will be measured and compared to those cultures that do not contain amyloid plaques. If the compact amyloid plaques are able to demonstrate neurotoxicity effects in cell culture, then these amyloid plaques can be further utilized to screen for and identify agents or compounds that are potential anti-neurotoxic therapeutics. In such a method, compact amyloid plaques formed in vitro will be incubated in primary neuronal cultures, or in neuronal cell lines, for prolonged periods (i.e. 48 or 72 hours), and in the presence or absence of a given test compound or agent. Agents or compounds that are able to inhibit or decrease neurotoxicity caused by the incubation of amyloid plaques are then identified anti-neurotoxic agents.

Yet another utility of the present invention is to provide new animal models which demonstrate congophilic maltese-cross compact amyloid plaques in vivo. Such methods will include, but are not limited to, the injection, infusion or placement by other means, of compact amyloid plaques formed in vitro, into brain or other tissues. Such animals will provide new means to study the effects of compact amyloid plaque deposition and persistence in vivo and will provide new means to test the effectiveness of potential anti-plaque therapeutics in animal models. In a preferred embodiment, Aβ-containing compact amyloid plaques formed in vitro by the methods described herein will be placed in distilled water or Tris-buffered saline (pH 7.4) and injected, infused or placed by other means into the brains of animals. Such amyloid plaque models can be used to study the effects of compact amyloid plaque deposition and persistence in brain and will provide new methods to test the effectiveness of potential anti-plaque therapeutics in animal models. In preferred embodiments, such models can be used to identify anti-plaque therapeutics for the treatment of Alzheimer's disease and prion diseases.

Amyloid Plaques in vivo as New Animal Models to Identify Alzheimer's Disease Anti-Plague Therapeutics For example, as a new model of Alzheimer's disease compact amyloid plaque deposition, Aβ-containing compact amyloid plaques formed in vitro (as described herein) are continuously infused into the hippocampus of groups of rats or mice. In a preferred embodiment, male Harlan Sprague-Dawley rats are first anesthetized with pentobarbital (50 mg/kg) and a 27 gauge stainless steel cannula is stereotactically implanted into the hippocampus using bregma as reference point (Aβ−4.8; ML 3.5; DV 3.0) and secured to the skull by machine screws and dental acrylic. The cannula is connected via a 15 cm coil of vinyl tubing to a model 2002 osmotic minipump (Alzet Inc.) placed subcutaneously beneath the shoulder blades. The infused solution is contained entirely within the coil of vinyl tubing and separated from water in the pump (dyed blue with food coloring) by a 3 cm air spacer. Successful performance of the pumps is confirmed by measuring movement of the air spacer and blue saline solution following sacrifice. Compact amyloid plaques formed in vitro by methods as described herein are infused directly into hippocampus at a flow rate of 0.5 μl/hr for 1 or 2 weeks. At the end of the infusion period, rats are sacrificed by an overdose of pentobarbital and perfused with 100 ml of saline followed by 150 ml of 4% paraformaldehyde buffered with phosphate (pH 7.4), the brains were removed and postfixed for 48 hr, and transferred to phosphate-buffered saline for frozen tissue sectioning. Consecutive 25 μm serial sections are then cut using a sliding microtome and placed on gelatin-coated slides.

From each animal, 100 consecutive serial sections are cut and stained with cresyl violet to identify the area occupied by the infusion site. Usually, the infusion site spans 40–60 serial sections. Congo red staining (Puchtler et al., *J. Histochem. Cytochem.* 10:355–364, 1962) and Thioflavin S fluorescence (Elghetany and Saleem, Stain Tech. 63:201–212, 1988) are then used on every 10th section spanning through the entire infusion site to determine the extent and consistency of compact amyloid plaque deposition in these animals. The % of animals containing congophilic maltese-cross amyloid plaque deposits is assessed by blind scoring of tissue sections (scoring of every 10th congo red stained sections through the entire infusion site). In addition, the number of compact amyloid plaques can be quantitiated by counting within a given field of magnification. Detection of infused Aβ-containing compact amyloid plaques are monitored by staining sections throughout the infusion site (i.e. every 10th section through the infusion site) with Congo red and viewing under polarized light to identify congophilic maltese-cross amyloid plaques in vivo. In addition, sections are stained throughout the infusion site (i.e. every 10th section through the infusion site) with Thioflavin S and viewed by fluorescence microscopy to identify spherical Thioflavin S amyloid plaque deposits. Lastly, Aβ-containing plaques are identified using histochemical techniques such as detection using a polyclonal antibody against synthetic Aβ or a monoclonal antibody (6E10; Senetek, USA) which recognizes residues 1–17 of Aβ. Tissue sections with the anti-Aβ antibodies are pretreated for 3–5 minutes with 88% formic acid before immunostaining to aid in unmasking hidden antigenic sites as previously reported (Kitamoto et al., *Lab. Invest.* 57:230–236, 1987). For immunostaining, negative controls consisted of using Tris-buffered saline (pH 7.4) instead of the primary antibody and/or preabsorption experiments using the primary antibody in the presence of excess antigen (Snow et al., *Am. J. Path.* 137:1253–1270, 1990).

These animal models may be used to rapidly screen potential anti-plaque therapeutics targeting compact amyloid plaque formation, deposition, accumulation and/or persistence. In a preferred embodiment, compact amyloid plaques initially formed in vitro (as described herein) plus a potential therapeutic agent or compound are directly infused into the hippocampus (as described above) of a group of animals, and comparisons are made to a group of animals infused with only compact amyloid plaques (i.e. in the absence of a test compound or agent). Compounds or agents found to reduce, eliminate or disrupt compact amyloid plaque formation, deposition, accumulation and/or persistence (as determined by Congo red or Thioflavin S scoring) in vivo are then identified as having potential anti-plaque therapeutic value.

In another preferred embodiment, compound or agents can be tested for their effectiveness in reducing or eliminating compact amyloid plaque persistence over prolonged periods of time. In this model, groups of animals (usually 10 animals per group) are infused with compact amyloid plaques formed in vitro plus a compound or agent, and directly compared to groups of animals (usually 10 animals per group) infused with only compact amyloid plaques (i.e. in the absence of a test compound or agent). Following a 1 week infusion (as described above), the cannulae are removed with the animals under anesthesia, and the animals are then allowed to recover until sacrifice 1, 3, 6 or 12 months later. Serial sections are cut and compact amyloid plaque persistence is scored as described above. It is believed that compact amyloid plaques will persistent in brain over time. Potent therapeutic compounds or agents will be those that effectively reduce or eliminate compact amyloid plaques observed in comparison to those animals not given the therapeutic compound or agent. These compounds or agents can therefore be referred to as compounds or agents which effectively reduce compact amyloid plaque persistence in vivo.

In yet another preferred embodiment, compounds or agents can be tested for reducing or eliminating pre-deposited compact amyloid plaques. In this model, two groups of animals (usually 10 animals per group) are infused with compact amyloid plaques (formed as described herein). Following a 1 week infusion (as described above), the cannulae and osmotic pumps are changed (with the animals under anesthesia), and a new cannulae connected by vinyl tubing to a new osmotic pump, contains either vehicle only (ie. double distilled water) or a potential therapeutic compound or agent. Following a 1 week continuous infusion of either the vehicle or the potential therapeutic compound or agent of interest, the animals are sacrificed. Serial sections are then cut through the entire infusion site and the extent of compact amyloid plaques are measured by arbitrary blind scoring as described above. Potential therapeutic compounds or agents will be those that are able to effectively remove pre-deposited compact amyloid plaque deposits, or those compounds or agents that can neutralize the possible effects of such plaques on cells (i.e. neurotoxicity). It is anticipated that little to no reduction in the amount of compact amyloid plaques will be observed in the group of animals infused with vehicle only. These compounds can therefore be referred to as therapeutic compounds or agents which effectively reduce pre-deposited compact amyloid plaques in vivo.

Amyloid Plaques in vivo as New Animal Models to Identify Prion Disease Anti-Plaque Therapeutics For example, as a new model of prion disease compact amyloid plaque deposition, PrP-containing compact amyloid plaques formed in vitro (as described herein) are continuously infused into the hippocampus (or cerebellum) of groups of rats or mice. In a preferred embodiment, male Harlan Sprague-Dawley rats are first anesthetized with pentobarbital (50 mg/kg) and a 27 gauge stainless steel cannula is stereotactically implanted into the hippocampus using bregma as reference point (AP −4.8; ML 3.5; DV 3.0) and secured to the skull by machine screws and dental acrylic. The cannula is connected via a 15 cm coil of vinyl tubing to a model 2002 osmotic minipump (Alzet Inc.) placed subcutaneously beneath the shoulder blades. The infused solution is contained entirely within the coil of vinyl tubing and separated from water in the pump (dyed blue with food coloring) by a 3 cm air spacer. Successful performance of the pumps is confirmed by measuring movement of the air spacer and blue saline solution following sacrifice. Compact amyloid plaques formed in vitro by methods as described herein are infused directly into hippocampus at a flow rate of 0.5 μl/hr for 1 or 2 weeks. At the end of the infusion period, rats are sacrificed by an overdose of pentobarbital and perfused with 100 ml of saline followed by 150 ml of 4% paraformaldehyde buffered with phosphate (pH 7.4), the brains were removed and postfixed for 48 hr, and transferred to phosphate-buffered saline for frozen tissue sectioning. Consecutive 25 μm serial sections are then cut using a sliding microtome and placed on gelatin-coated slides.

From each animal, 100 consecutive serial sections are cut and stained with cresyl violet to identify the area occupied by the infusion site. Usually, the infusion site spans 40–60 serial sections. Congo red staining (Puchtler et al., *J. Histochem. Cytochem.* 10:355–364, 1962) and Thioflavin S fluorescence (Elghetany and Saleem, *Stain Tech.* 63:201–212, 1988) are then used on every 10th section spanning through the entire infusion site to determine the extent and consistency of compact amyloid plaque deposition in these animals. The % of animals containing congophilic maltese-cross amyloid plaque deposits is assessed by blind scoring of tissue sections (scoring of every 10th congo red stained sections through the entire infusion site). In addition, the number of compact amyloid plaques can be quantitiated by counting within a given field of magnification. Detection of infused PrP-containing compact amyloid plaques are monitored by staining sections throughout the infusion site (i.e. every 10th section through the infusion site) with Congo red and viewing under polarized light to identify congophilic maltese-cross amyloid plaques in vivo. In addition, sections are stained throughout the infusion site (i.e. every 10th section through the infusion site) with Thioflavin S and viewed by fluorescence microscopy to identify spherical Thioflavin S amyloid plaque deposits. Lastly, PrP-containing plaques are identified using histochemical techniques such as detection using antibodies which recognize the PrP protein (obtained commercially from a number of different sources). Tissue sections with the anti-PrP antibodies are pretreated for 3–5 minutes with 88% formic acid before immunostaining to aid in unmasking hidden antigenic sites as previously reported (Kitamoto et al., *Lab. Invest.* 57:230–236, 1987). For immunostaining, negative controls consisted of using Tris-buffered saline (pH 7.4) instead of the primary antibody and/or preabsorption experiments using the primary antibody in the presence of excess antigen (Snow et al., *Am. J. Path.* 137:1253–1270, 1990).

These animal models may be used to rapidly screen potential anti-plaque therapeutics targeting compact amyloid plaque formation, deposition, accumulation and/or persistence. In a preferred embodiment, compact amyloid plaques initially formed in vitro (as described herein) plus a potential therapeutic agent or compound are directly infused into the hippocampus (as described above) of a group of animals, and comparisons are made to a group of animals infused with only compact amyloid plaques (i.e. in the absence of a test compound or agent). Compounds or agents found to reduce, eliminate or disrupt compact amyloid plaque formation, deposition, accumulation and/or persistence (as determined by Congo red or Thioflavin S scoring) in vivo are then identified as having potential anti-plaque therapeutic value.

In another preferred embodiment, compound or agents can be tested for their effectiveness in reducing or eliminating compact amyloid plaque persistence over prolonged periods of time. In this model, groups of animals (usually 10 animals per group) are infused with compact amyloid plaques formed in vitro plus a compound or agent, and directly compared to groups of animals (usually 10 animals per group) infused with only compact amyloid plaques (i.e. in the absence of a test compound or agent). Following a 1 week infusion (as described above), the cannulae are removed with the animals under anesthesia, and the animals are then allowed to recover until sacrifice 1, 3, 6 or 12 months later. Serial sections are cut and compact amyloid plaque persistence is scored as described above. It is believed that compact amyloid plaques will persistent in brain over time. Potent therapeutic compounds or agents will be those that effectively reduce or eliminate compact amyloid plaques observed in comparison to those animals not given the therapeutic compound or agent. These compounds or agents can therefore be referred to as compounds or agents which effectively reduce compact amyloid plaque persistence in vivo.

In yet another preferred embodiment, compounds or agents can be tested for reducing or eliminating pre-deposited compact amyloid plaques. In this model, two groups of animals (usually 10 animals per group) are infused with compact amyloid plaques (formed as described herein). Following a 1 week infusion (as described above), the cannulae and osmotic pumps are changed (with the animals under anesthesia), and a new cannulae connected by vinyl tubing to a new osmotic pump, contains either vehicle only (ie. double distilled water) or a potential therapeutic compound or agent. Following a 1 week continuous infusion of either the vehicle or the potential therapeutic compound or agent of interest, the animals are sacrificed. Serial sections are then cut through the entire infusion site and the extent of compact amyloid plaques are measured by arbitrary blind scoring as described above. Potent therapeutic compounds or agents will be those that are able to effectively remove pre-deposited compact amyloid plaque deposits. It is anticipated that little to no reduction in the amount of compact amyloid plaques will be observed in the group of animals infused with vehicle only. These compounds can therefore be referred to as therapeutic compounds or agents which effectively reduce pre-deposited compact amyloid plaques in vivo.

RESEARCH APPLICATIONS

Compact amyloid plaques formed in vitro are expected to be useful for a variety of different research applications. In one example, pre-formed compact amyloid plaques can be placed in cultures containing other cells (examples: neurons, microglia, astrocytes, oligodendrocytes) and the response of the cells (i.e. phagocytosis, degradation) to such amyloid plaques in culture can be determined. In another example, the response of individual macromolecules (i.e. other components implicated in amyloidosis such as apolipoprotein E, amyloid P component, complement factors, cytokines, inflammatory factors) to such compact amyloid plaques in culture can also be assessed using standard techniques to those known in the art.

In addition, the effects of compact amyloid plaque deposition, accumulation and persistence on cell architecture and/or the metabolism of various macromolecules (i.e beta-amyloid precursor protein, specific proteoglycans) can also be studied in vivo. Such uses of compact amyloid plaques in vitro and in vivo will generate new avenues of research with practical and unexplored applications in the future.

Another potential application of the present invention is to provide pre-formed compact amyloid plaques, or the ability to produce such compact amyloid plaques, in a kit form. Such a kit could be useful for the screening and identification of compounds or agents that have potential as anti-plaque therapeutics. Such a kit could comprise of a) a first container having A$\beta$ 1–40 (in solution or lyophilized) at the appropriate amount or concentration needed (described herein) for compact amyloid plaque formation, b) a second container containing perlecan, the ~220 kDa, specific GAGs (such as heparin or heparan sulfate), specific sulfated macromolecules (such as dextran sulfate, pentosan polysulfate or polyvinyl sulphonate) in solution or lyophilized, at the appropriate amount or concentration needed (described herein) for compact amyloid plaque formation. Such congophilic maltese-cross amyloid plaque formation would occur following the mixing of the appropriate amounts from each of the two containers, and following incubation at 37° C. for 1 week.

In another kit, the compact amyloid plaques could be pre-formed and then frozen or lyophilized for distribution. Once received by the researcher or individual, the compact amyloid plaques may be re-formed by placing in an appropriate solution such as distilled water or Tris-buffered saline (pH 7.4), and in an appropriate volume of solution. Such kits may be used for research and/or commercial applications.

With regard to systems and components above referred to, but not otherwise specified or described in detail herein, the workings and specifications of such systems and components and the manner in which they may be made or assembled or used, both cooperatively with each other and with the other elements of the invention described herein to effect the purposes herein disclosed, are all believed to be well within the knowledge of those skilled in the art. No concerted attempt to repeat here what is generally known to the artisan has therefore been made.

In compliance with the statute, the invention has been described in language more or less specific as to structural features. It is to be understood, however, that the invention is not limited to the specific features shown, since the means and construction shown comprise preferred forms of putting the invention into effect. The invention is, therefore, claimed in any of its forms or modifications within the legitimate and valid scope of the appended claims, appropriately interpreted in accordance with the doctrine of equivalents.

We claim:

1. A method for the formation of particular amyloid plaques, the method comprising in vitro co-incubation of beta-amyloid protein 1–40 (SEQ ID NO: 1) for at least 3–7 days at 30–45° C. with heparan sulfate, whereby spherical or compact shaped amyloid plaques are formed that demonstrate a Maltese-cross pattern when stained with Congo red and viewed under polarized light, and an amyloid star appearance when viewed by transmission electron microscopy, and further wherein the co-incubation is at a molar ratio of beta-amyloid protein to heparan sulfate within a range of 1:0.5 to 1:100.

2. The method of claim 1 wherein the molar ratio of beta-amyloid protein to heparan sulfate is about 1:5.

3. The method of claim 1 wherein the step of co-incubation of the amyloid protein with heparan sulfate is in distilled water or Tris-buffered saline (pH 7.0–7.4).

4. The method of claim 1 wherein the step of co-incubation has a duration of about 7 days.

5. The method of claim 1 wherein the step of co-incubation of the beta-amyloid protein with heparan sulfate occurs at about 37° C.

6. A method for the formation of particular amyloid plaques, the method comprising in vitro co-incubation of beta-amyloid protein 1–40 (SEQ ID NO: 1) for at least 3–7 days at 30–45° C. with heparan sulfate, whereby spherical or compact shaped amyloid plaques are formed that demonstrate a Maltese-cross pattern when stained with Congo red and viewed under polarized light, and an amyloid star appearance when viewed by transmission electron microscopy, and further wherein the co-incubation is at a weight ratio of beta-amyloid protein to heparan sulfate within a range of 1:0.4 to 1:100.

7. The method of claim 6 wherein the weight ratio of beta-amyloid protein to heparan sulfate is about 1:8 or 1:16.

8. The method of claim 6 wherein the step of co-incubation of the amyloid protein with heparan sulfate is in distilled water or Tris-buffered saline (pH 7.0–7.4).

9. The method of claim 6 wherein the step of co-incubation has a duration of about 7 days.

10. The method of claim 6 wherein the step of co-incubation of the beta-amyloid protein with heparan sulfate occurs at about 37° C.

* * * * *